United States Patent
Xu

(10) Patent No.: US 7,803,582 B2
(45) Date of Patent: Sep. 28, 2010

(54) RECOMBINANT VECTOR AND USE IN GENE THERAPY

(76) Inventor: Hongzhan Xu, 1014 Taney Ave., Frederick, MD (US) 21702

( * ) Notice: Subject to any disclaimer, the term of this patent is extended or adjusted under 35 U.S.C. 154(b) by 559 days.

(21) Appl. No.: 11/687,647

(22) Filed: Mar. 17, 2007

(65) Prior Publication Data

US 2008/0226675 A1    Sep. 18, 2008

(51) Int. Cl.
*C12P 19/34* (2006.01)

(52) U.S. Cl. .................. 435/91.4; 435/91.1; 435/91.32; 435/91.33

(58) Field of Classification Search ........................ None
See application file for complete search history.

(56) References Cited

U.S. PATENT DOCUMENTS

| 7,220,554 B2* | 5/2007 | Kabat et al. .................. 435/7.1 |
| 2002/0010415 A1* | 1/2002 | Simon .......................... 604/20 |

OTHER PUBLICATIONS

Xu et al. PNAS 2004;101;5652-7.*
Kao et al. J Virol 2003;77:11398-407.*

* cited by examiner

*Primary Examiner*—Q. Janice Li
(74) *Attorney, Agent, or Firm*—Yuan Qing Jiang

(57) ABSTRACT

A recombinant vector for delivering A3G genes into human cells comprising (i) a gene expression block including an A3G gene selected from a wild type A3G gene represented by SEQ ID NO: 1 and a mutant A3G gene and (ii) a group of elements from a modified lentiviral vector including lentiviral regions of packaging signal (ψ, psi), LTRs, RRE, and PBS; wherein said A3G gene is operably linked to the packaging signal (ψ, psi), LTRs, RRE, and PBS.

8 Claims, 22 Drawing Sheets

SEQUENCE LISTING

<160> NUMBER OF SEQ ID NOS: 8

<210> SEQ ID NO 1
<211> LENGTH: 1167
<212> TYPE: DNA
<213> ORGANISM: Homo sapiens
<220> FEATURE:
<221> NAME/KEY: exon
<222> LOCATION: (1)..(1167)

<400> SEQUENCE: 1

```
atg aag cct cac ttc aga aac aca gtg gag cga atg tat cga gac aca      48
Met Lys Pro His Phe Arg Asn Thr Val Glu Arg Met Tyr Arg Asp Thr
 1               5                  10                  15 ttc tcc tac aac ttt tat aat aga ccc atc ctt tct cgt cgg aat acc      96
Phe Ser Tyr Asn Phe Tyr Asn Arg Pro Ile Leu Ser Arg Arg Asn Thr
                20                  25                  30 gtc tgg ctg tgc tac gaa gtg aaa aca aag ggt ccc tca agg ccc cct     144
Val Trp Leu Cys Tyr Glu Val Lys Thr Lys Gly Pro Ser Arg Pro Pro
            35                  40                  45 ttg gac gca aag atc ttt cga ggc cag gtg tat tcc gaa ctt aag tac     192
Leu Asp Ala Lys Ile Phe Arg Gly Gln Val Tyr Ser Glu Leu Lys Tyr
        50                  55                  60 cac cca gag atg aga ttc ttc cac tgg ttc agc aag tgg agg aag ctg     240
His Pro Glu Met Arg Phe Phe His Trp Phe Ser Lys Trp Arg Lys Leu
 65                  70                  75                  80 cat cgt gac cag gag tat gag gtc acc tgg tac ata tcc tgg agc ccc     288
His Arg Asp Gln Glu Tyr Glu Val Thr Trp Tyr Ile Ser Trp Ser Pro
                 85                  90                  95 tgc aca aag tgt aca agg gat atg gcc acg ttc ctg gcc gag gac ccg     336
Cys Thr Lys Cys Thr Arg Asp Met Ala Thr Phe Leu Ala Glu Asp Pro
            100                 105                 110 aag gtt acc ctg acc atc ttc gtt gcc cgc ctc tac tac ttc tgg gac     384
Lys Val Thr Leu Thr Ile Phe Val Ala Arg Leu Tyr Tyr Phe Trp Asp
        115                 120                 125 cca gat tac cag gag gcg ctt cgc agc ctg tgt cag aaa aga gac ggt     432
Pro Asp Tyr Gln Glu Ala Leu Arg Ser Leu Cys Gln Lys Arg Asp Gly
    130                 135                 140 ccg cgt gcc acc atg aag atc atg aat tat gac gaa ttt cag cac tgt     480
Pro Arg Ala Thr Met Lys Ile Met Asn Tyr Asp Glu Phe Gln His Cys
145                 150                 155                 160 tgg agc aag ttc gtg tac agc caa aga gag cta ttt gag cct tgg aat     528
Trp Ser Lys Phe Val Tyr Ser Gln Arg Glu Leu Phe Glu Pro Trp Asn
                165                 170                 175 aat ctg cct aaa tat tat ata tta ctg cac atc atg ctg ggg gag att     576
Asn Leu Pro Lys Tyr Tyr Ile Leu Leu His Ile Met Leu Gly Glu Ile
            180                 185                 190 ctc aga cac tcg atg gat cca ccc aca ttc act ttc aac ttt aac aat     624
Leu Arg His Ser Met Asp Pro Pro Thr Phe Thr Phe Asn Phe Asn Asn
        195                 200                 205 gaa cct tgg gtc aga gga cgg cat gag act tac ctg tgt tat gag gtg     672
Glu Pro Trp Val Arg Gly Arg His Glu Thr Tyr Leu Cys Tyr Glu Val
    210                 215                 220 gag cgc atg cac aat gac acc tgg gtc ctg ctg aac cag cgc agg ggc     720
Glu Arg Met His Asn Asp Thr Trp Val Leu Leu Asn Gln Arg Arg Gly
225                 230                 235                 240
```

```
ttt cta tgc aac cag gct cca cat aaa cac ggt ttc ctt gaa ggc cgc      768
Phe Leu Cys Asn Gln Ala Pro His Lys His Gly Phe Leu Glu Gly Arg
                245                 250                 255 cat gca gag ctg tgc ttc ctg gac gtg att ccc ttt tgg aag ctg gac      816
His Ala Glu Leu Cys Phe Leu Asp Val Ile Pro Phe Trp Lys Leu Asp
            260                 265                 270 ctg gac cag gac tac agg gtt acc tgc ttc acc tcc tgg agc ccc tgc      864
Leu Asp Gln Asp Tyr Arg Val Thr Cys Phe Thr Ser Trp Ser Pro Cys
        275                 280                 285 ttc agc tgt gcc cag gaa atg gct aaa ttc att tca aaa aac aaa cac      912
Phe Ser Cys Ala Gln Glu Met Ala Lys Phe Ile Ser Lys Asn Lys His
    290                 295                 300 gtg agc ctg tgc atc ttc act gcc cgc atc tat gat gat caa gga aga      960
Val Ser Leu Cys Ile Phe Thr Ala Arg Ile Tyr Asp Asp Gln Gly Arg
305                 310                 315                 320 tgt cag gag ggg ctg cgc acc ctg gcc gag gct ggg gcc aaa att tca     1008
Cys Gln Glu Gly Leu Arg Thr Leu Ala Glu Ala Gly Ala Lys Ile Ser
                325                 330                 335 ata atg aca tac agt gaa ttt aag cac tgc tgg gac acc ttt gtg gac     1056
Ile Met Thr Tyr Ser Glu Phe Lys His Cys Trp Asp Thr Phe Val Asp
            340                 345                 350 cac cag gga tgt ccc ttc cag ccc tgg gat gga cta gat gag cac agc     1104
His Gln Gly Cys Pro Phe Gln Pro Trp Asp Gly Leu Asp Glu His Ser
        355                 360                 365 caa gac ctg agt ggg agg ctg cgg gcc att ctc cag aat cag gaa aac     1152
Gln Asp Leu Ser Gly Arg Leu Arg Ala Ile Leu Gln Asn Gln Glu Asn
    370                 375                 380 aag ctt ggg ccc tga                                                  1167
Lys Leu Gly Pro
385

<210> SEQ ID NO 2
<211> LENGTH: 1167
<212> TYPE: DNA
<213> ORGANISM: Artificial Sequence
<220> FEATURE:
<223> OTHER INFORMATION: Description of the sequence: A3GD128K, a mutant
      A3G, in which amino acid residue Aspartate (Asp, D) at position
      128 of wild type A3G sequence is substituted by Lysine (Lys, K).
<220> FEATURE:
<221> NAME/KEY: exon
<222> LOCATION: (1)..(1167)

<400> SEQUENCE: 2 atg aag cct cac ttc aga aac aca gtg gag cga atg tat cga gac aca       48
Met Lys Pro His Phe Arg Asn Thr Val Glu Arg Met Tyr Arg Asp Thr
1               5                   10                  15 ttc tcc tac aac ttt tat aat aga ccc atc ctt tct cgt cgg aat acc       96
Phe Ser Tyr Asn Phe Tyr Asn Arg Pro Ile Leu Ser Arg Arg Asn Thr
            20                  25                  30 gtc tgg ctg tgc tac gaa gtg aaa aca aag ggt ccc tca agg ccc cct      144
Val Trp Leu Cys Tyr Glu Val Lys Thr Lys Gly Pro Ser Arg Pro Pro
        35                  40                  45 ttg gac gca aag atc ttt cga ggc cag gtg tat tcc gaa ctt aag tac      192
Leu Asp Ala Lys Ile Phe Arg Gly Gln Val Tyr Ser Glu Leu Lys Tyr
    50                  55                  60 cac cca gag atg aga ttc ttc cac tgg ttc agc aag tgg agg aag ctg      240
His Pro Glu Met Arg Phe Phe His Trp Phe Ser Lys Trp Arg Lys Leu
65                  70                  75                  80 cat cgt gac cag gag tat gag gtc acc tgg tac ata tcc tgg agc ccc      288
His Arg Asp Gln Glu Tyr Glu Val Thr Trp Tyr Ile Ser Trp Ser Pro
            85                  90                  95
```

```
tgc aca aag tgt aca agg gat atg gcc acg ttc ctg gcc gag gac ccg      336
Cys Thr Lys Cys Thr Arg Asp Met Ala Thr Phe Leu Ala Glu Asp Pro
            100                 105                 110 aag gtt acc ctg acc atc ttc gtt gcc cgc ctc tac tac ttc tgg aaa      384
Lys Val Thr Leu Thr Ile Phe Val Ala Arg Leu Tyr Tyr Phe Trp Lys
            115                 120                 125 cca gat tac cag gag gcg ctt cgc agc ctg tgt cag aaa aga gac ggt      432
Pro Asp Tyr Gln Glu Ala Leu Arg Ser Leu Cys Gln Lys Arg Asp Gly
130                 135                 140 ccg cgt gcc acc atg aag atc atg aat tat gac gaa ttt cag cac tgt      480
Pro Arg Ala Thr Met Lys Ile Met Asn Tyr Asp Glu Phe Gln His Cys
145                 150                 155                 160 tgg agc aag ttc gtg tac agc caa aga gag cta ttt gag cct tgg aat      528
Trp Ser Lys Phe Val Tyr Ser Gln Arg Glu Leu Phe Glu Pro Trp Asn
                165                 170                 175 aat ctg cct aaa tat tat ata tta ctg cac atc atg ctg ggg gag att      576
Asn Leu Pro Lys Tyr Tyr Ile Leu Leu His Ile Met Leu Gly Glu Ile
            180                 185                 190 ctc aga cac tcg atg gat cca ccc aca ttc act ttc aac ttt aac aat      624
Leu Arg His Ser Met Asp Pro Pro Thr Phe Thr Phe Asn Phe Asn Asn
            195                 200                 205 gaa cct tgg gtc aga gga cgg cat gag act tac ctg tgt tat gag gtg      672
Glu Pro Trp Val Arg Gly Arg His Glu Thr Tyr Leu Cys Tyr Glu Val
210                 215                 220 gag cgc atg cac aat gac acc tgg gtc ctg ctg aac cag cgc agg ggc      720
Glu Arg Met His Asn Asp Thr Trp Val Leu Leu Asn Gln Arg Arg Gly
225                 230                 235                 240 ttt cta tgc aac cag gct cca cat aaa cac ggt ttc ctt gaa ggc cgc      768
Phe Leu Cys Asn Gln Ala Pro His Lys His Gly Phe Leu Glu Gly Arg
                245                 250                 255 cat gca gag ctg tgc ttc ctg gac gtg att ccc ttt tgg aag ctg gac      816
His Ala Glu Leu Cys Phe Leu Asp Val Ile Pro Phe Trp Lys Leu Asp
            260                 265                 270 ctg gac cag gac tac agg gtt acc tgc ttc acc tcc tgg agc ccc tgc      864
Leu Asp Gln Asp Tyr Arg Val Thr Cys Phe Thr Ser Trp Ser Pro Cys
            275                 280                 285 ttc agc tgt gcc cag gaa atg gct aaa ttc att tca aaa aac aaa cac      912
Phe Ser Cys Ala Gln Glu Met Ala Lys Phe Ile Ser Lys Asn Lys His
290                 295                 300 gtg agc ctg tgc atc ttc act gcc cgc atc tat gat gat caa gga aga      960
Val Ser Leu Cys Ile Phe Thr Ala Arg Ile Tyr Asp Asp Gln Gly Arg
305                 310                 315                 320 tgt cag gag ggg ctg cgc acc ctg gcc gag gct ggg gcc aaa att tca     1008
Cys Gln Glu Gly Leu Arg Thr Leu Ala Glu Ala Gly Ala Lys Ile Ser
                325                 330                 335 ata atg aca tac agt gaa ttt aag cac tgc tgg gac acc ttt gtg gac     1056
Ile Met Thr Tyr Ser Glu Phe Lys His Cys Trp Asp Thr Phe Val Asp
            340                 345                 350 cac cag gga tgt ccc ttc cag ccc tgg gat gga cta gat gag cac agc     1104
His Gln Gly Cys Pro Phe Gln Pro Trp Asp Gly Leu Asp Glu His Ser
            355                 360                 365 caa gac ctg agt ggg agg ctg cgg gcc att ctc cag aat cag gaa aac     1152
Gln Asp Leu Ser Gly Arg Leu Arg Ala Ile Leu Gln Asn Gln Glu Asn
370                 375                 380 aag ctt ggg ccc tga                                                  1167
Lys Leu Gly Pro
385
```

<210> SEQ ID NO 3

<211> LENGTH: 1167
<212> TYPE: DNA
<213> ORGANISM: Artificial Sequence
<220> FEATURE:
<223> OTHER INFORMATION: Description of the sequence: A3GP129D, a mutant A3G, in which amino acid residue Proline (Pro, P) at position 129 of wild type A3G sequence is substituted by Aspartate (Asp, D).
<220> FEATURE:
<221> NAME/KEY: exon
<222> LOCATION: (1)..(1167)

<400> SEQUENCE: 3

| | | | | | | | | | | | | | | | | |
|---|---|---|---|---|---|---|---|---|---|---|---|---|---|---|---|---|
| atg | aag | cct | cac | ttc | aga | aac | aca | gtg | gag | cga | atg | tat | cga | gac | aca | 48 |
| Met | Lys | Pro | His | Phe | Arg | Asn | Thr | Val | Glu | Arg | Met | Tyr | Arg | Asp | Thr | |
| 1 | | | | 5 | | | | | 10 | | | | | 15 | | |

| ttc | tcc | tac | aac | ttt | tat | aat | aga | ccc | atc | ctt | tct | cgt | cgg | aat | acc | 96 |
| Phe | Ser | Tyr | Asn | Phe | Tyr | Asn | Arg | Pro | Ile | Leu | Ser | Arg | Arg | Asn | Thr | |
| | | | 20 | | | | | 25 | | | | | 30 | | | |

| gtc | tgg | ctg | tgc | tac | gaa | gtg | aaa | aca | aag | ggt | ccc | tca | agg | ccc | cct | 144 |
| Val | Trp | Leu | Cys | Tyr | Glu | Val | Lys | Thr | Lys | Gly | Pro | Ser | Arg | Pro | Pro | |
| | | | | 35 | | | | | 40 | | | | | 45 | | |

| ttg | gac | gca | aag | atc | ttt | cga | ggc | cag | gtg | tat | tcc | gaa | ctt | aag | tac | 192 |
| Leu | Asp | Ala | Lys | Ile | Phe | Arg | Gly | Gln | Val | Tyr | Ser | Glu | Leu | Lys | Tyr | |
| | 50 | | | | | 55 | | | | | 60 | | | | | |

| cac | cca | gag | atg | aga | ttc | ttc | cac | tgg | ttc | agc | aag | tgg | agg | aag | ctg | 240 |
| His | Pro | Glu | Met | Arg | Phe | Phe | His | Trp | Phe | Ser | Lys | Trp | Arg | Lys | Leu | |
| 65 | | | | | 70 | | | | | 75 | | | | | 80 | |

| cat | cgt | gac | cag | gag | tat | gag | gtc | acc | tgg | tac | ata | tcc | tgg | agc | ccc | 288 |
| His | Arg | Asp | Gln | Glu | Tyr | Glu | Val | Thr | Trp | Tyr | Ile | Ser | Trp | Ser | Pro | |
| | | | | 85 | | | | | 90 | | | | | 95 | | |

| tgc | aca | aag | tgt | aca | agg | gat | atg | gcc | acg | ttc | ctg | gcc | gag | gac | ccg | 336 |
| Cys | Thr | Lys | Cys | Thr | Arg | Asp | Met | Ala | Thr | Phe | Leu | Ala | Glu | Asp | Pro | |
| | | | | 100 | | | | | 105 | | | | | 110 | | |

| aag | gtt | acc | ctg | acc | atc | ttc | gtt | gcc | cgc | ctc | tac | tac | ttc | tgg | gac | 384 |
| Lys | Val | Thr | Leu | Thr | Ile | Phe | Val | Ala | Arg | Leu | Tyr | Tyr | Phe | Trp | Asp | |
| | | 115 | | | | | 120 | | | | | 125 | | | | |

| gac | gat | tac | cag | gag | gcg | ctt | cgc | agc | ctg | tgt | cag | aaa | aga | gac | ggt | 432 |
| Asp | Asp | Tyr | Gln | Glu | Ala | Leu | Arg | Ser | Leu | Cys | Gln | Lys | Arg | Asp | Gly | |
| | 130 | | | | | 135 | | | | | 140 | | | | | |

| ccg | cgt | gcc | acc | atg | aag | atc | atg | aat | tat | gac | gaa | ttt | cag | cac | tgt | 480 |
| Pro | Arg | Ala | Thr | Met | Lys | Ile | Met | Asn | Tyr | Asp | Glu | Phe | Gln | His | Cys | |
| 145 | | | | | 150 | | | | | 155 | | | | | 160 | |

| tgg | agc | aag | ttc | gtg | tac | agc | caa | aga | gag | cta | ttt | gag | cct | tgg | aat | 528 |
| Trp | Ser | Lys | Phe | Val | Tyr | Ser | Gln | Arg | Glu | Leu | Phe | Glu | Pro | Trp | Asn | |
| | | | | 165 | | | | | 170 | | | | | 175 | | |

| aat | ctg | cct | aaa | tat | tat | ata | tta | ctg | cac | atc | atg | ctg | ggg | gag | att | 576 |
| Asn | Leu | Pro | Lys | Tyr | Tyr | Ile | Leu | Leu | His | Ile | Met | Leu | Gly | Glu | Ile | |
| | | | 180 | | | | | 185 | | | | | 190 | | | |

| ctc | aga | cac | tcg | atg | gat | cca | ccc | aca | ttc | act | ttc | aac | ttt | aac | aat | 624 |
| Leu | Arg | His | Ser | Met | Asp | Pro | Pro | Thr | Phe | Thr | Phe | Asn | Phe | Asn | Asn | |
| | | 195 | | | | | 200 | | | | | 205 | | | | |

| gaa | cct | tgg | gtc | aga | gga | cgg | cat | gag | act | tac | ctg | tgt | tat | gag | gtg | 672 |
| Glu | Pro | Trp | Val | Arg | Gly | Arg | His | Glu | Thr | Tyr | Leu | Cys | Tyr | Glu | Val | |
| | 210 | | | | | 215 | | | | | 220 | | | | | |

| gag | cgc | atg | cac | aat | gac | acc | tgg | gtc | ctg | ctg | aac | cag | cgc | agg | ggc | 720 |
| Glu | Arg | Met | His | Asn | Asp | Thr | Trp | Val | Leu | Leu | Asn | Gln | Arg | Arg | Gly | |
| 225 | | | | | 230 | | | | | 235 | | | | | 240 | |

| ttt | cta | tgc | aac | cag | gct | cca | cat | aaa | cac | ggt | ttc | ctt | gaa | ggc | cgc | 768 |
| Phe | Leu | Cys | Asn | Gln | Ala | Pro | His | Lys | His | Gly | Phe | Leu | Glu | Gly | Arg | |
| | | | | 245 | | | | | 250 | | | | | 255 | | |

| cat | gca | gag | ctg | tgc | ttc | ctg | gac | gtg | att | ccc | ttt | tgg | aag | ctg | gac | 816 |

```
                His Ala Glu Leu Cys Phe Leu Asp Val Ile Pro Phe Trp Lys Leu Asp
                                260                 265                 270 ctg gac cag gac tac agg gtt acc tgc ttc acc tcc tgg agc ccc tgc         864
Leu Asp Gln Asp Tyr Arg Val Thr Cys Phe Thr Ser Trp Ser Pro Cys
        275                 280                 285 ttc agc tgt gcc cag gaa atg gct aaa ttc att tca aaa aac aaa cac         912
Phe Ser Cys Ala Gln Glu Met Ala Lys Phe Ile Ser Lys Asn Lys His
    290                 295                 300 gtg agc ctg tgc atc ttc act gcc cgc atc tat gat gat caa gga aga         960
Val Ser Leu Cys Ile Phe Thr Ala Arg Ile Tyr Asp Asp Gln Gly Arg
305                 310                 315                 320 tgt cag gag ggg ctg cgc acc ctg gcc gag gct ggg gcc aaa att tca        1008
Cys Gln Glu Gly Leu Arg Thr Leu Ala Glu Ala Gly Ala Lys Ile Ser
                325                 330                 335 ata atg aca tac agt gaa ttt aag cac tgc tgg gac acc ttt gtg gac        1056
Ile Met Thr Tyr Ser Glu Phe Lys His Cys Trp Asp Thr Phe Val Asp
            340                 345                 350 cac cag gga tgt ccc ttc cag ccc tgg gat gga cta gat gag cac agc        1104
His Gln Gly Cys Pro Phe Gln Pro Trp Asp Gly Leu Asp Glu His Ser
        355                 360                 365 caa gac ctg agt ggg agg ctg cgg gcc att ctc cag aat cag gaa aac        1152
Gln Asp Leu Ser Gly Arg Leu Arg Ala Ile Leu Gln Asn Gln Glu Asn
370                 375                 380 aag ctt ggg ccc tga                                                    1167
Lys Leu Gly Pro
385

<210> SEQ ID NO 4
<211> LENGTH: 333
<212> TYPE: DNA
<213> ORGANISM: Artificial Sequence
<220> FEATURE:
<223> OTHER INFORMATION: Description of the sequence: mPcmv, sequence
      of the promoter modified from CMV (cytomegalovirus) promoter.

<400> SEQUENCE: 4
taatagtaat caattacggg gtcattagtt catagcccat atatggagtt ccgcgttaca        60
taacttacgg taaatggccc gcctggctga ccgcccaacg accccccgccc attgacgtca      120 ataatgacgt atgttcccat agtaacgcca tagggacttt ccattgacg tcaatgggtg       180 gagtatttac ggtaaactgc ccacttggca gtacatcaag tgtatcatat gccaagtacg      240 cccccctattg acgtcaatga cggtaaatgg cccgcctggc attatgccca gtacatgacc    300
ttatgggact ttcctacttg gcagtacatc tac                                   333

<210> SEQ ID NO 5
<211> LENGTH: 6866
<212> TYPE: DNA
<213> ORGANISM: Artificial Sequence
<220> FEATURE:
<223> OTHER INFORMATION: Description of the sequence: a recombinant
      vector, D3minP129D. D3minP129D is one version of D3min vector
      that is constructed from a lentivirus backbone. D3minP129D has a
      mutant A3G gene, P129D, inserted.

<400> SEQUENCE: 5
tggaagggct aatttggtcc caaaaaagac aagagatcct tgatctgtgg atctaccaca        60
cacaaggcta cttccctgat tggcagaact acacaccagg gccagggatc agatatccac      120
tgacctttgg atggtgcttc aagttagtac cagttgaacc agagcaagta aagaggcca       180 aataaggaga gaagaacagc ttgttacacc ctatgagcca gcatgggatg gaggacccgg      240
```

```
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
tgagtgctca aagtagtgtg tgcccgtctg ttgtgtgact ctggtaacta gagatccctc    600
agacccttttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaatacccca tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aacccttttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
```

```
taaaagcatt agtagaaatt tgtacagaaa tggaaaagga aggaaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagatttc tgggaagttc    2820
aattaggaat accacatcca attctgcaac aactgctgtt tatccatttc agaattgggt    2880
gtcgacatag cagaataggc gttactcgac agaggagagc aagaaatgga gccagtagat    2940
cctagactag agccctggaa gcatccagga agtcagccta aaactgcttg taccaattgc    3000
tattgtaaaa agtgttgctt tcattgccaa gtttgtttca tgacaaaagc cttaggcatc    3060
tcctatggca ggaagaagcg agacagcga cgaagagctc atcagaacag tcagactcat    3120
caagcttctc tatcaaagca gtaagtagta catgggcgcg cccatgtggc aggaagtagg    3180
aaaagcaatg tatgcccctc ccatcagtgg acaaattaga tgttcatcaa atattactgg    3240
gctgctatta acaagagatg gtggtaataa caacaatggg tccgagatct tcagacctgg    3300
aggaggcgat atgagggaca attggagaag tgaattatat aaatataaag tagtaaaaat    3360
tgaaccatta ggagtagcac ccaccaaggc aaagagaaga gtggtgcaga gagaaaaaag    3420
agcagtggga ataggagctt tgttccttgg gttcttggga gcagcaggaa gcactatggg    3480
ctgcacgtca atgacgctga cggtacaggc cagacaatta ttgtctgata tagtgcagca    3540
gcagaacaat ttgctgaggg ctattgaggc gcaacagcat ctgttgcaac tcacagtctg    3600
gggcatcaaa cagctccagg caagaatcct ggctgtggaa agatacctaa aggatcaaca    3660
gctcctgggg atttggggtt gctctggaaa actcatttgc accactgctg tgccttggaa    3720
tgctagttgg agtaataaat ctctggaaca gatttggaat aacatgacct ggatggagtg    3780
ggacagagaa attaacaatt acacaagctt aatacactcc ttaattgaag aatcgcaaaa    3840
ccagcaagaa aagaatgaac aagaattatt ggaattagat aaatgggcaa gtttgtggaa    3900
ttggtttaac ataacaaatt ggctgtggta tataaaatta ttcataatga tagtaggagg    3960
cttggtaggt ttaagaatag ttttgctgt actttctata gtgaatagag ttaggcaggg    4020
atattcacca ttatcgtttc agacccacct cccaatcccg aggggacccg acaggcccga    4080
aggaatagaa gaagaaggtg gagagagaga cagagacaga tccattcgat tagtgaacgg    4140
atccttagca cttatctggg acgatctgcg gagcctgtgc ctcttcagct accaccgctt    4200
gagagactta ctcttgattg taacgaggat tgtggaactt ctgggacgca gggggtggga    4260
agccctcaaa tattggtgga atctcctaca atattggagt caggagctaa agaatagtgc    4320
tgttagcttg ctcaatgcca cagccatagc agtagctgag gggacagata gggttataga    4380
agtagtacaa ggagcttgta gagctattcg ccacatacct agaagaataa gacagggctt    4440
ggaaaggatt ttgctataag atgggtggcg cggcctaata gtaatcaatt acgggggtcat    4500 tagttcatag cccatatatg gagttccgcg ttacataact tacggtaaat ggcccgcctg    4560
gctgaccgcc caacgacccc cgcccattga cgtcaataat gacgtatgtt cccatagtaa    4620
cgccaatagg gactttccat tgacgtcaat gggtggagta tttacggtaa actgcccact    4680
tggcagtaca tcaagtgtat catatgccaa gtacgccccc tattgacgtc aatgacggta    4740
aatggcccgc ctggcattat gcccagtaca tgaccttatg ggactttcct acttggcagt    4800
acatctacgg gatgaagcct cacttcagaa acacagtgga gcgaatgtat cgagacacat    4860
tctcctacaa cttttataat agacccatcc tttctcgtcg gaataccgtc tggctgtgct    4920
acgaagtgaa aacaaagggt ccctcaaggc cccctttgga cgcaaagatc tttcgaggcc    4980
```

```
aggtgtattc cgaacttaag taccacccag agatgagatt cttccactgg ttcagcaagt      5040
ggaggaagct gcatcgtgac caggagtatg aggtcacctg gtacatatcc tggagcccct      5100
gcacaaagtg tacaagggat atggccacgt tcctggccga ggacccgaag gttaccctga      5160
ccatcttcgt tgcccgcctc tactacttct gggacgacga ttaccaggag gcgcttcgca      5220
gcctgtgtca gaaaagagac ggtccgcgtg ccaccatgaa gatcatgaat tatgacgaat      5280
ttcagcactg ttggagcaag ttcgtgtaca gccaaagaga gctatttgag ccttggaata      5340
atctgcctaa atattatata ttactgcaca tcatgctggg ggagattctc agacactcga      5400
tggatccacc cacattcact ttcaacttta acaatgaacc ttgggtcaga ggacggcatg      5460
agacttacct gtgttatgag gtggagcgca tgcacaatga cacctgggtc ctgctgaacc      5520
agcgcagggg ctttctatgc aaccaggctc cacataaaca cggtttcctt gaaggccgcc      5580
atgcagagct gtgcttcctg gacgtgattc ccttttggaa gctggacctg gaccaggact      5640
acagggttac ctgcttcacc tcctggagcc cctgcttcag ctgtgcccag gaaatggcta      5700
aattcatttc aaaaaacaaa cacgtgagcc tgtgcatctt cactgcccgc atctatgatg      5760
atcaaggaag atgtcaggag gggctgcgca ccctggccga ggctggggcc aaaatttcaa      5820
taatgacata cagtgaattt aagcactgct gggacacctt tgtggaccac cagggatgtc      5880
ccttccagcc ctgggatgga ctagatgagc acagccaaga cctgagtggg aggctgcggg      5940
ccattctcca gaatcaggaa acaagcttg gcccgaaca aaaactcatc tcagaagagg        6000
atctgaatag cgccgtcgac catcatcatc atcatcattg agttttcgag acctagaaaa      6060
acatggagca atcacaagta gcaatacagc agctaacaat gctgcttgtg cctggctaga      6120
agcacaagag gaggaagagg tgggtttttcc agtcacacct caggtaccttt aagaccaat     6180 gacttacaag gcagctgtag atcttagcca cttttaaaa gaaaaggggg gactggaagg       6240
gctaattcac tcccaaagaa gacaagatat ccttgatctg tggatctacc acacacaagg      6300
ctacttccct gattggcaga actacacacc agggccaggg gtcagatatc cactgacctt      6360
tggatggtgc tacaagctag taccagttga gccagataag gtagaagagg ccaataaagg      6420
agagaacacc agcttgttac accctgtgag cctgcatgga atggatgacc ctgagagaga      6480
agtgttagag tggaggtttg acagccgcct agcatttcat cacgtggccc gagagctgca      6540
tccggagtac ttcaagaact gctgacatcg agcttgctac aagggacttt ccgctgggga      6600
ctttccaggg aggcgtggcc tgggcggac tggggagtgg cgagccctca gatgctgcat      6660
ataagcagct gctttttgcc tgtactgggt ctctctggtt agaccagatc tgagcctggg      6720
agctctctgg ctaactaggg aacccactgc ttaagcctca ataaagcttg ccttgagtgc      6780
ttcaagtagt gtgtgcccgt ctgttgtgtg actctggtaa ctagagatcc ctcagaccct      6840
tttagtcagt gtggaaaatc tctagc                                          6866
```

<210> SEQ ID NO 6  
<211> LENGTH: 9174  
<212> TYPE: DNA  
<213> ORGANISM: Artificial Sequence  
<220> FEATURE:  
<223> OTHER INFORMATION: Description of the sequence: a recombinant  
vector, D3P129D. D3P129D is one version of D3 vector that is  
constructed from a lentivirus backbone. D3P129D has elements and  
genes originated from HIV-1 and a mutant A3G gene, P129D.

<400> SEQUENCE: 6

```
tggaagggct aatttggtcc caaaaaagac aagagatcct tgatctgtgg atctaccaca      60
```

```
cacaaggcta cttccctgat tggcagaact acacaccagg gccagggatc agatatccac    120
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
tgagtgctca agtagtgtgt gcccgtctgt tgtgtgact ctggtaacta gagatccctc    600 agacccttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200
ctccaggggc aaatggtaca tcaggccata tcacctagaa ctttaaatgc atgggtaaaa    1260
gtagtagaag agaaggcttt cagcccagaa gtaataccca tgttttcagc attatcagaa    1320
ggagccaccc cacaagattt aaataccatg ctaaacacag tggggggaca tcaagcagcc    1380
atgcaaatgt taaaagagac catcaatgag gaagctgcag aatgggatag attgcatcca    1440
gtgcatgcag ggcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
agccctacca gcattctgga cataagacaa ggaccaaagg aacccttag agactatgta    1680 gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaattttt agggaagatc    2100 tggccttccc acaagggaag gccagggaat tttcttcaga gcagaccaga gccaacagcc    2160
ccaccagaag agagcttcag gtttggggaa gagacaacaa ctccctctca gaagcaggag    2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg ataggggaa    2400 ttggaggttt tatcaaagta ggacagtatg atcagatact catagaaatc tgcggacata    2460
```

-continued

```
aagctatagg tacagtatta gtaggaccta cacctgtcaa cataattgga agaaatctgt    2520
tgactcagat tggctgcact ttaaatttc ccattagtcc tattgagact gtaccagtaa     2580
aattaaagcc aggaatggat ggcccaaaag ttaaacaatg ccattgaca gaagaaaaaa     2640 taaaagcatt agtagaaatt tgtacagaaa tggaaaagga aggaaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagatttc tgggaagttc    2820
aattaggaat accacatcct gcagggttaa acagaaaaaa atcagtaaca gtactggatg    2880
tgggcgatgc atattttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aagggtgccc acactaatga tgtgaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaacttct atgtagatgg ggcagccaat agggaaacta    3900
aattaggaaa agcaggatat gtaactgaca gaggaagaca aaaagttgtc ccctaacgg     3960 acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaagaaaaa ttataggaca ggtaagagat caggctgaac    4740
atcttaagac agcagtacaa atggcagtat tcatccacaa ttttaaaaga aaaggggga    4800
```

```
ttgggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatggga ttggaagcca aataagaat tctgcaacaa     5160 ctgctgttta tccatttcag aattgggtgt cgacatagca gataggcgt tactcgacag     5220 aggagagcaa gaaatgggag cagtagatcc tagactagag ccctggaagc atccaggaag    5280
tcagcctaaa actgcttgta ccaattgcta ttgtaaaaag tgttgctttc attgccaagt    5340
ttgtttcatg acaaaagcct taggcatctc ctatggcagg aagaagcgga gacagcgacg    5400
aagagctcat cagaacagtc agactcatca agcttctcta tcaaagcagt aagtagtaca    5460
tgggcgcgcc catgtggcag gaagtaggaa agcaatgta tgcccctccc atcagtggac      5520
aaattagatg ttcatcaaat attactgggc tgctattaac aagagatggt ggtaataaca    5580
acaatgggtc cgagatcttc agacctggag gaggcgatat gagggacaat ggagaagtg     5640 aattatataa atataaagta gtaaaaattg aaccattagg agtagcaccc accaaggcaa    5700
agagaagagt ggtgcagaga gaaaaaagag cagtgggaat aggagctttg ttccttgggt    5760
tcttgggagc agcaggaagc actatgggct gcacgtcaat gacgctgacg gtacaggcca    5820
gacaattatt gtctgatata gtgcagcagc agaacaattt gctgagggct attgaggcgc    5880
aacagcatct gttgcaactc acagtctggg gcatcaaaca gctccaggca agaatcctgg    5940
ctgtggaaag atacctaaag gatcaacagc tcctggggat ttggggttgc tctggaaaac    6000
tcatttgcac cactgctgtg ccttggaatg ctagttggag taataaatct ctggaacaga    6060
tttggaataa catgacctgg atggagtggg acagagaaat taacaattac acaagcttaa    6120
tacactcctt aattgaagaa tcgcaaaacc agcaagaaaa gaatgaacaa gaattattgg    6180
aattagataa atgggcaagt ttgtggaatt ggtttaacat aacaaattgg ctgtggtata    6240
taaaattatt cataatgata gtaggaggct tggtaggttt aagaatagtt tttgctgtac    6300
tttctatagt gaatagagtt aggcagggat attcaccatt atcgtttcag acccacctcc    6360
caatcccgag gggacccgac aggcccgaag gaatagaaga agaaggtgga gagagagaca    6420
gagacagatc cattcgatta gtgaacggat ccttagcact tatctgggac gatctgcgga    6480
gcctgtgcct cttcagctac caccgcttga gagacttact cttgattgta cgaggattg    6540 tggaacttct gggacgcagg gggtgggaag ccctcaaata ttggtggaat ctcctacaat    6600
attggagtca ggagctaaag aatagtgctg ttagcttgct caatgccaca gccatagcag    6660
tagctgaggg gacagatagg gttatagaag tagtacaagg agcttgtaga gctattcgcc    6720
acatacctag aagaataaga cagggcttgg aaaggatttt gctataagat gggtggcgcg    6780
gcctaatagt aatcaattac ggggtcatta gttcatagcc catatatgga gttccgcgtt    6840
acataactta cggtaaatgg cccgcctggc tgaccgccca acgaccccg cccattgacg     6900 tcaataatga cgtatgttcc catagtaacg ccaatagga ctttccattg acgtcaatgg     6960
gtggagtatt tacggtaaac tgcccacttg gcagtacatc aagtgtatca tatgccaagt    7020
acgcccccta ttgacgtcaa tgacggtaaa tggcccgcct ggcattatgc ccagtacatg    7080
acctatgggg actttcctac ttggcagtac atctacggga tgaagcctca cttcagaaac    7140
acagtggagc gaatgtatcg agacacattc tcctacaact tttataatag acccatcctt    7200
```

```
tctcgtcgga ataccgtctg gctgtgctac gaagtgaaaa caaagggtcc ctcaaggccc    7260
cctttggacg caaagatctt tcgaggccag gtgtattccg aacttaagta ccacccagag    7320
atgagattct tccactggtt cagcaagtgg aggaagctgc atcgtgacca ggagtatgag    7380
gtcacctggt acatatcctg gagcccctgc acaaagtgta cagggatat ggccacgttc     7440 ctggccgagg acccgaaggt taccctgacc atcttcgttg cccgcctcta ctacttctgg    7500
gacgacgatt accaggaggc gcttcgcagc ctgtgtcaga aaagagacgg tccgcgtgcc    7560
accatgaaga tcatgaatta tgacgaattt cagcactgtt ggagcaagtt cgtgtacagc    7620
caaagagagc tatttgagcc ttggaataat ctgcctaaat attatatatt actgcacatc    7680
atgctggggg agattctcag acactcgatg gatccaccca cattcacttt caactttaac    7740
aatgaacctt gggtcagagg acggcatgag acttacctgt gttatgaggt ggagcgcatg    7800
cacaatgaca cctgggtcct gctgaaccag cgcaggggct ttctatgcaa ccaggctcca    7860
cataaacacg gtttccttga aggccgccat gcagagctgt gcttcctgga cgtgattccc    7920
ttttggaagc tggacctgga ccaggactac agggttacct gcttcacctc ctggagcccc    7980
tgcttcagct gtgcccagga aatggctaaa ttcatttcaa aaacaaaca cgtgagcctg      8040 tgcatcttca ctgcccgcat ctatgatgat caaggaagat gtcaggaggg gctgcgcacc    8100
ctggccgagg ctggggccaa aatttcaata atgacataca gtgaatttaa gcactgctgg    8160
gacacctttg tggaccacca gggatgtccc ttccagccct gggatggact agatgagcac    8220
agccaagacc tgagtgggag gctgcgggcc attctccaga atcaggaaaa caagcttggg    8280
cccgaacaaa aactcatctc agaagaggat ctgaatagcg ccgtcgacca tcatcatcat    8340
catcattgag ttttcgagac ctagaaaaac atggagcaat cacaagtagc aatacagcag    8400
ctaacaatgc tgcttgtgcc tggctagaag cacaagagga ggaagaggtg ggttttccag    8460
tcacacctca ggtacctta agaccaatga cttacaaggc agctgtagat cttagccact     8520
ttttaaaaga aaaggggggga ctggaagggc taattcactc ccaagaaga caagatatcc     8580 ttgatctgtg gatctaccac acacaaggct acttccctga ttggcagaac tacacaccag    8640
ggccaggggt cagatatcca ctgacctttg gatggtgcta caagctagta ccagttgagc    8700
cagataaggt agaagaggcc aataaaggag agaacaccag cttgttacac cctgtgagcc    8760
tgcatggaat ggatgaccct gagagagaag tgttagagtg gaggtttgac agccgcctag    8820
catttcatca cgtggcccga gagctgcatc cggagtactt caagaactgc tgacatcgag    8880
cttgctacaa gggactttcc gctggggact ttccaggag gcgtggcctg gcgggactg     8940 gggagtggcg agccctcaga tgctgcatat aagcagctgc tttttgcctg tactgggtct    9000
ctctggttag accagatctg agcctgggag ctctctggct aactagggaa cccactgctt    9060
aagcctcaat aaagcttgcc ttgagtgctt caagtagtgt gtgcccgtct gttgtgtgac    9120
tctggtaact agagatccct cagaccccttt tagtcagtgt ggaaaatctc tagc          9174
```

<210> SEQ ID NO 7
<211> LENGTH: 10514
<212> TYPE: DNA
<213> ORGANISM: Artificial Sequence
<220> FEATURE:
<223> OTHER INFORMATION: Description of the sequence: a recombinant
      vector, D3GFPP129D. D3GFPP129D is one version of the D3GFP vector
      that is constructed from a lentivirus backbone. D3GFPP129D has
      genes and elements originated from HIV-1, A3G P129D, and EGFP
      gene.

<400> SEQUENCE: 7

```
tggaagggct aatttggtcc caaaaaagac aagagatcct tgatctgtgg atctaccaca         60
cacaaggcta cttccctgat tggcagaact acacaccagg gccagggatc agatatccac        120
tgacctttgg atggtgcttc aagttagtac cagttgaacc agagcaagta gaagaggcca        180
aataaggaga gaagaacagc ttgttacacc ctatgagcca gcatgggatg gaggacccgg        240
agggagaagt attagtgtgg aagtttgaca gcctcctagc atttcgtcac atggcccgag        300
agctgcatcc ggagtactac aaagactgct gacatcgagc tttctacaag ggactttccg        360
ctggggactt tccagggagg tgtggcctgg gcgggactgg ggagtggcga gccctcagat        420
gctacatata agcagctgct ttttgcctgt actgggtctc tctggttaga ccagatctga        480
gcctgggagc tctctggcta actagggaac ccactgctta agcctcaata aagcttgcct        540
tgagtgctca agtagtgtg tgcccgtctg ttgtgtgact ctggtaacta gagatccctc         600
agacccttt agtcagtgtg gaaaatctct agcagtggcg cccgaacagg gacttgaaag        660
cgaaagtaaa gccagaggag atctctcgac gcaggactcg gcttgctgaa gcgcgcacgg        720
caagaggcga gggcggcga ctggtgagta cgccaaaaat tttgactagc ggaggctaga         780
aggagagaga tgggtgcgag agcgtcggta ttaagcgggg gagaattaga taaatgggaa        840
aaaattcggt taaggccagg gggaaagaaa caatataaac taaaacatat agtatgggca        900
agcagggagc tagaacgatt cgcagttaat cctggccttt tagagacatc agaaggctgt        960
agacaaatac tgggacagct acaaccatcc cttcagacag gatcagaaga acttagatca       1020
ttatataata caatagcagt cctctattgt gtgcatcaaa ggatagatgt aaaagacacc       1080
aaggaagcct tagataagat agaggaagag caaaacaaaa gtaagaaaaa ggcacagcaa       1140
gcagcagctg acacaggaaa caacagccag gtcagccaaa attaccctat agtgcagaac       1200
ctccaggggc aaatggtaca tcaggccata tcacctagaa cttaaatgc atgggtaaaa        1260
gtagtagaag agaaggcttt cagcccagaa gtaataccca tgttttcagc attatcagaa       1320
ggagccaccc cacaagattt aaataccatg ctaaacacag tggggggaca tcaagcagcc       1380
atgcaaatgt taaaagagac catcaatgag gaagctgcag aatgggatag attgcatcca       1440
gtgcatgcag ggcctattgc accaggccag atgagagaac caaggggaag tgacatagca       1500
ggaactacta gtacccttca ggaacaaata ggatggatga cacataatcc acctatccca       1560
gtaggagaaa tctataaaag atggataatc ctgggattaa ataaaatagt aagaatgtat       1620
agccctacca gcattctgga cataagacaa ggaccaaagg aacccttag agactatgta        1680
gaccgattct ataaaactct aagagccgag caagcttcac aagaggtaaa aaattggatg       1740
acagaaacct tgttggtcca aaatgcgaac ccagattgta agactatttt aaaagcattg       1800
ggaccaggag cgacactaga agaaatgatg acagcatgtc agggagtggg gggacccggc       1860
cataaagcaa gagttttggc tgaagcaatg agccaagtaa caaatccagc taccataatg       1920
atacagaaag gcaattttag gaaccaaaga aagactgtta agtgtttcaa ttgtggcaaa       1980
gaagggcaca tagccaaaaa ttgcagggcc cctaggaaaa agggctgttg gaaatgtgga       2040
aaggaaggac accaaatgaa agattgtact gagagacagg ctaattttt agggaagatc       2100
tggccttccc acaagggaag gccagggaat tttcttcaga gcagaccaga gccaacagcc       2160
ccaccagaag agagcttcag gtttggggaa gagacaacaa ctccctctca gaagcaggag       2220
ccgatagaca aggaactgta tcctttagct tccctcagat cactctttgg cagcgacccc       2280
tcgtcacaat aaagataggg gggcaattaa aggaagctct attagataca ggagcagatg       2340
```

```
atacagtatt agaagaaatg aatttgccag gaagatggaa accaaaaatg ataggggaa      2400 ttggaggttt tatcaaagta ggacagtatg atcagatact catagaaatc tgcggacata      2460
aagctatagg tacagtatta gtaggaccta cacctgtcaa cataattgga agaaatctgt      2520
tgactcagat tggctgcact ttaaattttc ccattagtcc tattgagact gtaccagtaa      2580
aattaaagcc aggaatggat ggcccaaaag ttaaacaatg gccattgaca gaagaaaaaa      2640
taaaagcatt agtagaaatt tgtacagaaa tggaaaagga aggaaaaatt tcaaaaattg      2700
ggcctgaaaa tccatacaat actccagtat ttgccataaa gaaaaaagac agtactaaat      2760
ggagaaaatt agtagatttc agagaactta ataagagaac tcaagatttc tgggaagttc      2820
aattaggaat accacatcct gcagggttaa aacagaaaaa atcagtaaca gtactggatg      2880
tgggcgatgc atatttttca gttcccttag ataaagactt caggaagtat actgcattta      2940
ccatacctag tataaacaat gagacaccag ggattagata tcagtacaat gtgcttccac      3000
agggatggaa aggatcacca gcaatattcc agtgtagcat gacaaaaatc ttagagcctt      3060
ttagaaaaca aaatccagac atagtcatct atcaatacat ggatgatttg tatgtaggat      3120
ctgacttaga aatagggcag catagaacaa aaatagagga actgagacaa catctgttga      3180 ggtgggggatt taccacacca gacaaaaaac atcagaaaga acctccattc ctttggatgg      3240
gttatgaact ccatcctgat aaatggacag tacagcctat agtgctgcca gaaaaggaca      3300
gctggactgt caatgacata cagaaattag tgggaaaatt gaattgggca agtcagattt      3360
atgcagggat taaagtaagg caattatgta aacttcttag gggaaccaaa gcactaacag      3420
aagtagtacc actaacagaa gaagcagagc tagaactggc agaaaacagg gagattctaa      3480
aagaaccggt acatggagtg tattatgacc catcaaaaga cttaatagca gaaatacaga      3540
agcaggggca aggccaatgg acatatcaaa tttatcaaga gccatttaaa aatctgaaaa      3600
caggaaaata tgcaagaatg aagggtgccc acactaatga tgtgaaacaa ttaacagagg      3660
cagtacaaaa aatagccaca gaaagcatag taatatgggg aaagactcct aaatttaaat      3720
tacccataca aaaggaaaca tgggaagcat ggtggacaga gtattggcaa gccacctgga      3780
ttcctgagtg ggagtttgtc aatacccctc ccttagtgaa gttatggtac cagttagaga      3840
aagaacccat aataggagca gaaacttttc tatgtagatg ggcagccaat agggaaacta      3900
aattaggaaa agcaggatat gtaactgaca gaggaagaca aaaagttgtc cccctaacgg      3960
acacaacaaa tcagaagact gagttacaag caattcatct agctttgcag gattcgggat      4020
tagaagtaaa catagtgaca gactcacaat atgcattggg aatcattcaa gcacaaccag      4080
ataagagtga atcagagtta gtcagtcaaa taatagagca gttaataaaa aaggaaaaag      4140
tctacctggc atgggtacca gcacacaaag gaattggagg aaatgaacaa gtagatgggt      4200
tggtcagtgc tggaatcagg aaagtactat ttttagatgg aatagataag gcccaagaag      4260
aacatgagaa atatcacagt aattggagag caatggctag tgattttaac ctaccacctg      4320
tagtagcaaa agaaatagta gccagctgtg ataaatgtca gctaaaaggg gaagccatgc      4380
atggacaagt agactgtagc ccaggaatat ggcagctaga ttgtacacat ttagaaggaa      4440
aagttatctt ggtagcagtt catgtagcca gtggatatat agaagcagaa gtaattccag      4500
cagagacagg gcaagaaaca gcatacttcc tcttaaaatt agcaggaaga tggccagtaa      4560
aaacagtaca tacagacaat ggcagcaatt tcaccagtac tacagttaag gccgcctgtt      4620
ggtgggcggg gatcaagcag gaatttggca ttccctacaa tccccaaagt caaggagtaa      4680
```

```
tagaatctat gaataaagaa ttaaagaaaa ttataggaca ggtaagagat caggctgaac   4740
atcttaagac agcagtacaa atggcagtat tcatccacaa ttttaaaaga aaagggggga   4800 ttgggggta cagtgcaggg gaaagaatag tagacataat agcaacagac atacaaacta    4860
aagaattaca aaacaaatt acaaaaattc aaaattttcg ggtttattac agggacagca    4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatggga ttggaagcca taataagaat tctgcaacaa   5160
ctgctgttta tccatttcag aattgggtgt cgacatagca gaataggcgt tactcgacag   5220
aggagagcaa gaaatggagc cagtagatcc tagactagag ccctggaagc atccaggaag   5280
tcagcctaaa actgcttgta ccaattgcta ttgtaaaaag tgttgctttc attgccaagt   5340
ttgtttcatg acaaaagcct taggcatctc ctatggcagg aagaagcgga gacagcgacg   5400
aagagctcat cagaacagtc agactcatca agcttctcta tcaaagcagt aagtagtaca   5460
tgggcgcgcc catgtggcag gaagtaggaa aagcaatgta tgcccctccc atcagtggac   5520
aaattagatg ttcatcaaat attactgggc tgctattaac aagagatggt ggtaataaca   5580
acaatgggtc cgagatcttc agacctggag gaggcgatat gagggacaat tggagaagtg   5640
aattatataa atataaagta gtaaaaattg aaccattagg agtagcaccc accaaggcaa   5700
agagaagagt ggtgcagaga gaaaaaagag cagtgggaat aggagctttg ttccttgggt   5760
tcttgggagc agcaggaagc actatgggct gcacgtcaat gacgctgacg gtacaggcca   5820
gacaattatt gtctgatata gtgcagcagc agaacaattt gctgagggct attgaggcgc   5880
aacagcatct gttgcaactc acagtctggg gcatcaaaca gctccaggca agaatcctgg   5940
ctgtggaaag atacctaaag gatcaacagc tcctggggat ttggggttgc tctggaaaac   6000
tcatttgcac cactgctgtg ccttggaatg ctagttggag taataaatct ctggaacaga   6060
tttggaataa catgacctgg atggagtggg acagagaaat taacaattac acaagcttaa   6120
tacactcctt aattgaagaa tcgcaaaacc agcaagaaaa gaatgaacaa gaattattgg   6180
aattagataa atgggcaagt ttgtggaatt ggtttaacat aacaaattgg ctgtggtata   6240
taaaattatt cataatgata gtaggaggct tggtaggttt aagaatagtt tttgctgtac   6300
tttctatagt gaatagagtt aggcagggat attcaccatt atcgtttcag acccacctcc   6360
caatcccgag gggacccgac aggcccgaag gaatagaaga agaaggtgga gagagagaca   6420
gagacagatc cattcgatta gtgaacggat ccttagcact tatctgggac gatctgcgga   6480
gcctgtgcct cttcagctac caccgcttga gagacttact cttgattgta acgaggattg   6540
tggaacttct gggacgcagg gggtgggaag ccctcaaata ttggtggaat ctcctacaat   6600
attggagtca ggagctaaag aatagtgctg ttagcttgct caatgccaca gccatagcag   6660
tagctgaggg gacagatagg gttatagaag tagtacaagg agcttgtaga gctattcgcc   6720
acatacctag aagaataaga cagggcttgg aaaggatttt gctataagat gggtggcgcg   6780
gcctaatagt aatcaattac ggggtcatta gttcatagcc catatatgga gttccgcgtt   6840
acataactta cggtaaatgg cccgcctggc tgaccgccca acgaccccg cccattgacg    6900 tcaataatga cgtatgttcc catagtaacg ccaatagga cttccattg acgtcaatgg     6960 gtggagtatt tacggtaaac tgcccacttg gcagtacatc aagtgtatca tatgccaagt   7020
acgcccccta ttgacgtcaa tgacggtaaa tggcccgcct ggcattatgc ccagtacatg   7080
```

```
accttatggg actttcctac ttggcagtac atctacggga tgaagcctca cttcagaaac    7140
acagtggagc gaatgtatcg agacacattc tcctacaact tttataatag acccatcctt    7200
tctcgtcgga ataccgtctg gctgtgctac gaagtgaaaa caaagggtcc ctcaaggccc    7260
cctttggacg caaagatctt tcgaggccag gtgtattccg aacttaagta ccacccagag    7320
atgagattct tccactggtt cagcaagtgg aggaagctgc atcgtgacca ggagtatgag    7380
gtcacctggt acatatcctg gagcccctgc acaaagtgta caagggatat ggccacgttc    7440
ctggccgagg acccgaaggt taccctgacc atcttcgttg cccgcctcta ctacttctgg    7500
gacgacgatt accaggaggc gcttcgcagc ctgtgtcaga aaagagacgg tccgcgtgcc    7560
accatgaaga tcatgaatta tgacgaattt cagcactgtt ggagcaagtt cgtgtacagc    7620
caaagagagc tatttgagcc ttggaataat ctgcctaaat attatatatt actgcacatc    7680
atgctggggg agattctcag acactcgatg gatccaccca cattcacttt caactttaac    7740
aatgaacctt gggtcagagg acggcatgag acttacctgt gttatgaggt ggagcgcatg    7800
cacaatgaca cctgggtcct gctgaaccag cgcaggggct ttctatgcaa ccaggctcca    7860
cataaacacg gtttccttga aggccgccat gcagagctgt gcttcctgga cgtgattccc    7920
ttttggaagc tggacctgga ccaggactac agggttacct gcttcacctc ctggagcccc    7980
tgcttcagct gtgcccagga aatggctaaa ttcatttcaa aaaacaaaca cgtgagcctg    8040
tgcatcttca ctgcccgcat ctatgatgat caaggaagat gtcaggaggg gctgcgcacc    8100
ctggccgagg ctggggccaa aatttcaata atgcatacaa gtgaatttaa gcactgctgg    8160
gacacctttg tggaccacca gggatgtccc ttccagccct gggatggact agatgagcac    8220
agccaagacc tgagtgggag gctgcgggcc attctccaga atcaggaaaa caagcttggg    8280
cccgaacaaa aactcatctc agaagaggat ctgaatagcg ccgtcgacca tcatcatcat    8340
catcattgag tttaaacgta gatgtaattc taacgttact ggccgaagcc gcttggaata    8400
aggccggtgt gcgtttgtct atatgttatt ttccaccata ttgccgtctt ttggcaatgt    8460
gagggcccgg aaacctggcc ctgtcttctt gacgagcatt cctaggggtc tttcccctct    8520
cgccaaagga atgcaaggtc tgttgaatgt cgtgaaggaa gcagttcctc tggaagcttc    8580
ttgaagacaa acaacgtctg tagcgaccct ttgcaggcag cggaaccccc cacctggcga    8640
caggtgcctc tgcggccaaa agccacgtgt ataagataca cctgcaaagg cggcacaacc    8700
ccagtgccac gttgtgagtt ggatagttgt ggaaagagtc aaatggctct cctcaagcgt    8760
attcaacaag ggctgaagg atgcccagaa ggtaccccat tgtatgggat ctgatctggg    8820
gcctcggtgc acatgcttta cgtgtgttta gtcgaggtta aaaaacgtct aggcccccg    8880 aaccacgggg acgtggtttt cctttgaaaa acacgatgat aatagcttgc cacaaccatg    8940
gggatccacc ggtcgccacc atggtgagca agggcgagga gctgttcacc ggggtggtgc    9000
ccatcctggt cgagctggac ggcgacgtaa acggccacaa gttcagcgtg tccggcgagg    9060
gcgagggcga tgccacctac ggcaagctga ccctgaagtt catctgcacc accggcaagc    9120
tgcccgtgcc ctggcccacc ctcgtggcca ccctgaccta cggcgtgcag tgcttcagcc    9180
gctaccccga ccacatgaag cagcacgact tcttcaagtc cgccatgccc gaaggctacg    9240
tccaggagcg caccatcttc ttcaaggacg acggcaacta caagacccgc gccgaggtga    9300
agttcgaggg cgacaccctg gtgaaccgca tcgagctgaa gggcatcgac ttcaaggagg    9360
acggcaacat cctggggcac aagctggagt acaactacaa cagccacaac gtctatatca    9420
```

```
tggccgacaa gcagaagaac ggcatcaagg tgaacttcaa gatccgccac aacatcgagg    9480
acggcagcgt gcagctcgcc gaccactacc agcagaacac ccccatcggc gacggccccg    9540
tgctgctgcc cgacaaccac tacctgagca cccagtccgc cctgagcaaa gaccccaacg    9600
agaagcgcga tcacatggtc ctgctggagt tcgtgaccgc cgccgggatc actctcggca    9660
tggacgagct gtacaagtaa agcggtcgcg actcgagacc tagaaaaaca tggagcaatc    9720
acaagtagca atacagcagc taacaatgct gcttgtgcct ggctagaagc acaagaggag    9780
gaagaggtgg gttttccagt cacacctcag gtacctttaa gaccaatgac ttacaaggca    9840
gctgtagatc ttagccactt tttaaaagaa agggggggac tggaagggct aattcactcc    9900
caaagaagac aagatatcct tgatctgtgg atctaccaca cacaaggcta cttccctgat    9960
tggcagaact acacaccagg gccagggatc agatatccac tgacctttgg atggtgctac   10020
aagctagtac cagttgagcc agataaggta gaagaggcca ataaaggaga gaacaccagc   10080
ttgttacacc ctgtgagcct gcatggaatg gatgaccctg agagagaagt gttagagtgg   10140
aggtttgaca gccgcctagc atttcatcac gtggcccgag agctgcatcc ggagtacttc   10200
aagaactgct gacatcgagc ttgctacaag ggactttccg ctggggactt tccagggagg   10260
cgtggcctgg gcgggactgg ggagtggcga gccctcagat gctgcatata agcagctgct   10320
ttttgcctgt actgggtctc tctggttaga ccagatctga gcctgggagc tctctggcta   10380
actagggaac ccactgctta agcctcaata aagcttgcct tgagtgcttc aagtagtgtg   10440
tgcccgtctg ttgtgtgact ctggtaacta gagatccctc agacccttt agtcagtgtg    10500 gaaaatctct agca                                                    10514

<210> SEQ ID NO 8
<211> LENGTH: 645
<212> TYPE: DNA
<213> ORGANISM: Artificial Sequence
<220> FEATURE:
<223> OTHER INFORMATION: Description of the sequence: an artificial
      nucleotide sequence of hsSIVmacVif, which encodes a protein with
      its amino acid sequence identical to that of viral infectivity
      factor of simian immunodeficiency virus, strain from Rhesus
      Macaque (SIVmacVif).
<220> FEATURE:
<221> NAME/KEY: exon
<222> LOCATION: (1)..(645)

<400> SEQUENCE: 8 atg gag gag gag aag cgc tgg atc gcc gta ccc acc tgg cgc atc ccc    48
Met Glu Glu Glu Lys Arg Trp Ile Ala Val Pro Thr Trp Arg Ile Pro
1               5                   10                  15 gag cgc ctg gag cgc tgg cac agc ctg atc aag tac ctg aag tac aag    96
Glu Arg Leu Glu Arg Trp His Ser Leu Ile Lys Tyr Leu Lys Tyr Lys
            20                  25                  30 acc aag gac ctg cag aag gta tgc tac gtg ccc cac ttc aag gtc ggc    144
Thr Lys Asp Leu Gln Lys Val Cys Tyr Val Pro His Phe Lys Val Gly
        35                  40                  45 tgg gcc tgg tgg acc tgc agc cgc gta atc ttc ccc ctg cag gag ggc    192
Trp Ala Trp Trp Thr Cys Ser Arg Val Ile Phe Pro Leu Gln Glu Gly
    50                  55                  60 agc cac ctg gag gta cag ggc tac tgg cac ctg acc cca gag cgc ggc    240
Ser His Leu Glu Val Gln Gly Tyr Trp His Leu Thr Pro Glu Arg Gly
65                  70                  75                  80 tgg ctg agc acc tac gcc gtg cgc atc acc tgg tac agc cgc aac ttc    288
Trp Leu Ser Thr Tyr Ala Val Arg Ile Thr Trp Tyr Ser Arg Asn Phe
                85                  90                  95
```

```
                                            -continued tgg acc gac gta acc cca gac tac gcc gac atc ctg ctg cac agc acc       336
Trp Thr Asp Val Thr Pro Asp Tyr Ala Asp Ile Leu Leu His Ser Thr
            100                 105                 110 tac ttc ccc tgc ttc acc gcc ggc gag gtg cgc cgc gcc atc cgc ggc       384
Tyr Phe Pro Cys Phe Thr Ala Gly Glu Val Arg Arg Ala Ile Arg Gly
        115                 120                 125 gag cag ctg ctg agc tgc tgc aag ttc ccc cgc gcc cac cgc tac cag       432
Glu Gln Leu Leu Ser Cys Cys Lys Phe Pro Arg Ala His Arg Tyr Gln
    130                 135                 140 gta ccc agc ctg cag tac ctg gcc ctg aag gta gta agc gac gtc cgc       480
Val Pro Ser Leu Gln Tyr Leu Ala Leu Lys Val Val Ser Asp Val Arg
145                 150                 155                 160 agc cag gga gag aat ccc acc tgg aag cag tgg aga cgc gac aac cgc       528
Ser Gln Gly Glu Asn Pro Thr Trp Lys Gln Trp Arg Arg Asp Asn Arg
                165                 170                 175 aga ggc ctg cgc atg gcc aag cag aac agc cgc ggc gac aag cag cgc       576
Arg Gly Leu Arg Met Ala Lys Gln Asn Ser Arg Gly Asp Lys Gln Arg
            180                 185                 190 ggc agc aag cca cct acc aag ggc gcc gac ttc ccc ggc ctg gcc aag       624
Gly Ser Lys Pro Pro Thr Lys Gly Ala Asp Phe Pro Gly Leu Ala Lys
        195                 200                 205 gtc cta ggc atc ctg gcc tga                                           645
Val Leu Gly Ile Leu Ala
    210
```

RECOMBINANT VECTOR AND USE IN GENE THERAPY

FIELD OF INVENTION

The present invention relates to a recombinant vector that is suitable for treating HIV infected individuals or preventing HIV infection, as well as methods of producing the same.

BACKGROUND OF INVENTION

Infection of Human immunodeficiency viruses (HIV includes HIV-1 and HIV-2)/Acquired immunodeficiency syndrome (AIDS) is a globe pandemic. HIV-1 and HIV-2 are retroviruses and human pathogens. They infect 38.6 million people worldwide. (UNAIDS. 2006 report on the global AIDS epidemic, ISBN 92 9 173511 6) In the United States, 1,039,000 to 1,185,000 people suffer from HIV infection, and the cumulative number of diagnoses of Acquired Immunodeficiency Syndrome (AIDS) patients through 2004 is 944,305. (CDC HIV/AIDS Surveillance Report: HIV Infection and AIDS in the United States, 2004).

HIV/AIDS is a major health problem in developing countries. Although HIV/AIDS epidemic is under control and the number of new AIDS patients has been stabilized in some developed countries since late 1990s, mainly due to education and antiretroviral treatments, HIV infection spreads quickly in many developing areas, such as in countries in Africa, east and southeast Asia. The new cases of HIV infection grow exponentially, threatening millions of lives in these regions. In some area, HIV infects a quart of the local population. That not only reduces the life expectancy of the population but also destroys social structure of these affected countries, undermining the stability of the region.

Treatment of HIV/AIDS has been an avid research topic since the discovery of HIV viruses in the early 80s. There are drugs available to treat HIV-1 infection. The Food and Drug Administration (FDA) approved the first antiretroviral drug, AZT, in 1987. Currently, twenty FDA-approved antiretroviral drugs and their combinations are available for treating HIV-1 infection. These drugs target different stages of viral replication. For example, Enfuvirtide (T20) is an attachment inhibitor which prevents HIV virus from fusing with T cell membrane, therefore, blocks HIV's entry to its target cell. Nucleoside reverse transcriptase inhibitors (NRTIs) are a group of drugs that inhibit reverse transcriptase, blocking the enzyme's function of copying viral RNA to DNA during HIV's reverse transcription. A well-known representative of NRTIs is zidovudine (AZT). Protease inhibitors (PIs) have been developed to disrupt formations of enzymes and structural proteins of HIV by inhibiting HIV protease. They block the HIV in protein glycosylation phase, rendering the HIV noninfectious. Another group of drugs are non-nucleoside reverse transcriptase inhibitors (NNRTIs) that also inhibit reverse transcriptase by binding to it and blocking the enzyme's function of synthesize viral DNA in the HIV reverse transcription phase.

Antiretroviral cocktails are combinations of antiretroviral drugs. By using these cocktail, doctors are able to reduce the HIV viral load to a very low level in peripheral blood of treated AIDS patients and relieve the symptoms of AIDS in these patients, meanwhile reduce the side effects of the antiretroviral drugs. These treatments successfully prolong the lives of AIDS patients.

Drug resistance of HIV is a major challenge in treatments of HIV infection and AIDS. Although these drug mentioned above show considerable effect on slowing down viral replication during treatments, emerging strains of HIV that are resistant to existing drugs continue to be one of the biggest challenges in effectively treating HIV infection. Quite a number of patients fail their antiretroviral therapies because of emerging of drug resistant strains of HIV. Emerging of the drug-resistant strains is due to the natural selection and the rapid turnover of HIV during the course of infection that contributes a high viral mutation rate makes the virus easy to escape the conventional antiviral treatment. Under these circumstances, incomplete viral suppression caused by insufficient drug potency, poor compliance and intrinsic pharmacological barriers provides fertile ground for drug-resistant strains to emerge, undermining the therapeutic management of HIV disease. Therefore, finding new therapeutic methods and targets has never been as important as it is now.

SUMMARY OF THE INVENTION

In order to overcome many of the disadvantages of antiretroviral treatments described above, there are disclosed herein recombinant viral vectors, cell lines carrying the recombinant viral vectors, methods of producing such vectors and establishing the vector-producing cell lines, as well as their use in gene therapy for HIV infected individuals or prevention of HIV infection.

In accordance with an embodiment of the present invention, provided is a recombinant vector for delivering A3G genes into human cells comprising (i) a gene expression block including an A3G gene selected from a wild type A3G gene represented by SEQ ID NO: 1 and a mutant A3G gene and (ii) a group of genes from a modified lentiviral vector including a lentiviral gag gene and lentiviral regions of packaging signal ($\psi$, psi), long-term repeats (LTRs), Rev responsive element (RRE), and primer binding site (PBS); wherein said A3G gene is operably linked to the packaging signal ($\psi$, psi), LTRs, RRE, and PBS.

In accordance with a more detailed aspect of the present invention, the mutant A3G gene of the recombinant vector is selected from the group of A3G genes consisting of a mutant A3G gene represented by SEQ ID NO: 2, a mutant SEQ ID NO: 2 substituted with A, G, R at position 128, a mutant A3G gene represented by SEQ ID NO: 3, a mutant SEQ ID NO: 3 substituted with A, G, F at position 129.

In accordance with another embodiment of the present invention, provided are mammalian cell lines transformed by the recombinant vector.

In accordance with at one embodiment of the present invention, methods for treating an individual with HIV infection, delaying the onset of AIDS, and treating AIDS using transformed T cells from blood and hematopoietic progenitor cells from bone marrow are provided. An exemplary method comprises the steps of: (a) withdrawing bone marrow from the HIV-infected individual, (b) isolating hematopoietic progenitor cells from the bone marrow, (c) cultivating and transforming the hematopoietic progenitor cells using a transforming agent including a therapeutically effective amount of the recombinant vector, (d) verifying the A3G expression in the transformed hematopoietic progenitor cells using DNA sequencing or immunoblotting analysis, and (e) transplanting the transformed hematopoietic progenitor cells back into the HIV-infected individual.

In accordance with another embodiment of the present invention, provided is a method for treating an individual with HIV infection, delaying the onset of AIDS, treating AIDS and preventing HIV infection, comprising administering a gene therapy agent comprising a therapeutically effective amount of the recombinant vector with at least one excipient for treating HIV infection to the individual in need thereof.

In accordance with another aspect of the present invention, provided is a method for constructing a vector-producing plasmid for the recombination vector comprising i) modifying a lentiviral vector by including lentiviral regions of packaging signal (ψ, psi), LTRs, RRE, and PBS, ii) preparing an A3G gene selected from a wild type A3G gene represented by SEQ ID NO: 1 and a mutant A3G gene, and iii) operably linking said A3G gene to the packaging signal (ψ, psi), LTRs, RRE, and PBS.

In accordance with yet another aspect of the present invention, provided is a method for producing the recombination vector comprising the steps of: a) preparing a vector-producing cell line, b) eliminating A3G proteins within the vector-producing cell line comprising expressing a lentiviral protein in the vector-producing cell line to degrade an A3G protein within the vector-producing cell line, c) infecting the vector-producing cell line by the recombinant vector, and d) expressing envelope proteins in the vector-producing cell line.

Other aspects and advantages of the present invention will become apparent from the following detailed description, taken in conjunction with the accompanying drawings, illustrating by way of example the principles of the present invention.

BRIEF DESCRIPTION OF THE DRAWINGS

FIG. 1 shows the life cycle of HIV with vif gene deleted or mutated from its genome (HIV ΔVif).

FIG. 2 shows the life cycle of HIV with wild type vif gene in its genome (HIV).

FIG. 3 shows the life cycle HIV with wild type vif gene (HIV), in the presence of recombinant viral vector that encodes a mutant A3G protein.

FIG. 4 shows a genomic structure of recombinant viral vector D3 min with a wild type or mutant A3G gene inserted and all lentiviral genes mutated or deleted. The vector also comprises cis-acting elements including lentiviral LTRs, packaging signal (psi), RRE, modified CMV promoter (mPcmv).

FIG. 5 shows a genomic structure of recombinant viral vector D3GFP that comprises lentiviral genes of gag, pol, tar and rev, a wild type or mutant A3G gene and green fluorescent protein (GFP) gene. The vector also comprises cis-acting elements including lentiviral LTRs, packaging signal (psi), RRE, modified CMV promoter (mPcmv) and internal ribosomal entry site (IRES).

FIG. 6 shows a genomic structure of recombinant viral vector D3 that includes lentiviral genes of gag, pol, tar and rev, a wild type or mutant A3G gene. The vector also comprises cis-acting elements including lentiviral LTRs, packaging signal (psi), RRE, modified CMV promoter (mPcmv).

FIG. 7 shows the genomic structure of a recombinant viral vector with deletions in gag, vif, vpr, vpu, env, and nef genes and a wild type or mutant A3G gene inserted in the gag open reading frame (ORF).

FIG. 8 shows the genomic structure of recombinant viral vector with deletions in vif, vpr, vpu, env, and nef genes and a wild type or mutant A3G gene inserted in vif ORF.

FIG. 9 shows a genomic structure of the recombinant viral vector with deletions in vif, vpr, vpu, env, and nef genes, and insertion of the A3G gene or the mutant A3G gene attached to a PCMV promoter in the open reading frame of vpr gene.

FIG. 10 shows a genomic structure of the recombinant viral vector with deletions in vif, vpr, vpu, env, and nef genes and insertion of the A3G gene or the mutant A3G gene that is attached to a wild type PCMV promoter in env region.

FIG. 11 shows the structure of vector-producing plasmid, pD3 min.

FIG. 12 shows the structure of vector-producing plasmid, pD3GFP.

FIG. 13 shows the structure of vector-producing plasmid, pD3.

FIG. 14 shows a method of making a recombinant viral vector with a wild type or mutant A3G gene inserted. Briefly, the recombinant vector D3 is harvested from 293T cells that are transiently transfected with the vector-producing plasmid, pD3, macaque simian immunodeficiency virus' Vif (SIVmacVif) expression vector, pSIVmacVif, and CCR5-tropic envelope expression vector, pCCR5env.

FIG. 15 shows a method of making a recombinant viral vector with a wild type or mutant A3G gene inserted. Briefly, 293T cells are transfected with pSIVmacVif. After selection, the 293T-macVif cell line that stably express SIVmac Vif is established. The 293T-macVif cell line is infected by D3-VSVg vector produced from 293T that is transiently co-transfected with pSIVmacVif, pD3 and vesicular stomatitis virus protein g expression plasmid, pCMV-VSVg. After infection, the cell lines that stably carry D3 vector (293T-macVif-D3) is selected. The final D3 vector is produced by transiently transfecting 293T-macVif-D3 cell line with CCR5-tropic envelope protein expression vector, pCCR5env. The final D3 vectors are harvested from the culture supernatant of this transiently transfected cell line by filtering through a 0.45 μm filter.

FIG. 16 shows a method of making a recombinant viral vector with a wild type or mutant A3G gene inserted. Briefly, 293T cells are transfected with pSIVmacVif. After selection, the 293T-macVif cell line that stably express SIVmac Vif is established. The 293T-macVif cell line is infected by D3-VSVg vector produced from 293T that is transiently co-transfected with pSIVmacVif, pD3 and vesicular stomatitis virus protein g expression plasmid, pCMV-VSVg. After infection, the cell lines that stably carry D3 vector (293T-macVif-D3) is selected. The final D3 vector is produced by transiently transfecting 293T-macVif-D3 cell line with CCR5-tropic envelope protein expression vector, pCCR5env. After transfection, the cell line that stably carries CCR5-tropic envelope protein, 293T-macVif-D3-AD8 is selected and established. The final D3 vectors are harvested from the culture supernatant of this cell line by filtering through a 0.45 μm filter.

FIG. 17 shows a method of making a recombinant viral vector with a wild type or mutant A3G gene inserted. Briefly, 293T cell line are co-transfected with pSIVmacVif and pCCR5env. After selection, the 293T-macVif-AD8 cell line is established. This cell line is transfected with pD3 and go through selection. After selection, the 293T-macVif-D3-AD8 is established. The final D3 vectors are harvested from the culture supernatant of this cell line by filtering through a 0.45 μm filter.

FIG. 18 shows a method of making a recombinant viral vector with a wild type or mutant A3G gene inserted. Briefly, 293T cell line are co-transfected with pSIVmacVif and pCCR5env. After selection, the 293T-macVif-AD8 cell line is established. The 293T-macVif cell line is infected by D3-VSVg vector produced from 293T that is transiently co-transfected with pSIVmacVif, pD3 and vesicular stomatitis virus protein g expression plasmid, pCMV-VSVg and go through selection. After selection, the 293T-macVif-D3-AD8 is established. The final D3 vectors are harvested from the culture supernatant of this cell line by filtering through a 0.45 µm filter.

DETAILED DESCRIPTION OF THE INVENTION

Definition

Figure 1:
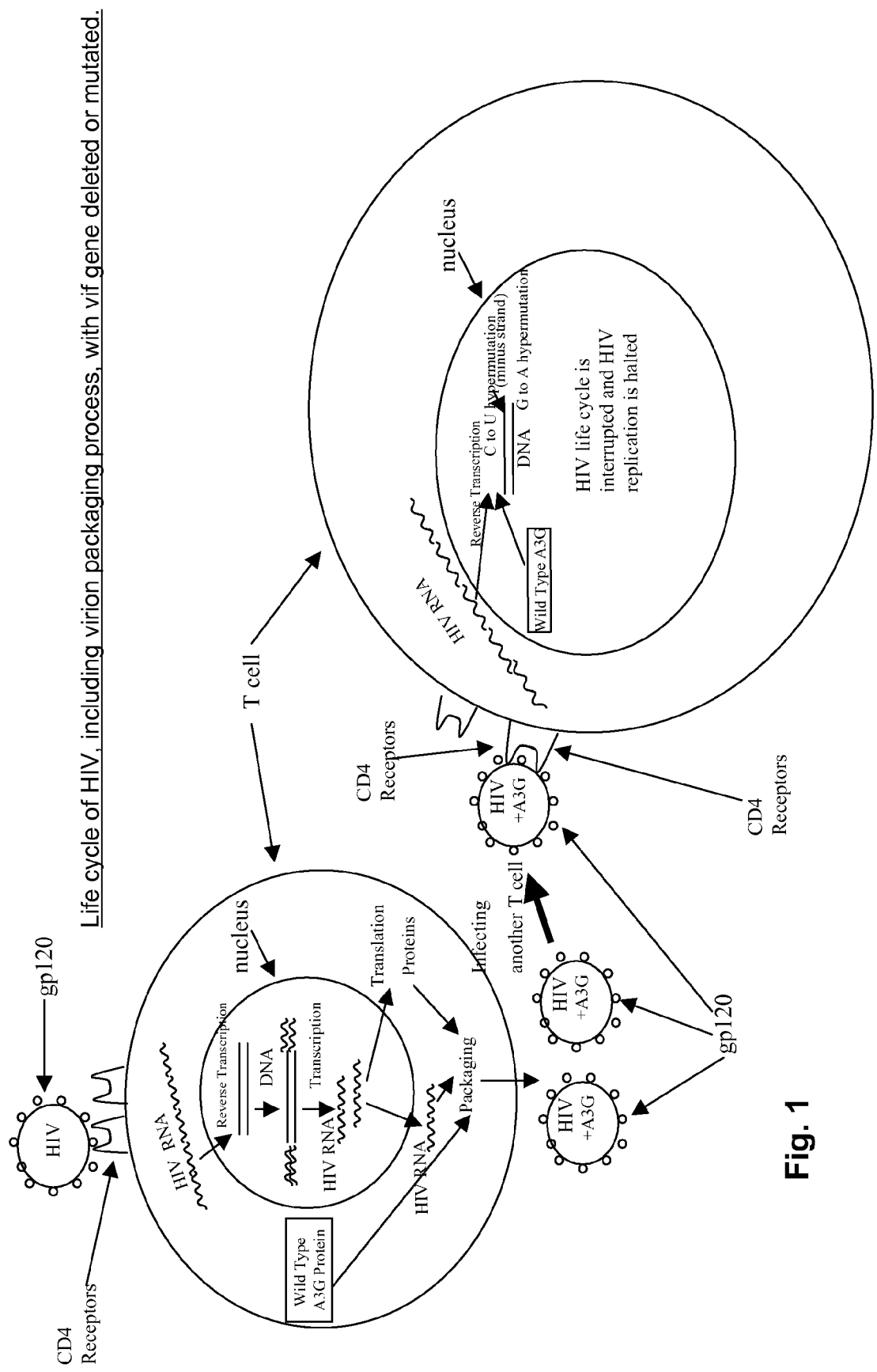

Before describing the invention in greater detail, the following definitions are set forth to illustrate and define the meaning and scope of the terms used to describe the invention herein.

The term "Element", when used herein, refers to untranslated region on genomic DNA or RNA of an organism or plasmid that is important to regulate processes such as, replication, package of genomic DNA or RNA, transcription, transportation of RNA and translation of the DNA or RNA, which are important to the life cycle of the organism.

The term "HIV-GFP", when used herein, refers to a Vif-deficient HIV-1 that express GFP as reporter.

The term "HIV", when used herein, refers to human immunodeficiency virus.

The term "HIV-1", when used herein, refers to human immunodeficiency virus type 1.

The term "HIV-2", when used herein, refers to human immunodeficiency virus type 2.

The term "HTLV", when used herein, refers to human T cell lymphoma virus.

The term "CMV", when used herein, refers to cytomegalovirus.

The term "SV40", when used herein, refers to simian virus 40.

The term "SIVagm", when used herein, refers to simian immunodeficiency virus, strain isolated from Africa Green Monkey.

The term "SIVmac", when used herein, refers to simian immunodeficiency virus, strain isolated from Rhesus Macaque.

The term "PBMC", when used herein, refers to human peripheral blood mononuclear cell.

The term "PBS", when used herein, refers to primer binding site, a region of retroviral genome that is complementary to and can be bound by tRNA to initiate reverse transcription.

The term "Polypeptide or peptide", when used herein, refers to polymerized amino acids or a protein.

The term "expression cassette or expression block", when used herein, refers to one or more genes and the sequences controlling the expression of these genes. Three components comprise an expression cassette: a promoter sequence or a sequence important for regulating expression, an open reading frame of a gene, and a 3' untranslated region that, in eukaryotes, usually contains a polyadenylation site. The cassette is a part of vector that is used to express genes that are desired in cells that are preferred.

The term "pseudotype a vector", when used herein, refers to express a particular envelope protein in vector-producing cells, so that vectors produced from these cells have that particular envelope on surface of the vector. The envelope protein can be from a retrovirus, or from viruses other than retroviruses, e.g., vesicular stomatitis virus (VSV). Preferably, the envelope protein of the pseudotyped vector is VSVg, which can infect a variety of cell types from a wide range of mammalian and non-mammalian species.

The term "Infection", when used herein (except in sections of Background and Gene Therapy Application), encompasses the process of retrovirus or retroviral vector entering the host cells, reverse transcribe its RNA genome into DNA transcript (viral DNA) and integrating the DNA transcript into host genome.

The term "Packaging signal", when used herein, encompasses the region of retroviral genomic RNA that is important for packaging the genomic RNA into that retroviral particles. In HIV-1, the region of package signal includes U5 region of the 5' LTR, untranslated region between the main splice donor site and gag initiation codon and first 635 base of gag-coding region.

The term "LTR (Long terminal repeat)", when used herein, encompasses the DNA sequence flanking the genome of integrated proviruses. It contains important regulatory regions, especially those for transcription initiation and polyadenylation.

The term "TAR (Target sequence for viral transactivation)", when used herein, encompasses the binding site for Tat protein and for cellular proteins; comprises approximately the first 45 nucleotides of the viral mRNAs in HIV-1 (or the first 100 nucleotides in HIV-2 and SIV.) TAR RNA forms a hairpin stem-loop structure with a side bulge; the bulge is necessary for Tat binding and function.

The term "RRE (Rev responsive element)", when used herein, encompasses an RNA element encoded within the env region of HIV-1. It comprises approximately 200 nucleotides (positions 7327 to 7530 from the start of transcription in HIV-1, spanning the border of gp120 and gp41). The RRE is necessary for Rev function; it contains a high affinity site for Rev; in all, approximately seven binding sites for Rev exist within the RRE RNA. Other lentiviruses (HIV-2, SIV, CAEV) have similar RRE elements in similar locations within env, while HTLVs have an analogous RNA element (RXRE) serving the same purpose within their LTR; RRE is the binding site for Rev protein, while RXRE is the binding site for Rex protein. RRE (and RXRE) form complex secondary structures, necessary for specific protein binding.

The term "GAG (group specific antigens)", when used herein, encompasses the genomic region encoding structural proteins. The term "Gag" refers the protein. The precursor is the p55 myristylated protein, which is processed to p17 (Matrix, Mass.), p24 (Capsid, Calif.), p7 (Nucleoaapsid, N.C.), and p6 proteins, by the viral protease. Gag associates with the plasma membrane where the virus assembly takes place. The 55 kDa Gag precursor is called assemblin to indicate its role in viral assembly.

The term "POL", when used herein, encompasses the genomic region encoding the viral enzymes protease, reverse transcriptase and integrase. The term "Pol" refers the protein. These enzymes are produced as a Gag-pol precursor polyprotein, which is processed by the viral protease; the Gag-pol precursor is produced by ribosome frameshifting at the C-terminus of gag.

The term "Env", when used herein, encompasses viral glycoproteins produced as a precursor (gp 160) which is processed to give a noncovalent complex of the external glycoprotein gp120 and the transmembrane glycoprotein gp41. The mature gp120-gp41 proteins are bound by non-covalent interactions and are associated as a trimer on the cell surface. A substantial amount of gp120 can be found released in the medium. gp120 contains the binding site for the CD4 receptor, and the seven transmembrane domain chemokine receptors that serve as co-receptors for HIV-1.

The term "Tat", when used herein, encompasses transactivator of HIV gene expression. One of two essential viral regulatory factors (Tat and Rev) for HIV gene expression. Two forms are known, Tat-1 exon (minor form) of 72 amino acids and Tat-2exon (major form) of 86 amino acids. Low levels of both proteins are found in persistently infected cells. Tat has been localized primarily in the nucleolus/nucleus by immunofluorescence. It acts by binding to the TAR RNA element and activating transcription initiation and/or elongation from the LTR promoter. It is the first eukaryotic transcription factor known to interact with RNA rather than DNA and may have similarities with prokaryotic antitermination factors. Extracellular Tat can be found and can be taken up by cells in culture.

The term "Rev", when used herein, encompasses the second necessary regulatory factor for HIV expression. A 19 kD phosphoprotein, localized primarily in the nucleolus/nucleus, Rev acts by binding to RRE and promoting the nuclear export, stabilization and utilization of the viral mRNAs containing RRE. Rev is considered the most functionally conserved regulatory protein of lentiviruses. Rev cycles rapidly between the nucleus and the cytoplasm.

The term "Vif", when used herein, encompasses viral infectivity factor, a basic protein of typically 23 kD. Promotes the infectivity but not the production of viral particles. In the absence of Vif the produced viral particles are defective, while the cell-to-cell transmission of virus is not affected significantly. Found in almost all lentiviruses, Vif is a cytoplasmic protein, existing in both a soluble cytosolic form and a membrane-associated form. The latter form of Vif is a peripheral membrane protein that is tightly associated with the cytoplasmic side of cellular membranes. Some recent observations suggest that Vif functions late in replication to modulate assembly, budding, and/or maturation the N-terminal half of Vif (N'-Vif) specifically interacts with viral protease.

The term "Vpr (viral protein R)", when used herein, encompasses a protein which is a 96-amino acid (14 kd) protein, and incorporated into the virion. It interacts with the p6 gag part of the Pr55 gag precursor. Vpr detected in the cell is localized to the nucleus. Proposed functions for Vpr include the targeting the nuclear import of preintegration complexes, cell growth arrest, transactivation of cellular genes, and induction of cellular differentiation. It is found in HIV-1, HIV-2, SIVmac and SIVmnd. It is homologous to the vpx protein.

The term "VPU (viral protein U)", when used herein, encompasses a gene that is unique to HIV-1 and SIVcpz, a close relative of HIV-1. The term "Vpu" refers the protein. There is no similar gene in HIV-2 or other SIVs. Vpu is a 16-kd (81-amino acid) type I integral membrane protein with at least two different biological functions: (a) degradation of CD4 in the endoplasmic reticulum, and (b) enhancement of virion release from the plasma membrane of HIV-1-infected cells. Env and Vpu are expressed from a bicistronic mRNA. Vpu probably possesses an N-terminal hydrophobic membrane anchor and a hydrophilic moiety. It is phosphorylated by casein kinase II at positions Ser52 and Ser56. Vpu is involved in Env maturation and is not found in the virion. Vpu has been found to increase susceptibility of HIV-1 infected cells to Fast killing.

The term "Nef", when used herein, encompasses a multifunctional 27-kd myristylated protein produced by an ORF located at the 30 end of the primate lentiviruses. Other forms of Nef are known, including nonmyristylated variants. Nef is predominantly cytoplasmic and associated with the plasma membrane via the myristyl residue linked to the conserved second amino acid (Gly). Nef has also been identified in the nucleus and found associated with the cytoskeleton in some experiments. One of the first HIV proteins to be produced in infected cells, it is the most immunogenic of the accessory proteins. The nef genes of HIV and SIV are dispensable in vitro, but are essential for efficient viral spread and disease progression in vivo. Nef is necessary for the maintenance of high virus loads and for the development of AIDS in macaques, and viruses with defective Nef have been detected in some HIV-1 infected long term survivors. Nef downregulates CD4, the primary viral receptor, and MHC class I molecules, and these functions map to different parts of the protein. Nef interacts with components of host cell signal transduction and clathrin-dependent protein sorting pathways. It increases viral infectivity. Nef contains PxxP motifs that bind to SH3 domains of a subset of Src kinases and are required for the enhanced growth of HIV but not for the downregulation of CD4.

The term "Vpx", when used herein, encompasses a virion protein of 12 kD found only in HIV-2/SIVmac/SIVsm and not in HIV-1 or SIVagm. This accessory gene is a homolog of HIV-1 vpr, and HIV-2/SIV carry both vpr and vpx. Vpx function in relation to xpr is not fully elucidated; both are incorporated into virions at levels comparable to gag proteins through interactions with Gag p6. Vpx is necessary for efficient replication of SIV in PBMCs. Progression to AIDS and death in SIV-infected animals can occur in the absence of Vpr or Vpx. Double mutant virus lacking both vpr and vpx was attenuated, whereas the single mutants were not, suggesting a redundancy in the function of Vpr and Vpx related to virus pathogenicity.

The term "Gag-Pol Precursor", when used herein, encompasses the viral protease (Pro), integrase (IN), RNase H, and reverse transcriptase (RT), which are always expressed within the context of a Gag-Pol fusion protein. The Gag-Pol precursor (p160) is generated by a ribosomal frame-shifting event, which is triggered by a specific cis-acting RNA motif (a heptanucleotide sequence followed by a short stem loop in the distal region of the Gag RNA).

The term "Pro (protease)", when used herein, encompasses the HIV-1 protease which is an aspartyl protease(16) that acts as a dimer. Protease activity is required for cleavage of the Gag and Gag-Pol polyprotein precursors during virion maturation as described previously.

The term "RT (reverse transcriptase)", when used herein, encompasses the pol gene encodes reverse transcriptase and the enzyme of reverse transcriptase. Pol has RNA-dependent and DNA-dependent polymerase activities. During the process of reverse transcription, the polymerase makes a double-stranded DNA copy of the dimer of single-stranded genomic RNA present in the virion.

The term "Integrase (IN)", when used herein, encompasses the IN protein mediates the insertion of the HIV proviral DNA into the genomic DNA of an infected cell. This process is mediated by three distinct functions of IN. First, an exonuclease activity trims two nucleotides from each 3' end of the linear viral DNA duplex. Then, a double-stranded endonuclease activity cleaves the host DNA at the integration site.

Finally, a ligase activity generates a single covalent linkage at each end of the proviral DNA.

The term "Env", when used herein, encompasses the 160 kD Env (gp160) is expressed from singly spliced mRNA. First synthesized in the endoplasmic reticulum, Env migrates through the Golgi complex where it undergoes glycosylation with the addition of 25 to 30 complex N-linked carbohydrate side chains that are added at asparagine residues. Env glycosylation is required for infectivity.

The term "Apolipoprotein B mRNA-editing enzyme-catalytic polypeptide-like 3G (A3G)", when used herein, encompasses Apolipoprotein B mRNA-editing enzyme-catalytic polypeptide-like 3G (A3G). It is first identified as CEM15, and is a host cellular protein with a broad antiviral activity. The amino acid residue at position 128 of the sequence of wild type A3G is Aspartate (Asp, D), and the amino acid residue at position of the sequence of wild type A3G is Proline (Pro, P). In this invention, these residues at position 128 and position 129 undergo substitute mutations respectively, resulting in mutant A3Gs. A3G inhibits infectivity of a wide variety of retroviruses by deaminating deoxycytidine (dC) into deoxyuridine (dU) in newly synthesized minus strand DNA, resulting in G-to-A hypermutation of the viral plus strand DNA. The A3G gene is a member of the cytidine deaminase gene family. It is one of seven related genes or pseudogenes found in a cluster, thought to result from gene duplication, on chromosome 22. It is thought that the proteins may be RNA editing enzymes and have roles in growth or cell cycle control. The protein encoded by this gene has been found to be a specific inhibitor of human immunodeficiency virus-1 (HIV-1) and some simian immunodeficiency viruses infectivities in the absence of their viral infectivity factors (Vifs).

"Recombinant" when used herein, refers to a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

A "vector," as used herein, refers to a recombinant plasmid or virus that comprises a polynucleotide to be delivered into a host cell, either in vitro or in vivo. The polynucleotide to be delivered, sometimes referred to as a "heterologous sequence, ""target polynucleotide," "transgene," or "gene of interest" can comprise a sequence of interest in gene therapy (such as a gene encoding a protein or RNA transcript, such as an antisense transcript or a ribozyme, of therapeutic interest) and/or a selectable or detectable marker.

A "recombinant viral vector or recombinant vector" refers to a vector comprising one or more heterologous sequences (i.e., polynucleotide sequence from multiple origins).

A "promoter," as used herein, refers to a nucleotide sequence that directs the transcription of a gene or coding sequence to which it is operably linked.

"Operably linked" when used herein, refers to an arrangement of two or more components, wherein the components so described are in a relationship permitting them to function in a coordinated manner. Aspects of the transcription process include, but are not limited to, initiation, elongation, attenuation and termination. An operably linked transcriptional regulatory sequence is generally joined in cis with the coding sequence, but it is not necessarily directly adjacent to it.

A "replicon" refers to a polynucleotide comprising an origin of replication which allows for replication of the polynucleotide in an appropriate host cell. Examples of replicons include viruses, episomes (including plasmids), as well as chromosomes (such as nuclear or mitochondrial chromosomes).

A "replication origin" is a nucleotide sequence involved in one or more aspects of initiation of DNA replication, such as, for example, binding of replication initiation factors to their binding sites, unwinding of the DNA duplex, primer formation, and/or template-directed synthesis of a complementary strand.

"Packaging" refers to a series of subcellular events that results in the assembly of viruses or vectors and encapsidation of viral or vector genomic RNA or DNA. Thus, when a suitable vector is introduced into a packaging cell line under appropriate conditions, it can be assembled into a viral like particle.

"Transduction" is the introduction of an exogenous gene into a cell by viral infection that results expression the exogenous gene in the cell, wherein the exogenous gene is part of a recombinant viral genome.

A "host cell" is a cell which has been or can be a recipient for a vector(s) of this invention and the progeny thereof. The progeny may not be necessarily be completely identical (in morphology or in genomic of total DNA complement) to the original parent cell due to-natural, accidental, or deliberate mutation. Host cells are preferably eukaryotic cells, preferably mammalian cells, and most preferably human cells.

A "gene product" is a product encoded by a nucleic acid sequence, preferably a DNA sequence, and can be RNA or protein. Examples of RNA gene products include mRNA, rRNA, tRNA, structural RNA, catalytic RNA and ribozymes. Examples of protein gene products, encoded by way of a mRNA intermediate, include structural proteins and enzymes.

"Expression" includes transcription and/or translation. Methods of detecting transcription, such as Northern analysis, and translation, such as Western analysis or ELISA, are well known in the art. These methods also permit measuring differing levels of transcription and/or translation, whether that difference is between or among different vectors, different times, different host cells, etc.

"Polynucleotide" refers to a polymeric form of nucleotides of any length. Polynucleotides can comprise ribonucleotides, deoxyribonucleotides, analogs thereof, or any combination of the aforementioned. The term includes single-, double- and triple-stranded nucleic acids, as well as higher order structures, such as quartets. It also includes modified polynucleotides such as methylated or capped polynucleotides, and polynucleotide analogues, such as polyamide (peptide) nucleic acids. Polynucleotides can be linear, branched or circular molecules. A linear polynucleotide has two termini; in the case of a single-stranded polynucleotide, these can be characterized as a 5' terminus and a 3' terminus.

An "effective amount" is an amount sufficient to effect beneficial or desired results, including clinical results. An effective amount can be administered in one or more administrations. In terms of a disease state, an effective amount is an amount sufficient to ameliorate, stabilize, or delay development of a disease.

"Lentiviral vectors," as used herein, refer to vectors that are modified from lentiviruses. Lentivirus is genus of the family of retrovirae consisting of non-oncogenic retroviruses that produce multi-organ diseases characterized by long incubation periods and persistent infection. Lentiviruses are unique in that they contain open reading frames (ORFs) between the pol and env genes and in the 3' env region. The most commonly used lentiviral vector is based on human immunodeficiency virus HIV-1. Lentiviral vectors are packaged using a 3 or 4-plasmid based system in which 4 HIV accessory genes, vpr, vpu, nef, and vif have been deleted to greatly increase safety of the vectors.

"Transfection", as used herein, refers to introduction of foreign DNA or RNA into host cells, resulting expression of the genes coded by the DNA or RNA.

The term "provirus", when used herein, encompasses a status wherein the genome of an animal virus integrated (by crossing over) into the chromosome of the host cell, and thus replicated in all of its daughter cells. It can be activated, spontaneously or by induction, to produce a complete virus; it can also cause transformation of the host cell.

"virion", as used herein, refers to the complete viral particle, found extracellularly and capable of infecting a living cell; it comprises the nucleoid (genetic material) and the capsid. It is also called viral particle.

"Virus", as used herein, refers to a group of minute infectious agents, with certain exceptions (e.g., poxviruses) not resolved in the light microscope, and characterized by a lack of independent metabolism and by the ability to replicate only within living host cells. Like living organisms, they are able to reproduce with genetic continuity and the possibility of mutation. They range from 200-300 nm to 15 nm in size and are morphologically heterogeneous, occurring as rod-shaped, spherical, or polyhedral, and tadpole-shaped forms; masses of the spherical or polyhedral forms may be made up of orderly arrays, to give a crystalline structure. The individual particle, or virion, consists of nucleic acid (the nucleoid), DNA or RNA (but not both) and a protein shell, or capsid, which contains and protects the nucleic acid and which may be multilayered.

"Budding", as used herein, refers to a method of release of virus from a cell after replication has taken place: viral protein associates itself with an area of cell membrane, which forms a coat or envelope around the virus; some cellular proteins in the area of budding are replaced by virus-coded proteins.

"Wild-type", as used herein, refers to the strain used as a standard for a given species or variety of organism, usually presumed to be the type found in nature. Also refers to a gene that determines a standard phenotypic trait.

"Mutation", as used herein, refers to a process in which the loss, gain, or exchange of genetic material has resulted in a permanent transmissible change in function. Such a gene may have become practically inactive (amorph), may act to antagonize or inhibit normal activity (antimorph), may act to increase normal activity (hypermorph), or may show only a slight reduction in its effectiveness (leaky gene or hypomorph).

"Mutant", as used herein, refers to a permanent transmissible change in the genetic material, usually in a single gene. Also refers to an individual exhibiting such a change in form, quality, or some other characteristic.

"Nucleotide sequence", as used herein, refers to a sequence of nucleic acid found in the chromosomes of living cells and viruses that play a central role in the storage and replication of hereditary information and in the expression of this information through protein synthesis. Nucleic acid molecules are complex chains of varying length. The two chief types of nucleic acids are DNA (deoxyribonucleic acid), which carries the hereditary information from generation to generation, and RNA (ribonucleic acid), which delivers the instructions coded in this information to the cell's protein manufacturing sites. The sequence of purines and pyrimidines (bases)-adenine (A), guanine (G), cytosine (C), and either thymine (T; in DNA) or uracil (U; in RNA)-in the nucleotides, in groups of three (triplets, or codons), constitutes the genetic code.

"DNA (deoxyribonucleic acid)", as used herein, refers to a molecule which chemical and physical properties suit for both replication and transfer of genetic information. Each DNA molecule is a long two-stranded chain. The strands are made up of subunits called nucleotides, each containing a sugar (deoxyribose), a phosphate group, and one of four nitrogenous bases, adenine, guanine, thymine, and cytosine, denoted A, G, T, and C, respectively. A given strand contains nucleotides bearing each of these four. The information carried by a given gene is coded in the sequence in which the nucleotides bearing different bases occur along the strand. These nucleotide sequences determine the sequences of amino acids in the polypeptide chain of the protein specified by that gene.

"RNA (ribonucleic acid) and Protein Synthesis", as used herein, refers to a molecule and a synthesis process which the genetic information is carried to the protein-synthesizing machinery of the cell in the cytoplasm. One form of RNA mediates this process. RNA is similar to DNA, but contains the sugar ribose instead of deoxyribose and the base uracil (U) instead of thymine. To initiate the process of information transfer, one strand of the double-stranded DNA chain serves as a template for the synthesis of a single strand of RNA that is complementary to the DNA strand (e.g., the DNA sequence AGTC . . . will specify an RNA sequence UCAG . . . ). This process is called transcription and is mediated by enzymes. The newly synthesized RNA, called messenger RNA, or mRNA, moves quickly to bodies in the cytoplasm called ribosomes, which are composed of two particles made of protein bound to ribosomal RNA, or rRNA. Each ribosome is the site of synthesis of a polypeptide chain. Several ribosomes attach to a single mRNA so that many polypeptide chains are synthesized from the same mRNA; each cluster of an mRNA and ribosomes is called a polyribosome or polysome. The nucleotide sequence of the mRNA is translated into the amino acid sequence of a protein by adaptor molecules composed of a third type of RNA called transfer RNA, or tRNA. There are many different species of tRNA, with each species binding one of 20 amino acids. In protein synthesis, a nucleotide sequence along the mRNA does not specify an amino acid directly; rather, it specifies a particular species of tRNA. For example, in coding for the amino acid tyrosine, a nucleotide sequence of mRNA is complementary to a portion of a tyrosine-tRNA molecule. As each specified tRNA associates with its complementary space on the mRNA, the amino acid is added onto the lengthening protein chain and the tRNA is released. When the protein chain is complete, it is released from the ribosome. The particular sequence of amino acids in each polypeptide chain is determined by the genetic code. Starting at one end of the mRNA strand, each 3-nucleotide sequence, or codon, specifies, via complementary tRNA sequences, one amino acid, and the series of such codons in the mRNA specifies a polypeptide chain. Although a "vocabulary" of 64 words, or specifications, is theoretically possible with 4 different nucleotides taken three at a time, there are only 20 amino acids to be specified. However, several triplets may code for the same amino acid. In addition, there are some codons that do not code for amino acids but code for polypeptide chain initiation and polypeptide chain termination. The code is also nonoverlapping; i.e., a nucleotide in one codon is never part of either adjacent codon. The code seems to be universal in all living organisms.

"Gene", as used herein, is defined by intervals along one of the DNA molecules. The location of the gene is called the locus.

"Gene disorder or genetic disorder", as used herein, refers to an abnormal gene which may code for an abnormal protein or for an abnormal amount of a normal protein.

"Transient transfection or transfection", as used herein, refers to a process that foreign DNA is introduced into eukaryotic cells. Experimentally, this is most often done as an instance of transient transfection, in which the transfected gene is expressed only transiently, that is, in only the cell to which it was originally inserted and only for a short period of time.

"Insertion or insert mutation", as used herein, refers to inserting elements are mobile genetic elements that insert into chromosomal sequences, often disrupting genes, add one or more extra nucleotides into the DNA. Most insertions in a gene can cause a shift in the reading frame (frameshift) or alter splicing of the mRNA, both of which can significantly alter the gene product. Insertions can be reverted by excision of the transposable element.

"Deletion or delete mutation", as used herein, refers to deleting remove one or more nucleotides from the DNA. Like insertions, these mutations can alter the reading frame of the gene. They are irreversible.

"Substitution or substitute mutation", as used herein, in the case of polynucleotide sequence, refers to replacing one nucleotide with one that is different from the replaced one. For example, an adenosine (A) is replaced by either guanosine (G) or cytidine (C) or thymidine (T) or uridine (U). Substitution mutations in a polynucleotide sequence don't alter the open reading frame of that polynucleotide sequence. In the case of protein, refers to replacing one amino acid in a polypeptide or protein with amino acid that is different from the replaced one. For example, the P129D substitute mutation of A3G refers to substitution of proline (Pro, P) at position 129 of A3G with Aspartate (Asp, D).

"Genome", as used herein, refers to the complete gene complement of an organism, contained in a set of chromosomes in eukaryotes, a single chromosome in bacteria, or a DNA or RNA molecule in viruses. Or, the full set of genes in an individual, either haploid (the set derived from one parent) or diploid (the double set, derived from both parents).

"Restriction enzyme", as used herein, refers to an endonuclease that hydrolyzes deoxyribonucleic acid, cleaving it at an individual site of a specific base pattern. Thus, the enzyme degrades DNA foreign to a cell but spares the cell's own DNA, which is protected by methylation at the recognition site. Restriction endonucleases isolated from bacterial sources are used extensively for sequencing of DNA and recombinant technology.

"Somatic cell", as used herein, refers to a cell that is in final stage of differentiation and is not destined to become a gamete; a cell whose genes cannot be passed on to future generations.

"Stem cells", as used herein, refers to the cells are different from other cells of the body in that they have the ability to differentiate into other cell/tissue types, such as bone marrow stem cells. This ability allows them to replace cells that have died. With this ability, they have been used to replace defective cells/tissues in patients who have certain diseases or defects.

"Ex vivo", as used herein, refers to an artificial environment outside the living organism.

"In vivo", as used herein, refers to an environment in the living organism.

"In vitro", as used herein, refers to an experimental situation outside the organism.

"RNA polymerase II (RNAP II)", as used herein, refers to a multisubunit enzyme responsible for transcription of protein coding genes in eukaryotes. The phosphorylation state of the C-terminal domain (CTD) of the largest RNAP II subunit plays an important role in the regulation of transcript elongation. The elongation efficiency of RNAP II is regulated at least in part by dedicated protein kinases and phosphatases that establish the level of CTD phosphorylation. Two forms of RNAP II can be found in all eukaryotes. The form containing the phosphorylated CTD is called RNAP IIO. A second form contains an unphosphorylated CTD and is known as RNAP IIA. RNAP IIO catalyzes transcript elongation, while completion of the transcription cycle is dependent on dephosphorylation of RNAP IIO.

"Reverse transcriptase", as used herein, refers to an enzyme used by retroviruses to form a complementary DNA sequence (cDNA) from an RNA template—usually the genome of the retrovirus. The enzyme then performs a complimentary template of the cDNA strand such that a double stranded DNA molecule is formed. This double stranded DNA molecule is then inserted into the chromosome of the host cell which has been infected by the retrovirus. Reverse transcriptase is one of the key components that HIV uses to mount its attack.

"Open reading frame (ORF)", as used herein, refers to a portion of an organism's genome which contains a sequence of bases that could potentially encode a protein. In a gene, ORFs are located between the start-code sequence (initiation codon) and the stop-code sequence (termination codon). ORFs are usually encountered when sifting through pieces of DNA while trying to locate a gene. Since there exist variations in the start-code sequence of organisms with altered genetic code, the ORF will be identified differently. A typical ORF finder will employ algorithms based on existing genetic codes (including the altered ones) and all possible reading frames.

"Hypermutation", as used herein, refers to that retroviral provirus is dubbed a "hypermutant" if it undergoes an unordinary amount of mutations. Hypermutation usually results in the production of replication-incompetent virus due to the introduction of new stop codons. Hypermutation is thought to be caused by a host cellular defense mechanism that induces mutations in reverse transcribed nascent retroviral DNA. Host lymphocytes express 2 proteins of the apolipoprotein B mRNA editing complex family, A3F and A3G. These enzymes have slightly different substrate specificities, but both produce G to A transitions. The HIV Vif protein blocks this process. When Vif is defective, hypermutation is the result.

"Internal ribosome entry site (IRES)", as used herein, refers to a nucleotide sequence that allows for translation initiation in the middle of a messenger RNA (mRNA) sequence as part of the greater process of protein synthesis. IRES are located in the 5'UTR of RNA viruses and allow translation of the RNAs in a cap-independent manner.

"Transformation", as used herein, refers to a process of introducing of DNA into organisms (cells) by artificial means. This process involves the use of a vector or plasmid DNA. Sequences of DNA can be spliced into vectors or plasmids, allowing them to be transferred into organisms (cells).

"D128A", as used herein, refers to D128A substitute mutation of A3G, in which amino acid residue Aspartate (Asp, D) at position 128 of the sequence of wild type A3G is substituted by Alanine (Ala, A), resulting in mutant A3G D128A.

"D128G", as used herein, refers to D128G substitute mutation of A3G, in which amino acid residue Aspartate (Asp, D) at position 128 of the sequence of wild type A3G is substituted by Glycine (Gly, G), resulting in mutant A3G D128G.

"D128R", as used herein, refers to D128R substitute mutation of A3G, in which amino acid residue Aspartate (Asp, D) at position 128 of the sequence of wild type A3G is substituted by Arginine (Arg, R), resulting in mutant A3G D128R.

"D128K", as used herein, refers to D128K substitute mutation of A3G, in which amino acid residue Aspartate (Asp, D) at position 128 of the sequence of wild type A3G is substituted by Lysine (Lys, K), resulting in mutant A3G D128K. D128K substitute mutation is one of the preferred embodiments of the invention.

"P129A", as used herein, refers to P129A substitute mutation of A3G, in which amino acid residue Proline (Pro, P) at position 129 of the sequence of wild type A3G is substituted by Alanine (Ala, A), resulting in mutant A3G P129A.

"P129G", as used herein, refers to P129G substitute mutation of A3G, in which amino acid residue Proline (Pro, P) at position 129 of the sequence of wild type A3G is substituted by Glycine (Gly, G), resulting in mutant A3G P129G.

"P129F", as used herein, refers to P129F substitute mutation of A3G, in which amino acid residue Proline (Pro, P) at position 129 of the sequence of wild type A3G is substituted by Phenylalanine (Phe, F), resulting in mutant A3G P129F.

"P129D", as used herein, refers to P129D substitute mutation of A3G, in which amino acid residue Proline (Pro, P) at position 129 of the sequence of wild type A3G is substituted by Aspartate (Asp, D), resulting in mutant A3G P129D. P129D substitute mutation is one of the preferred embodiments of the invention.

Gene Therapy Against HIV Infection

Gene therapy can be defined as a treatment to correct a patient's genetic expressions that are responsible for his/her disease by inserting or deleting certain nucleic acids sequence from the genome, therefore alters the genetic expression(s) of the cells in treated patients for the purpose of targeting the disease at the origin. In order to fulfill the task of manipulating the gene expression, a special vector should be designed and used as a delivery vehicle to carry a DNA molecule encoded a specific gene into the nucleus of the targeted cells.

The vector disclosed in this application is used to deliver an antiretroviral gene into human cells to inhibit HIV replication, which can lead to the development of new gene therapy methods for HIV infection and AIDS.

Advantages and features of the present invention will be better appreciated by understanding the replication cycle of viruses, particularly, the replication cycle of retroviruses.

Figure 2:
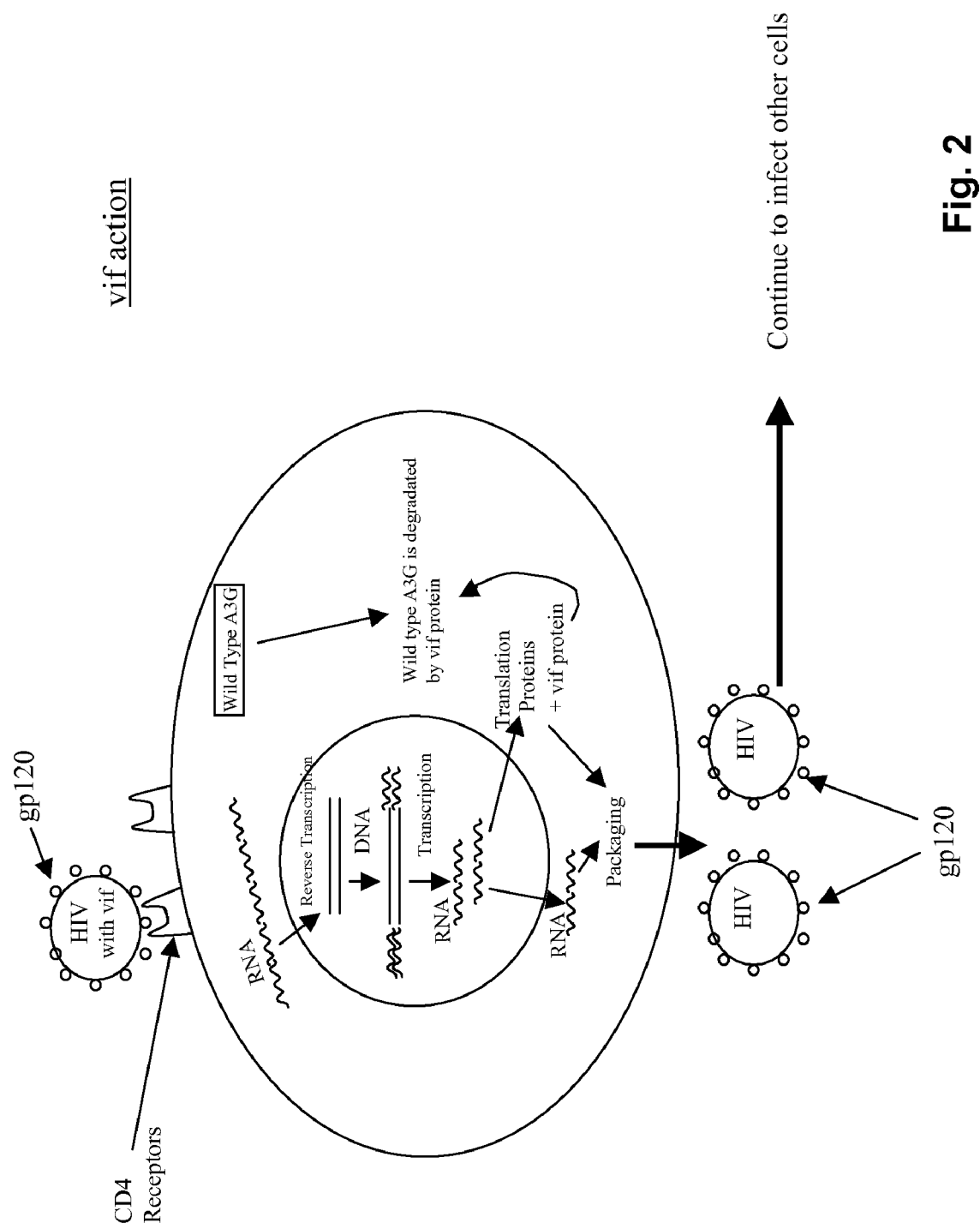
Figure 3:
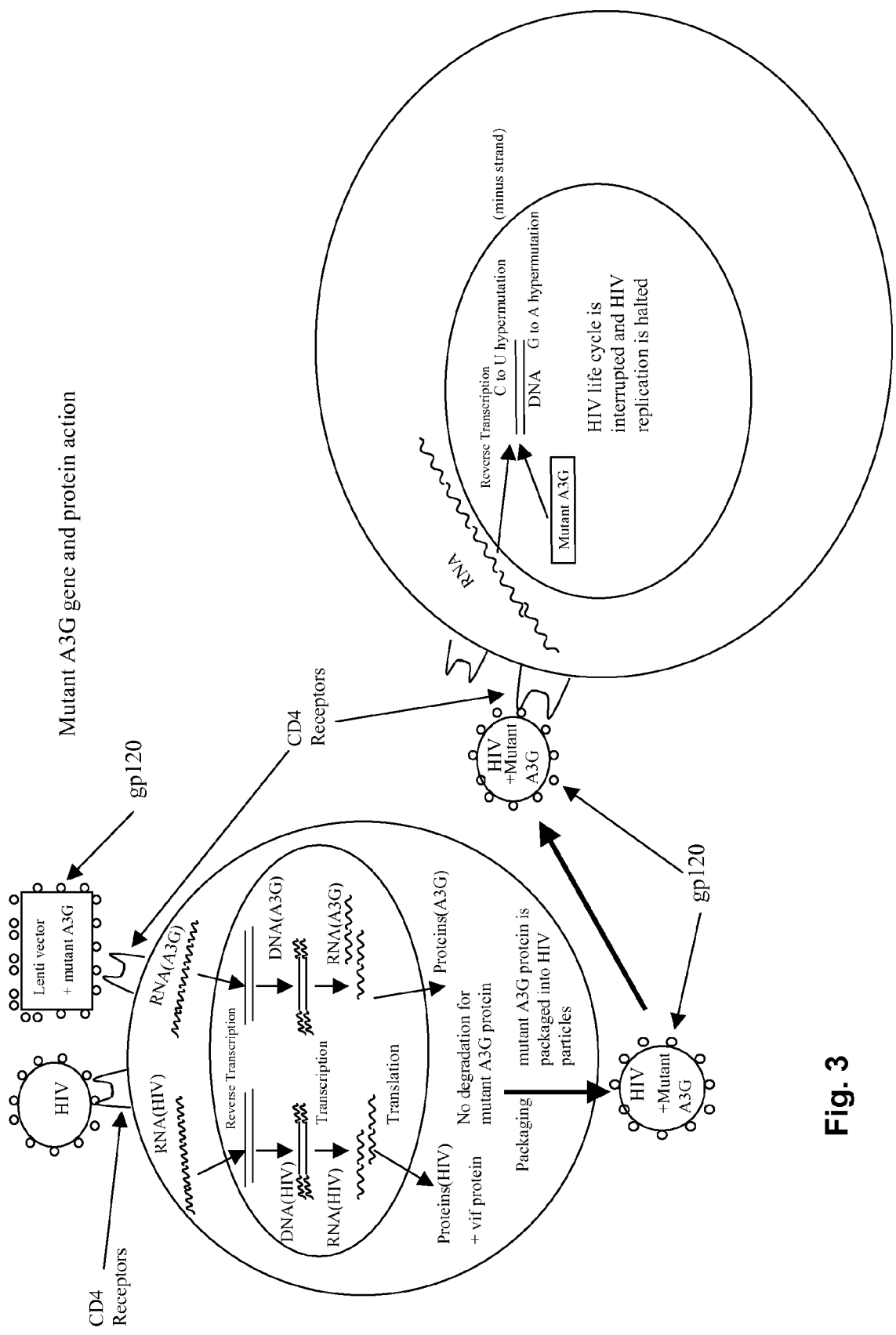

For easy understanding, a specific example of the replication cycle of HIV virus is provided herein with reference to FIG. 1-3.

HIV is a retrovirus that replicates through integrating its viral DNA intermediate into host genome. HIV is a genus of lentiviral family. The HIV particle encapsulates two copies of full length viral RNA, each copy containing the complete genetic information needed for virus replication. Referring to FIG. 1, an HIV virus utilizes its envelope protein gp120 to bind to a cell surface receptor CD4 and co-receptor, chemokine receptor CCR5 or CXCR4, and enters the host cell. After entering the cells, HIV reverse transcribes its RNA genome into a DNA copy using the virally encoded reverse transcriptase that is present in its virion. This DNA copy is integrated into the host genome catalyzed by integrase, another virally encoded enzyme. The integrated viral DNA is referred to as provirus and becomes a permanent part of the host genome. The cellular transcriptional and translational machinery carries out expression of the viral genes. The provirus is transcribed to RNA by host RNA polymerase II, and the RNA is subsequently modified and transported out of the nucleus by viral and host proteins. A fraction of viral RNAs are spliced to allow expression of some viral genes by the host translational machinery. Other viral RNAs remain full-length, and will be assembled into progeny viral particles to become viral genomic RNA. The newly synthesized viral proteins and the full-length viral RNAs are assembled together to form new viruses that bud out of the host cells (Coffin J M, Retroviridae: The Viruses and Their Replication. Lippincott-Raven, Philadelphia, Pa. 1996).

It was discovered in 2003 that a host factor, Apolipoprotein B mRNA-editing enzyme-catalytic polypeptide-like 3G (A3G), can inhibit HIV replication through lethally editing HIV reverse transcribes that causes G to A hypermutation in the proviruses. FIG. 1 is an illustration of the mechanism that A3G uses to interrupt viral replication. A3G is one of innate antiretroviral mechanisms of human and other mammalian species. The detailed disclosure about A3G is set forth and described in PCT Application Number PCT/US05/04371, the disclosure of which is incorporated herein by reference.

A3G (previously named CEM15) that has antiretroviral function is a cytidine deaminase and belongs to the cytidine deaminase gene family, and is one of the seven related genes or pseudogenes found in a cluster on chromosome 22. A3G (wild type A3G) is expressed in human primary CD4+ T cells, the main target of HIV-1. It can be packaged into HIV-1 virions through binding to the viral genomic RNA. During reverse transcription of HIV-1, A3G deaminates deoxycytidines (dC) to deoxyuridines (dU) in newly synthesized viral minus-strand DNA, thereby inducing G-to-A hypermutation and subsequently inactivating the virus. However, this innate mechanism of resistance to retroviral infection is counteracted by the HIV-1 viral infectivity factor (Vif). Vif binds to A3G, induces its ubiquitination, and subsequently, proteosomal degradation, preventing its incorporation into HIV-1 virions.

A brief description of A3G working process is as follows: A3G protein binds to HIV genomic RNA and nonspecific RNA, and is packaged into budding HIV virions if the vif gene of HIV-1 is deleted or mutated. During viral assembly, gag protein forms a complex with the RNA and A3G, resulting the package of A3G into the virions. Gag does not bind to A3G in the absence of RNA. Virion incorporation of A3G is dependent on its level of expression in the virus-producing cells, and incorporation of a few molecules (6-13) of A3G per virions is sufficient to potently inhibit HIV replication subsequently. After the A3G containing HIV virions infect target cells and start reverse transcription, which is one of the key steps for retroviral replication, A3G deaminates the cytidines in the newly synthesized, single strand of viral minus strand DNA into uridines, causing massive Guanine (G) to Adenine (A) hypermutation. This massive hypermutation inhibits HIV replication and interrupts the life cycle of HIV. Referring to FIG. 1 again, the viral minus strand DNA undergoes C to U conversion during reverse transcription of HIV and other retroviruses life cycle that consequently leads to massive G to A hypermutation in viral DNA and halts the viral replication. Research results indicate that HIV virions may package A3G protein before budding out of the host cell if the vif gene of the HIV is defective. It is A3G protein that causes the interruption of the viral replication.

However, this innate antiretroviral mechanism can be antagonized by an HIV encoded protein, viral infectivity factor (Vif). As illustrated in FIG. 2, Vif counteracts the A3G's antiviral function by inducing its quick degradation through ubiquitination and subsequently proteosomal degradation, therefore depleting intracellular wild type A3G protein, preventing wild type A3G protein from packaging into budding HIV virions, protecting the subsequent replication of HIV.

To counteract the function of HIV Vif proteins and inhibit HIV replication, HIV Vif-resistant mutant A3G proteins were discovered and made. Mutant A3Gs that resist Vif-induced degradation can inhibit wild type HIV, while wild type A3G can only inhibit Vif deficient HIV; therefore, the Vif-resistant mutant A3G can be used in gene therapy against HIV infection and AIDS. For example, replacing an amino acid of an A3G sequence, such as aspartic acid (Asp, D) at the position 128 or proline (Pro, P) at the position of 129 of A3G, making the A3G resistant to HIV Vifs. Mutant A3G sequences SEQ ID NO: 2 and SEQ ID NO: 3 are presented to illustrate such mutations. Mutant A3G proteins such as SEQ ID NO: 2, mutant proteins represented by SEQ ID NO: 2 substituted with A, G, R at position 128, mutant A3G protein represented by SEQ ID NO: 3, and mutant proteins represented by SEQ ID NO. 3 substituted with A, G, F at position 129 are able to inhibit HIV replication effectively in the presence of HIV ViV. Experiments indicate that P129D and D128K are the two most potent inhibitors of HIV replication. P129D protein inhibits about 90% of viral infectivity in the presence of HIV-Vif. Preferably, the inhibition is about 95-98% of viral infectivity. More preferably the inhibition is 99% of viral infectivity. In the presence of HIV-2 Vif, wild type A3G and D128K mutant partially lost their anti-retroviral activities, but P129E, P129D and P129F mutants can inhibit viral replication efficiently. Again, P129D is the most potent inhibitor in the presence of HIV-2 Vif, although both D128K and P129D of A3G mutants can potently inhibit HIV replication in the presence of HIV-1 Vif.

Since A3G mutants can resist the Vif-induced degradation, they can be used in gene therapy to treat HIV infection and AIDS. These Vif-resistant A3G mutant genes can be packaged into HIV virions in the presence of Vif protein, causing hypermutation during reverse transcription of HIV, halting the viral replication and inactivating the virus. This invention provides recombinant vectors that can deliver the Vif resistant A3G into the target cells of HIV and methods to produce these vectors. These vectors deliver the mutant A3G into the target cells of HIV, such as CD4+ T cells, and transduce these cells to express the Vif-resistant mutant A3G protein. After HIV infects these cells and starts its replication, the mutant A3G protein is packaged into progeny HIV. When these progeny viruses infect their target cells and start reverse transcription, the mutant A3G protein induces hypermutations in their genome and stops the viral replication. Besides the target cells of HIV, such as CD4+ T cells, the methods disclosed in this invention can also be used in genetic manipulation of stem cells. This is a novel way targets HIV infection directly at the root of HIV infection. Ideally, gene therapy should be efficient, cell-specific, and safe. Gene therapy provides promising therapeutic methods to treat HIV infection and AIDS, and brings hope to AIDS patients. However, one of the challenges of gene therapy is delivering desired genes to target cells efficiently. Accordingly, there exists a need in the art to develop efficient vehicles such as vectors to transport desired genes to host cells, as disclosed in this invention.

Recombinant viral vector provides an efficient way to deliver the therapeutic genes into the target cells. In this invention, recombinant viral vectors are designed, tested and produced to transport mutant HIV Vif-resistant A3G genes to target cells or express excessive amount of wild type A3G gene in these cells. After the vector enters the cells that can be targeted by HIV, it integrates the mutant A3G gene into the cellular genome and expresses the mutant A3G protein in these cells. When HIV infects these transduced cells and starts viral replication, the mutant A3G expressed in these cells can be packaged into progeny HIV virions. The packaged mutant A3G protein induces the G to A hypermutation during reverse transcription of the progeny HIV and blocks the viral replication when the HIV virus infects other cells. FIG. 3 illustrates the principle of utilizing a recombinant viral vector as a vehicle to transport mutant A3G genes to host cells of HIV to halt HIV replication. The term recombinant viral vector refers to a vector that has virus-like structure and comprises some viral elements and/or genes, which can enter its target cells like a virus to deliver desirable genes. The vectors in this invention are HIV-1 or HIV-2 based and may contain mutations or deletions in some or all of the viral encoded protein, therefore the vectors are no longer replication-competent and safe for the patients. The recombinant viral vector in FIG. 3 comprises a nucleotide sequence encoding a mutant A3G protein, such as the sequences represented by SEQ ID NO: 2, or a mutant A3G gene of a mutated SEQ ID NO: 2 with its amino acid residue at position 128 substituted with A, G, or R, or a mutant A3G represented by SEQ ID NO: 3, or a mutant A3G gene of a mutant SEQ ID NO: 3 with its amino acid residue at position 129 substituted with A, G, or F.

FIG. 3 illustrates the antiviral function of the recombinant viral vector. The process of transducing cells by the vector is similar to that of HIV infection of cells. When the recombinant viral vector encounters a host cell, it enters the host cell by binding to CD4 or other receptors on the surface of the host cell with its envelope protein just like an HIV-1. After entering the host cells, the vector that encodes the mutant A3G starts reverse transcription to transcribe its genomic RNA that encodes mutant A3G into a DNA copy by reverse transcriptase. Then the DNA copy is integrated into the host genome by integrase. The integrated DNA encoding mutant A3G becomes a permanent part of the host genome. Again mimicking the viral infection process, the cellular transcriptional and translational machinery expresses genes of the recombinant viral vector, including mutant A3G gene. The host RNA polymerase II transcribes the vector's DNA to RNA, and other cellular processes modify and transport the RNA out of the nucleus. The host translational machinery synthesizes and modifies the vector proteins, including mutant A3G protein. The newly synthesized Vif resistant mutant A3 G protein can bind to HIV genomic RNA and nonspecific RNA, and is packaged into budding HIV virions and make these virions non-infectious.

The above-described principles can be used in gene therapies to treat HIV or other virus infections. The therapy is categorized as treating somatic cells or stem cells such as hematopoietic progenitor cells, depending on the cell types that are targeted. The therapy can also be categorized as ex vivo treatment or in vivo treatment, based on the methods of treatments. In an ex vivo gene therapy, the patient's cells are collected, treated with the vector outside the patient's body, and subsequently these transformed cells including hematopoietic progenitor cells are transfused or transplanted back into the patient's body. In an in vivo treatment, a therapeutically effective amount of recombinant viral vector that encodes the mutant A3G is injected intravenously into patient, with at least one excipient such as sterile water or saline, polyalkylene glycols, oils of vegetable origin, hydrogenated naphtalenes, and the like, and transforms the target cells of HIV, which may be somatic cells such as T cells, or stem cells such as hematopoietic progenitor cells, to express Vif-resistant mutant A3G protein, which is encoded by the vector. Also a gene therapy method can combine both in vivo and ex vivo ways to treat a patient with a recombinant vector.

The present invention discloses a promising gene therapy for treating HIV infection and AIDS disease by using a vector as a genetic vehicle to deliver a wild type A3G or a mutant A3G gene to the target cells of HIV, such as T cells and macrophages, and stop HIV replication and subsequently cure AIDS.

Advantage of using viral vectors is that the recombinant vector uses the same envelope as HIV and only transforms the cells that can be infected by HIV, therefore, it is highly specific. Also, by using this vector, the mutant A3G nucleotide sequence that is intended to be delivered integrates into host DNA easily. All viral specific genes can be removed so that the gene therapy is quite safe. The vector can also be used to deliver genes to different types of cells other than target cells of HIV infection if the envelope used to pseudotype the vector is altered to fit that cell type. In addition, the viral vector can transform both dividing cells and nondividing cells in vitro and in vivo. Whereas nonviral vectors such as liposomes are absent of viral components and lack of previous immune recognition, resulting inefficient gene transfer into the nucleus and poor cell targeting making them less effective tools for HIV treatment.

Further advantage of using the recombinant viral vector of the present invention for gene therapy is cellular specific. The recombinant viral vector only targets the type of cells that is meant to be targeted. The recombinant viral vector follows HIV's infection rout, and enters the same cell the same way. The recombinant viral vector copy number can be controlled small, thereby the immune response and the destruction of the targeted cells can be kept minimum. The recombinant viral vectors can be used to transduce and transform either somatic cells or stem cells such as hematopoietic cells in vivo and ex vivo.

HIV can remain latent in some infected cells. These cells serve as a reservoir of HIV. HIV or its provirus in these cells will replicate again if the cells are stimulated by factors such as immuno-response to an infection. Existing the reservoir is the main reason that is so difficult to eliminate HIV from an infected individual. Because the recombinant vector has many similarities to HIV, it can transform all cell types that are targeted by HIV including those serving as reservoirs of HIV. The mutant A3G-carrying recombinant vector can enter, transform and express Vif-resistant mutant A3G in these reservoir cells, and makes the HIV produced from these cells non-infectious. This invention targets the safe house of HIV, therefore, provides solution to eliminate HIV from infected individual, and possibly, cure for HIV infection and AIDS.

Design of Recombinant Viral Vector

Figure 4:
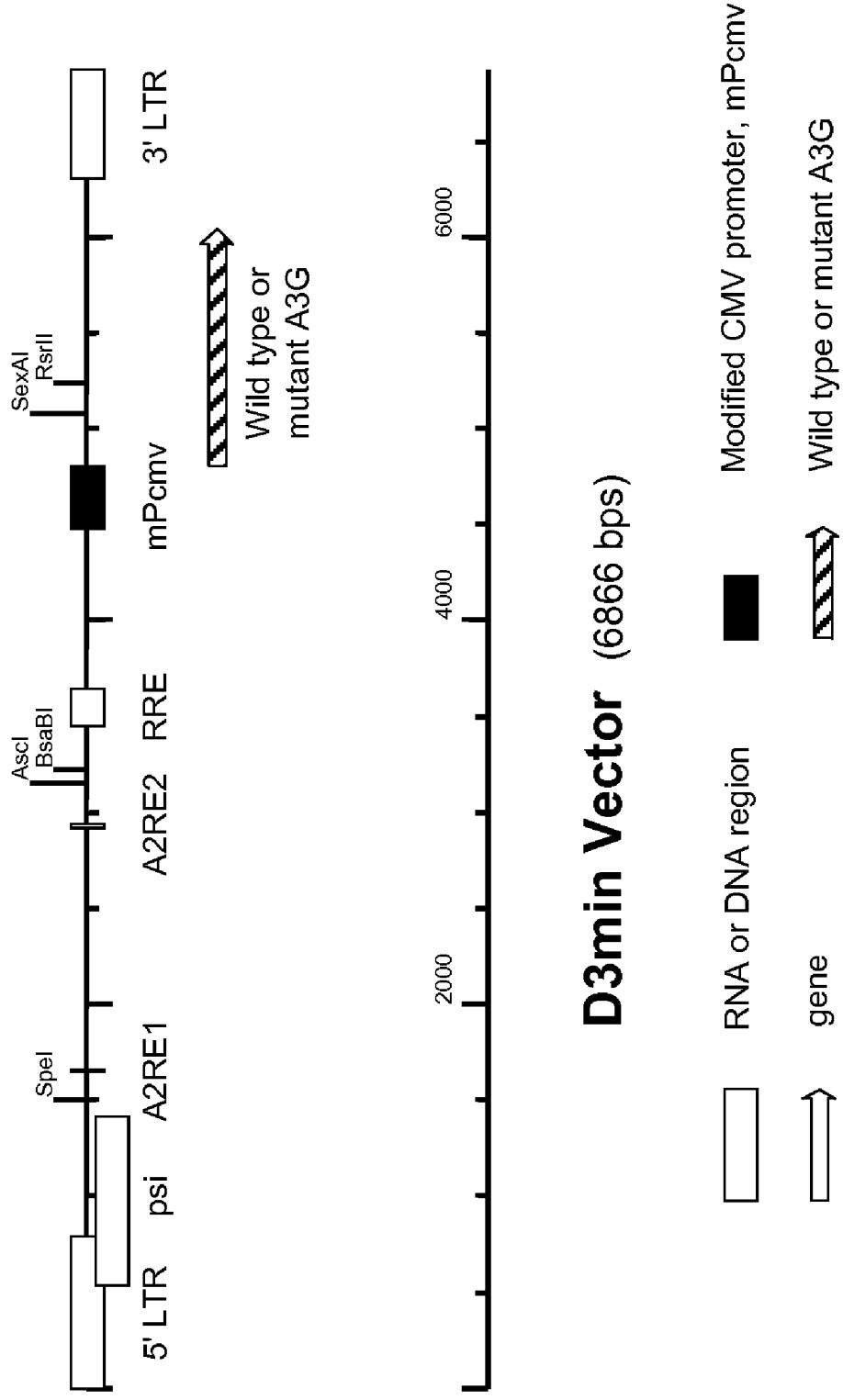

In according to one aspect of the present invention, designs (examples) of a genomic structure of the recombinant viral vector are provided. FIG. 4 illustrates a recombinant vector for delivering A3G genes into human cells comprising (i) a gene expression block including an A3G gene selected from a wild type A3G gene represented by SEQ ID NO: 1 and mutant A3G genes and (ii) a group of lentiviral elements and regions of packaging signal (ψ, psi), LTRs, RRE, and PBS; wherein said A3G gene is operably linked to the packaging signal (ψ, psi), LTRs, RRE, and PBS. Examples of mutant A3G genes are represented by SEQ ID NO: 2 or SEQ ID NO: 3, and the sequences have mutations at the position 128 and 129 of the sequences.

In at least one embodiment, an entire sequence of a recombinant vector, D3 min, is disclosed in SEQ ID NO: 5. The D3 min vector comprises a mutant A3G gene represented by SEQ ID NO: 3. Alternatively, a wild type A3G gene or mutant A3G genes can be used to replace the mutant A3G gene represented by SEQ ID NO: 3. The wild type or mutant A3G gene can be inserted into any one site of the recombinant viral vector. The virus that served as the backbone in constructing the recombinant viral vector can be a lentivirus. An example of the virus is a retrovirus. In one embodiment of the present invention, the recombinant viral vector comprises genes, viral elements and regions from an HIV virus, which is either from an HIV-1 or an HIV-2 virus. The viral genome can also be originated from other types of virus such as an adenovirus or a respiratory syncytial virus (RSV).

The long terminal repeats (LTRs), packaging signal (ψ, psi), and Rev responsive element (RRE) to which the wild type A3G gene or the mutant A3G genes is operably linked, will be further elaborated in the following paragraph. The LTRs comprise a 5'LTR which is at the 5'site of the vector's sequence, and a 3'LTR which is at the 3' site of the vector's sequence. The LTRs can be from natural viral sequences, modified sequences from viruses or purely artificial sequences. Normally, LTRs can be divided into U3 (unique 3'), R (repeat), and U5 (unique 5') regions. The U3 region contains viral promoters and transcriptional enhancers. The R region is essential for reverse transcription and replication of all retroviruses. Specifically, HIV-1 R region contains a trans-activation response region (TAR) that is important for activation of HIV-1 gene expression, and has the promoter's function to drive the vector's gene expression. The U5 region contains sequences that facilitate the initiation of reverse transcription. Consequently, LTRs can work as promoters/enhancers for the vector to express excessive wild type A3G or mutant A3G. Immediately downstream of the 5' LTR is a primer binding site (PBS) that has sequence complementary to a portion of a cellular tRNA. The packaging signal (ψ, psi) and encapsidation signal (E) are sequences that interact with the viral proteins to accomplish specific packaging of the viral RNA. The wild type A3G gene or the mutant A3G gene is also operably linked to an RRE element in the recombinant viral vector, which allows the vector RNAs containing the A3Gs being transported across the nuclear membrane. RRE is Rev-responsive element of HIV, which is an RNA structure located within the env gene. The RRE region forms a well-defined structure on the outside of a large bulk of secondary structure, enclosed by more than 350 base pairs. The binding of the Rev protein to RRE promotes the transport of unspliced HIV transcripts to the cytoplasm. The wild type A3G gene or the mutant A3G is further operably linked to a packaging signal (ψ, psi) in the recombinant viral vector to allow the viral vector genome that encodes A3G to bud out of the cell and deliver either a wild type A3G gene or a mutant A3G gene into T cells, macrophages or stem cells such as hematopoietic progenitor cells.

In accordance with one embodiment of the present invention, the recombinant vector has a promoter selected from the group consisting of an EF1-α (elongation factor 1 alpha) promoter, a CMV (cytomegalovirus) promoter, an SV40 (simian virus 40) promoter, and a modified CMV (cytomegalovirus) promoter. The promoters mentioned above are all commonly known in the art. The promoters can be inserted into any position that is at 5' end of the A3G gene in the vector, except in PBS, RRE. A promoter is a DNA sequence that permits proper activation or expression of the gene that it controls. The promoter usually contains TATA box, upstream repeat sequences, numerous DNA motifs or cis-elements that can serve as recognition signals and binding sites for transcription factors. The promoter plays crucial roles in the level of expression of the adjacent gene. Therefore, the vectors using additional promoters may gain more leverage in terms of controlling the expression of the A3G genes. An exemplary promoter is modified CMV (cytomegalovirus) promoter represented by SEQ ID NO: 4.

The amino acid substitution mutations of A3 G in the recombinant viral vector, enabling the vector to inhibit HIV-1 and/or HIV-2 replication in the presence of HIV-1 Vif or HIV-2 Vif are further explained here. In one embodiment, the mutation on the A3G gene is a P129D substitution. The substitutive mutation on the A3G gene can also be a P129A substitution, or a P129G substitution, or a P129F substitution. In one embodiment, the mutant A3G gene is selected from the group consisting of a mutant A3G gene represented by SEQ ID NO: 2, mutant A3Gs with an amino acid substitution at position 128, a mutant A3G gene represented by SEQ ID NO: 3, and mutant A3Gs with an amino acid substitution at position 129. The mutant SEQ ID NO: 2 can be substituted with A, G, or R at position 128. The mutant SEQ ID NO: 3 can be substituted with A, G, or F at position 129. In yet another embodiment, the mutation on position P129 may be any amino acid substitution except Proline. In some embodiments, it is contemplated that other A3G gene having an amino acid substitution at 129 reduce or inhibit viral infectivity and replication in a host cell or subject.

The recombinant viral vector of the present invention utilizes the features of a virus to facilitate the vector to get into a mammalian cell and transduce it. The necessary viral proteins required in the recombinant viral vector production can be provided by transfecting the vector-producing cells with the plasmids that express these proteins or transducing and selecting the vector-producing cell lines that are stably express these viral proteins. Some viral elements, regions and genes such as U3, R U5, PBS, gag, pol, tat, rev, may be retained, and some viral genes such as vif, vpr, vpu, reg are deleted in the process of designing and constructing the recombinant vectors-producing plasmids. All other viral proteins required the vector production can be provided by expressing these proteins in the vector-producing cells (FIG. 4).

Figure 5:
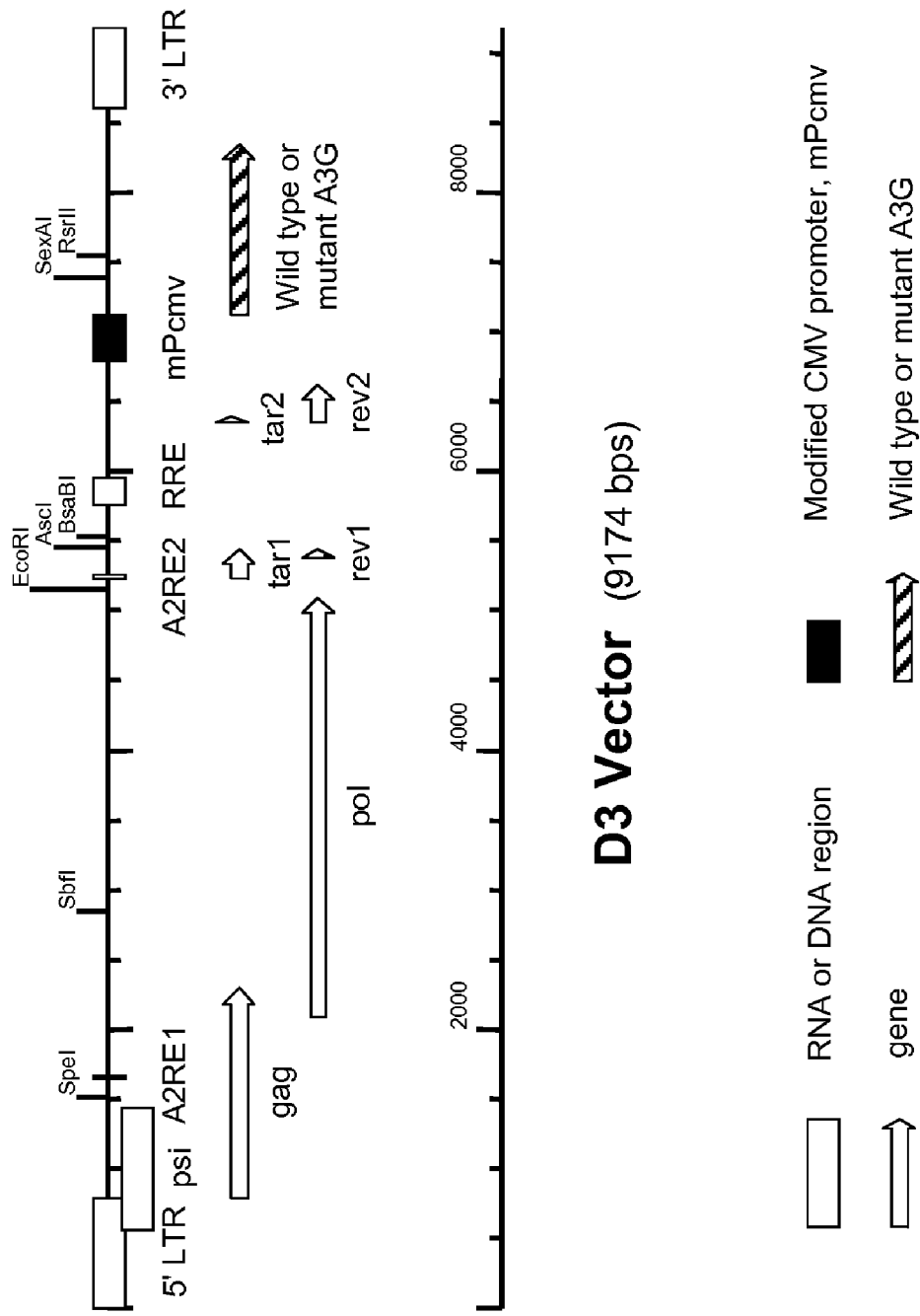
Figure 6:
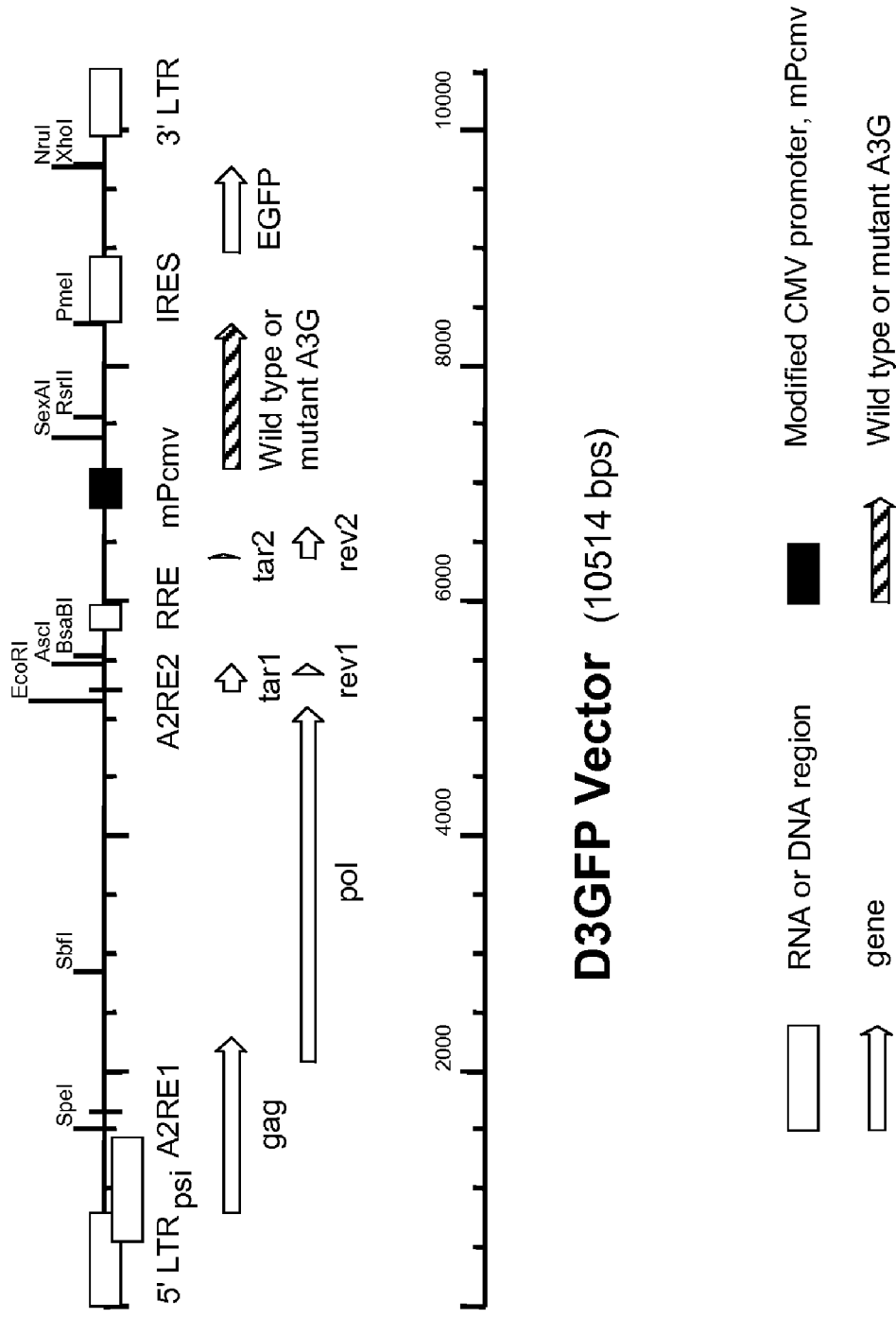
Figure 7:
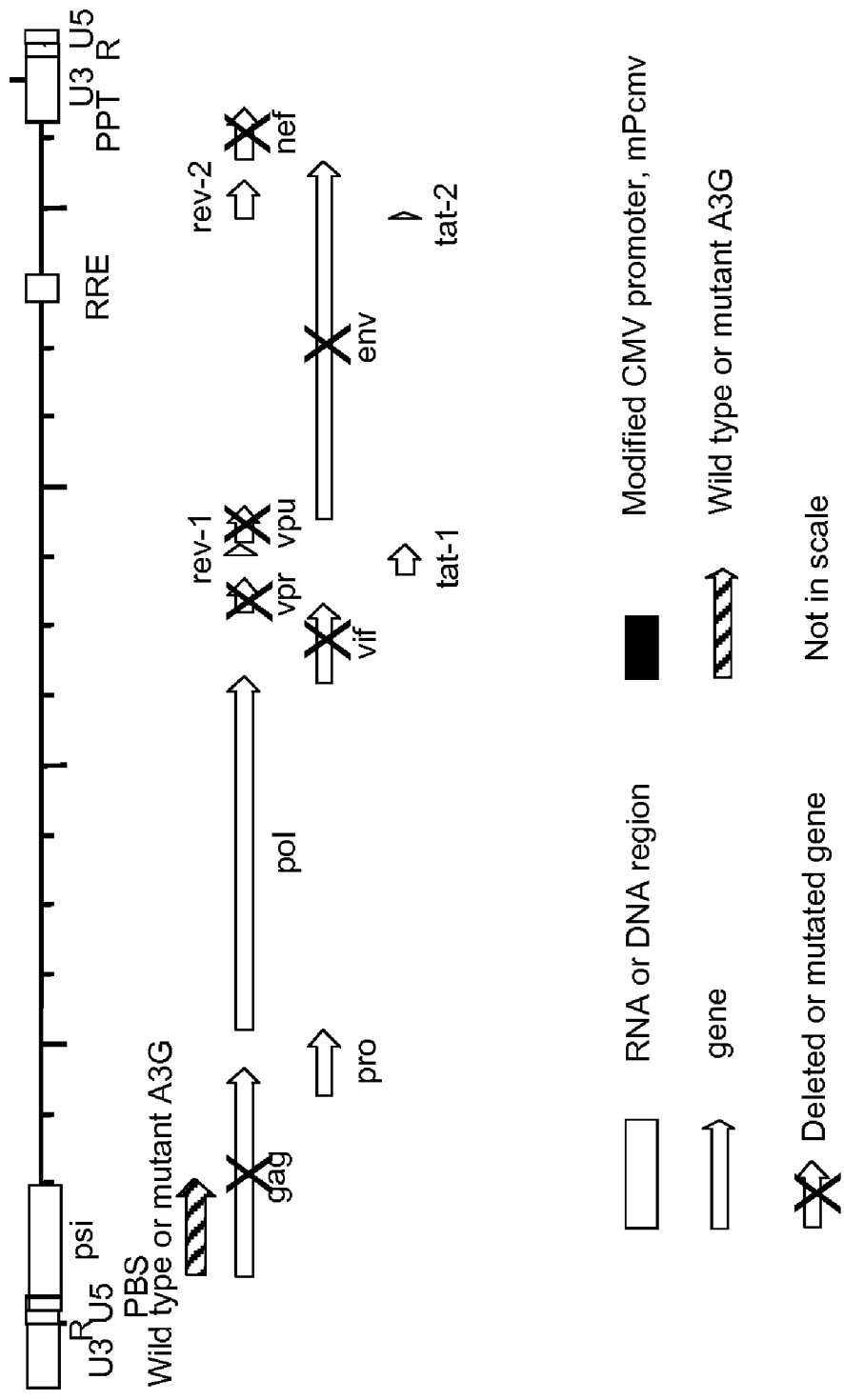
Figure 8:
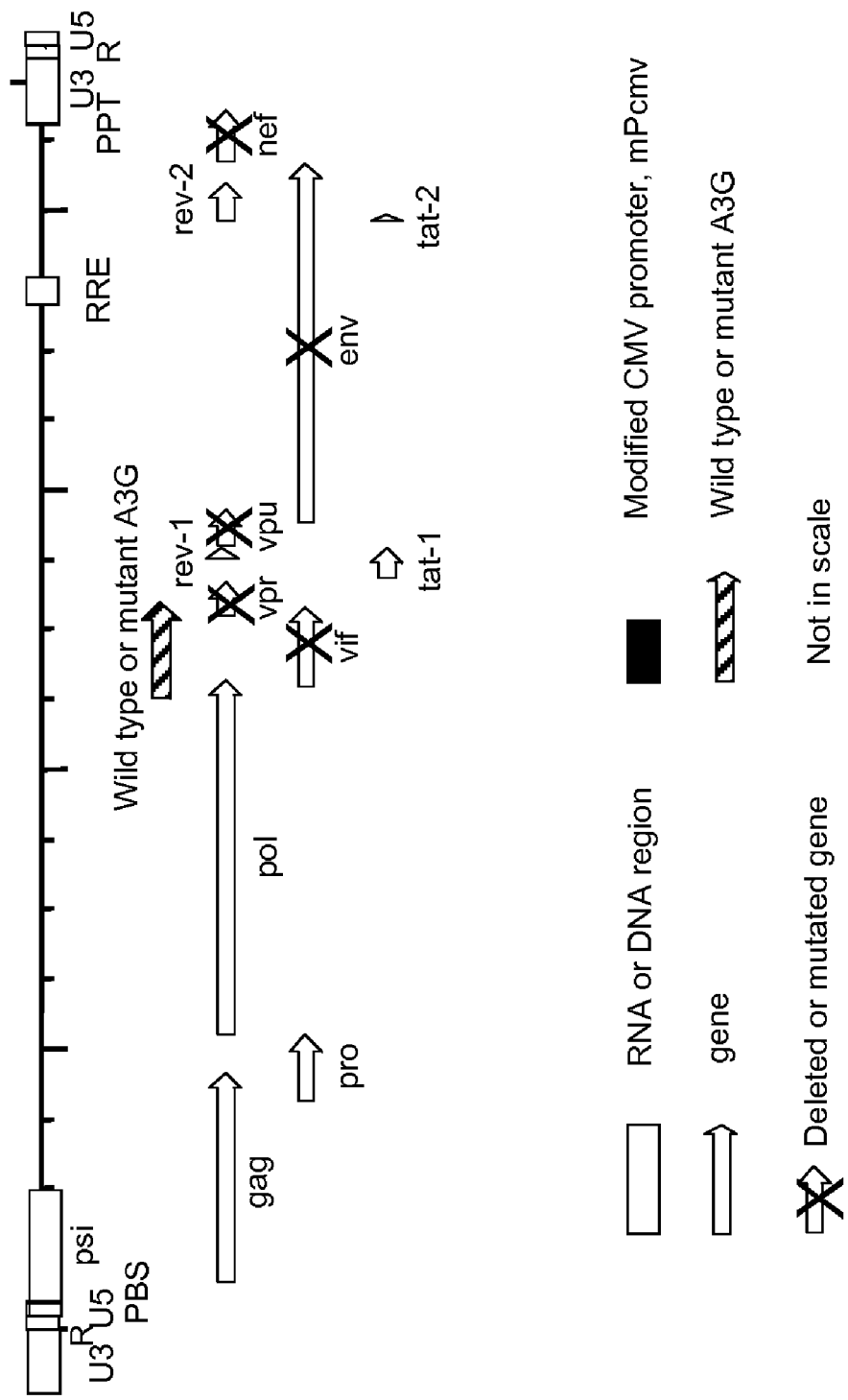
Figure 9:
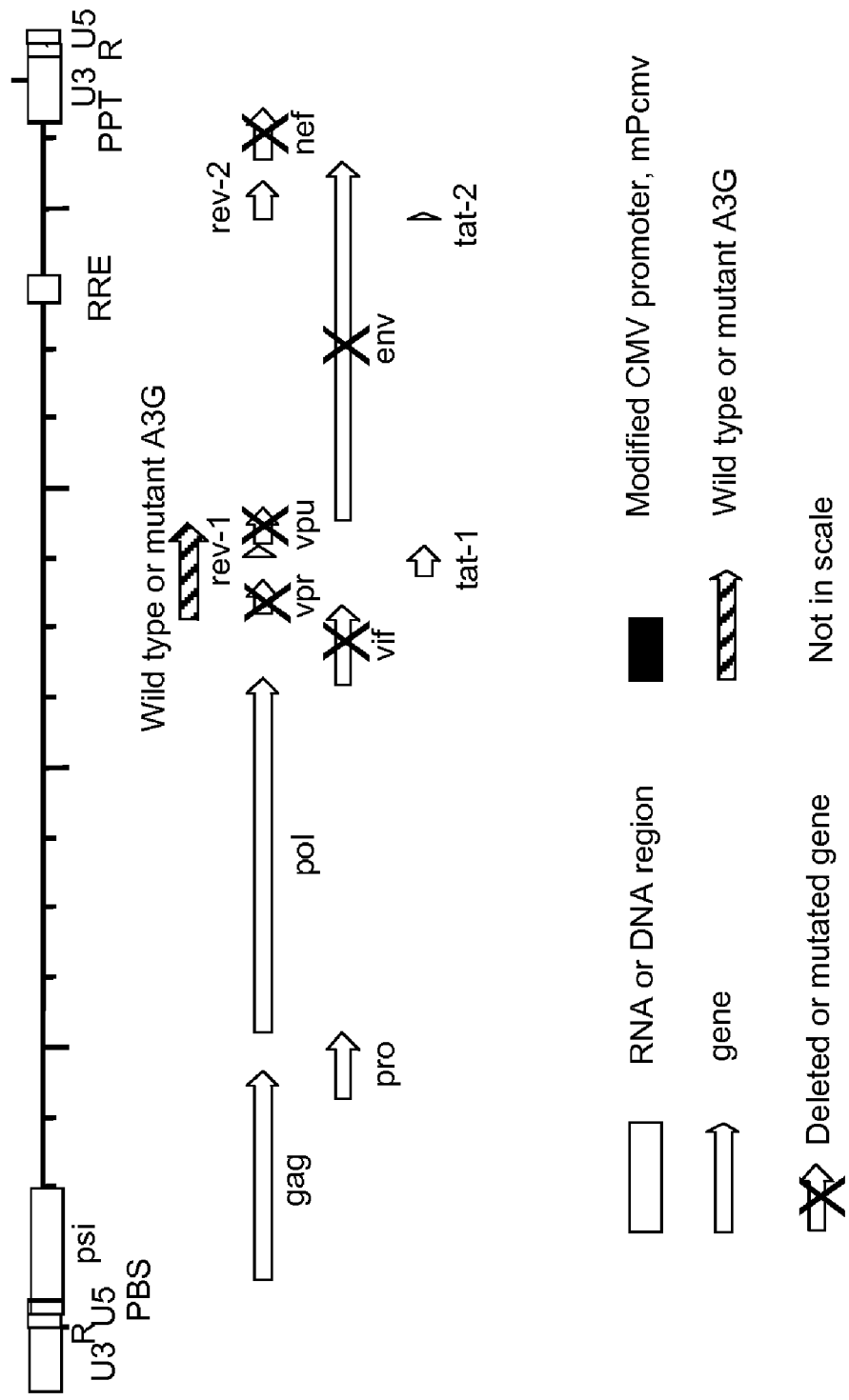
Figure 10:
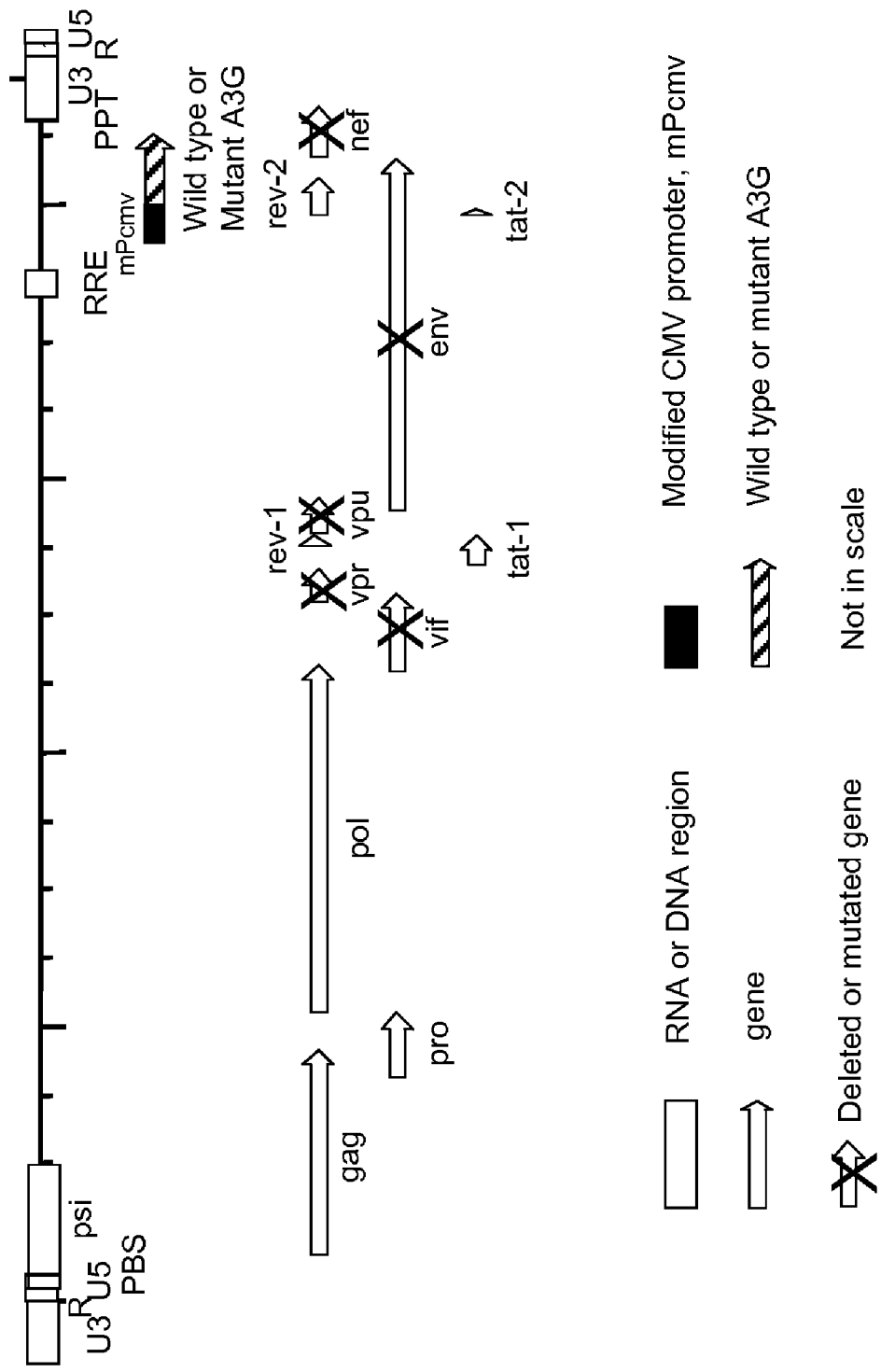

In the following paragraphs, more recombinant viral vectors of the present invention will be disclosed. FIG. 5 shows D3GFP vector, which is the preferred vector of current invention disclosure, and the entire sequence of D3GFP vector which expresses enhanced green fluorescent protein (EGFP) reporter, is disclosed in SEQ ID NO: 7. As shown in FIG. 5, the recombinant viral vector, D3GFP, has elements and/or regions of 5'LTR, 3' LTR, RRE, PBS, viral genes of gag, pol, tat, and rev originated from HIV-1, an expression cassette comprising modified CMV (mPcmv) promoter and a mutant A3G gene represented by SEQ ID NO: 3 is inserted between RRE and 3'LTR. Alternatively, a wild type A3G gene or other mutant A3G genes can be used to replace the mutant A3G gene represented by SEQ ID NO: 3. The expression cassette is not efficient and expresses modest amount of A3G in transduced cells to maximize the production of infectious vectors. FIG. 6 shows structure of another recombinant vector D3, which doesn't contain EGFP gene. The other elements, regions and genes such as 5'LTR, gag, pol, tat, RRE, rev, PBS and 3' LTR genes, a wild type A3G gene or a mutant A3G gene, and a modified PCMV (mPcmv) promoter are arranged exactly the same as D3GFP. The entire sequence of D3 vector is disclosed in SEQ ID NO: 6. Neither D3GFP nor D3 vector contains viral genes of vif, vpr, vpu, nef, and env, for bio safety reasons, although these genes can be included in the vectors. The position for insertion of the wild type A3G gene or the mutant A3G gene in the vectors can be varied. Several alternative designs of the vectors show the wild type A3G gene or the mutant A3G gene can be inserted into different locations of vectors. Referring to FIG. 7, a mutant A3G gene is inserted into the gag open reading frame (ORF) of a recombinant viral vector. No additional promoter is needed. The expression of the A3G gene is driven by LTR promoter. This design of the recombinant viral vector has been tested for its cellular transduction potency, with the advantages of easy to transfect target cell types specifically and producing less virion copy numbers, which generates less immulogical reaction and increases the host cell survive rate.

Further exemplary designs of f the recombinant viral vectors are provided in FIG. 8 through FIG. 10. The person skilled in the art can develop various recombinant viral vectors based on the examples and design principles disclosed in the description, which are included in the scope of this disclosure.

FIG. 8 shows a design of a genomic structure of the recombinant viral vector according to one embodiment of the present invention, in which the A3G gene or the mutant A3G gene is inserted in the open reading frame of vif gene of a recombinant viral vector. The viral genes of gag, vif, vpr, vpu, nef, env, tat, and rev genes in the original genome are deleted or mutated. No additional promoter is in the vector. The expressing of A3G gene is driven by LTR promoter and through mRNA splicing.

FIG. 9 shows another design of a genomic structure of the recombinant viral vector, in which the A3G gene or the mutant A3G gene is inserted in the open reading frame of vpr gene of a recombinant viral vector. The viral genes of vif, vpr, vpu, nef, env, tat, and rev genes in the original genome are deleted or mutated. The A3G gene is expressed from LTR as the promoter and through mRNA splicing.

FIG. 10 shows yet another design of a genomic structure of the recombinant viral vector, in which the A3G gene or the mutant A3G gene attached to a wild type PCMV (Pcmv) promoter is inserted into the region of envelope gene of a recombinant viral vector. The A3G gene can be also expressed from other promoters such as EF1-α promoter or SV40 promoter. The promoter and the A3G gene can be inserted into anywhere upstream of the A3G gene in the vector, except in PBS, or RRE. The viral genes of, vif, vpr, vpu, nef, env, tat, and rev genes in the original genome are deleted or mutated.

There are a variety of choices of inserting the A3G gene or the mutant A3G gene into the recombinant viral vector. However, the order of construction may affect the function of the A3G gene to inhibit viral replication. If the A3G gene is desired to be inserted into any one site of the open reading frames of viral genes, such as gag or pol gene, the viral gene needs to be deleted before the insertion of the A3G gene or the mutant A3G gene to avoid producing chimeric A3G or mutant A3G proteins.

Method of Making Recombinant Viral Vector

In this section, the methods for producing and manufacturing the recombinant viral vector derived from lentiviral family such as HIV-1 and HIV-2 based vectors that carries and expresses a wild type A3G gene or a mutant A3G gene in human primary CD4+ T cells, macrophages, hematopoietic stem cells and human cell lines are disclosed.

The general process of making the recombinant vectors includes several steps. First step prepares a vector-producing cell line, in which a vector-producing cell line is transiently transfected with several plasmids, including the vector-producing plasmid, envelope protein expressing plasmid and plasmid expressing a lentiviral protein or other protein degrading A3G and its mutants. Next, A3G proteins within the vector-producing cell line are eliminated by expressing a lentiviral protein or other protein in the vector-producing cell line to degrade the A3G proteins within the vector-producing cell line, and the vector-producing cell line is then infected by recombinant vectors such as D3 min, D3, or D3GFP. Last, envelope proteins in the vector-producing cell line are expressed.

Several examples are described here for purpose of illustrating of the methods of making recombinant vector, which are for demonstration only. It is not limited for the scope of the current invention. Various methods can be developed by the person skilled in the art based on the illustration, which are included in the scope of the invention.

The initial step of making a functional recombinant viral vector according to the present invention is to design and construct vector-producing plasmids, supporting plasmids and Helper plasmids that are used in vector producing. The plasmids pD3, pD3GFP and pD3 min containing a mutant A3G gene in their constructs are constructed. Supporting plasmids expressing Vif protein, such as pSIVmacVif, envelopes, such as pCMV-VSVg, pCXCR4env and pCCR5env that express VSVg, HIV-1 CXCR4 and CCR5 envelopes, respectively, are prepared. The Helper plasmids, such as pC-HelpΔvif that express all viral proteins except Vif and Vpr, are also prepared. These plasmids are used in the process of producing the recombination vectors that are disclosed in this invention. The vector-producing cells are made either from transiently transfected 293 cells, 293T cells or other mammalian cell lines with the supporting and Helper plasmids or cell lines that express these necessary proteins.

Figure 11:
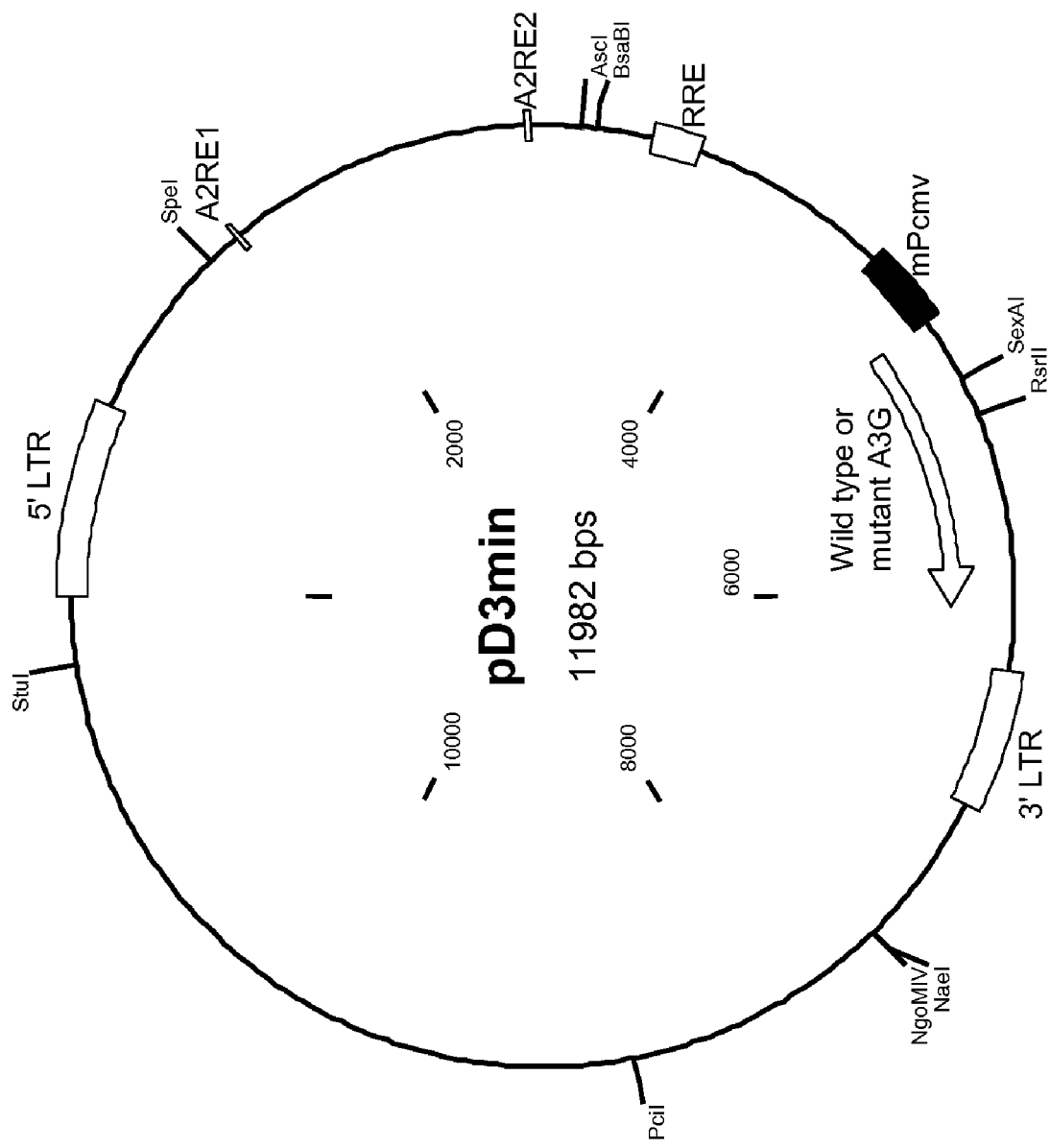

The plasmids such as pD3, pD3GFP, pD3 min, pSIVmacVif, pCMV-VSVg and pCCR5env are constructed using standard methods of molecular biology. The sample structures of plasmids pD3 min, pD3GFP and pD3 are disclosed in FIG. 11, FIG. 12 and FIG. 13 respectively. The person skilled in the art can employ various restriction enzymes to cut different restriction sites of the plasmids, insert the wild type A3G gene or the mutant A3G genes into the plasmids based on the illustrations and the descriptions in previous section "Design of Recombinant Viral Vector", and ligate them to get these vector-producing plasmids. Some viral genes of lentiviral virus such as vif vpr, vpu, nef, env, tat and rev may be deleted or mutated from the plasmids according to the plan of the previous section "Design of Recombinant Viral Vector" for safety reason. Certain genes besides the mutant A3G gene may be inserted the same way as described above to enhance the function of the viral vector to express the wild type A3G gene or the mutant A3G genes in host cells.

An example, as disclosed herein, describes the procedure to produce a recombination vector that can be used to treat HIV infections and AIDS. The example is to produce recombinant vector D3GFP, whose structure is illustrated in FIG. 5 and the structure of vector-producing plasmid, pD3GFP, is illustrated in FIG. 12.

Figure 12:
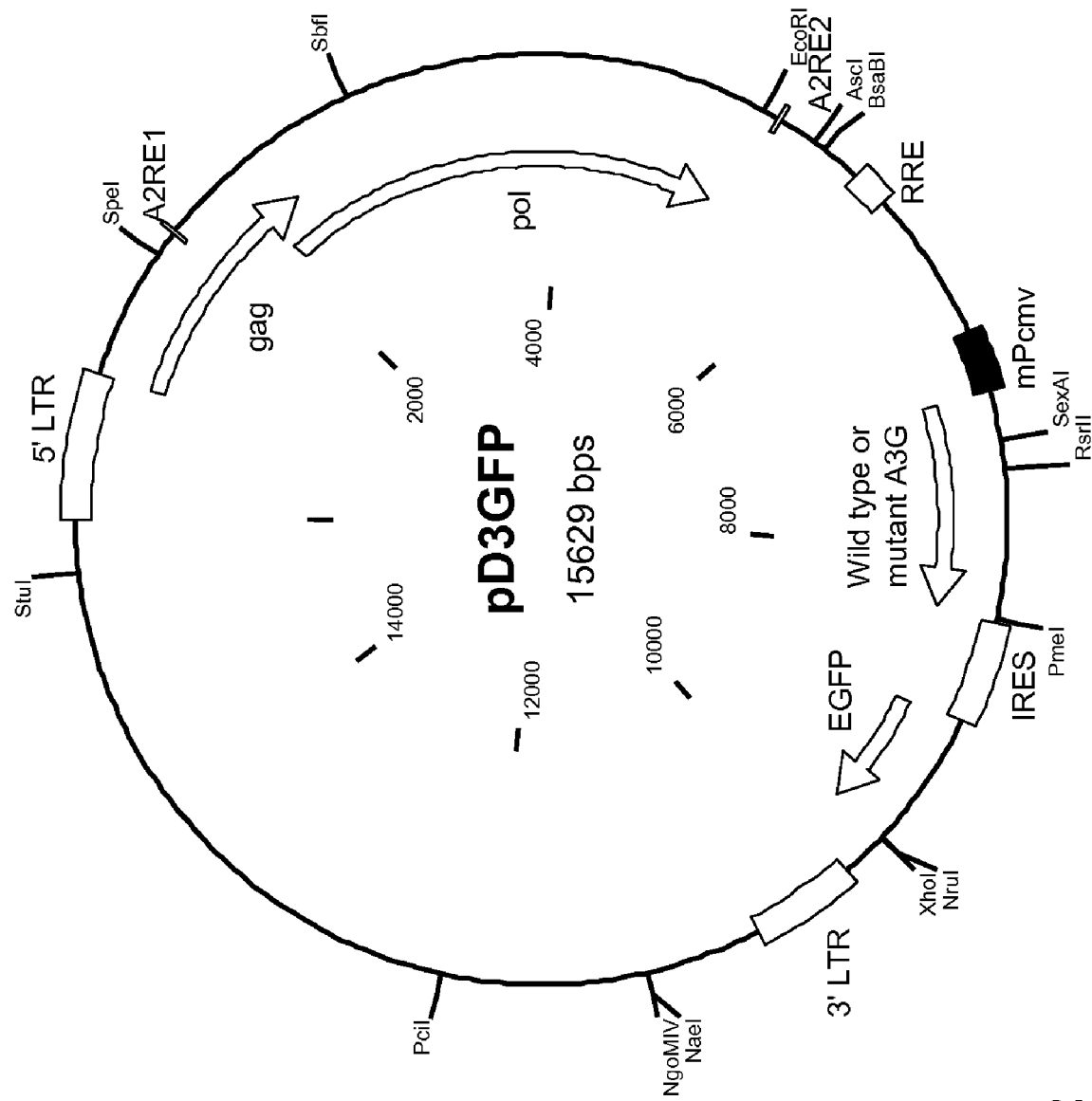
Figure 13:
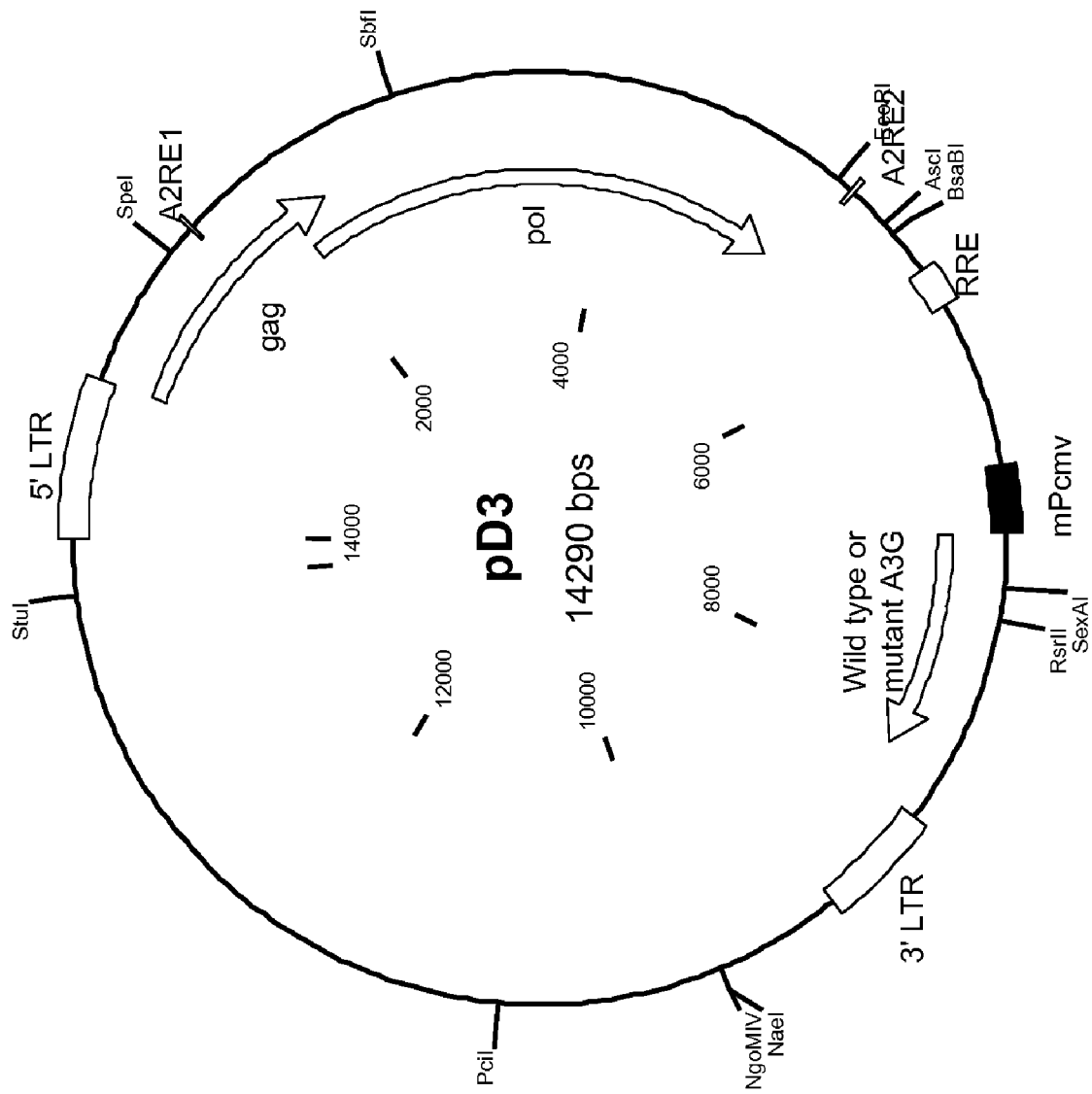

The first step of producing the recombination vector is to design and construct vector-producing plasmid as illustrated in FIG. 12. In this step a recombinant vector comprising retroviral elements and genes, LTRs, packaging signal (ψ, psi), RRE, and PBS, gag, pol, tat and rev, an expression cassette of A3G comprising a modified CMV promoter, a mutant A3G gene (SEQ ID NO: 3), an internal ribosomal entry site (IRES) and green fluorescent protein gene (GFP) is constructed. The expression cassette of A3G is operably linked to the packaging signal (ψ, psi), LTRs, RRE, and PBS.

Figure 18:
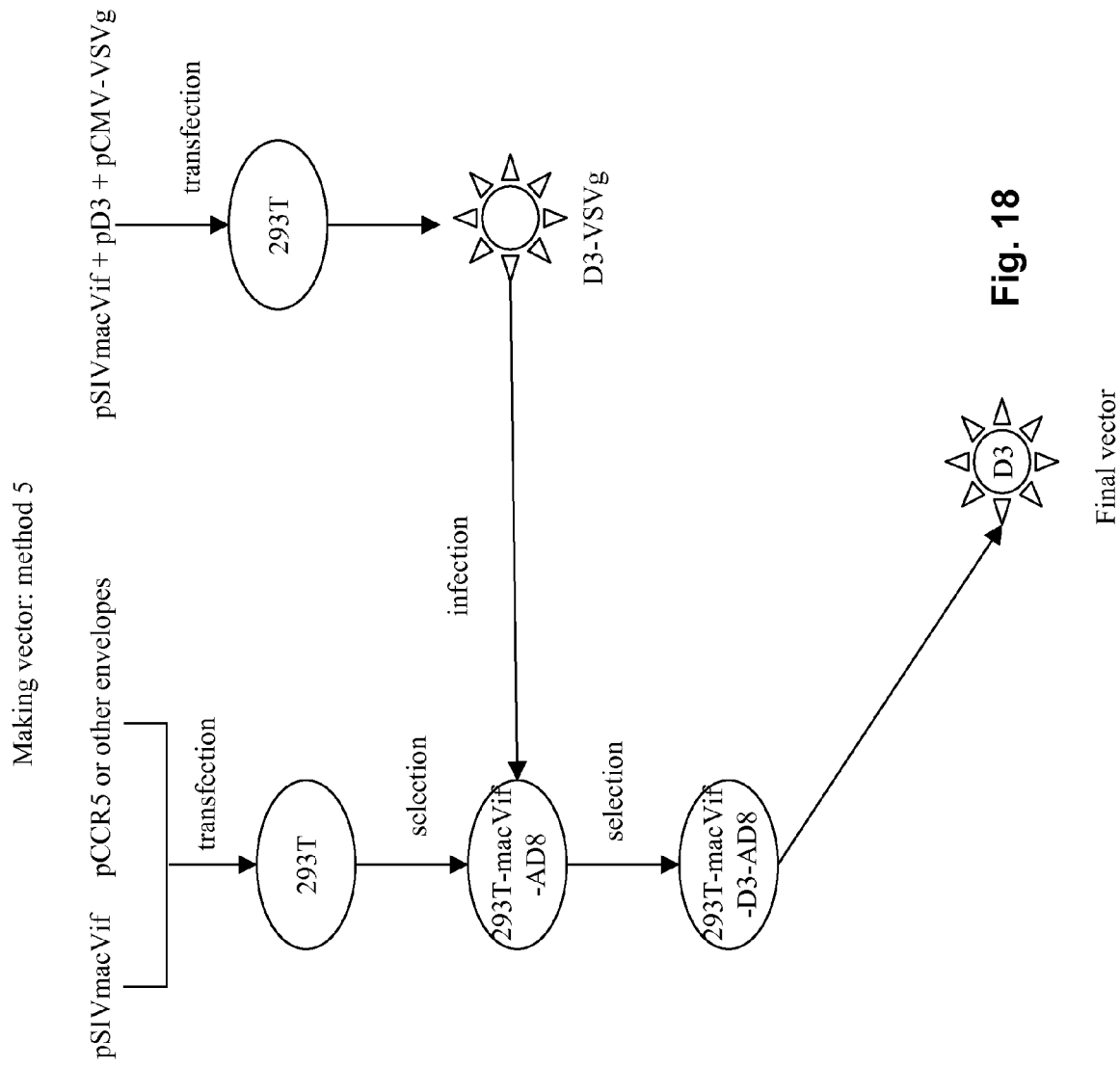

The second step is to establish a vector-producing cell line. The vector-producing cell line is established using cells, such as 293, 293T or other human cell lines as parent cell lines. In this particular case, the vector-producing cell is established using 293T cell line transiently transfected with pSIVmacVif and pCCR5env, as illustrated in FIG. 18. After selection, the cell line that expresses Vif of macaque simian immunodeficiency virus (SIVmac) and CCR5 envelope protein of HIV-1, 293T-macVif-AD8, is established. Then the 293T-macVif-AD8 cell line is infected by VSV-g pseudotyped D3 vector produced from 293T cells that are transiently transfected with pD3GFP, pSIVmacVif and pCMV-VSVg. After selection, the cell line that produces infectious D3GFP vector, 293T-macVif-D3GFP-AD8, is established. In this cell line, the A3G protein is eliminated by the expression of SIVmac Vif in the same cells. There are other methods to eliminate A3G protein in a vector-producing cell line: 1). expressing Vif proteins of other retroviruses in the vector-producing cell lines; 2) expressing natural or artificial proteins or polypeptides that can induce the degradation of A3G; and 3) producing small interference RNA (siRNA) that disrupts the expression of A3G in the vector-producing cells. The processes of producing vectors, D3 min and D3 are similar to that of D3GFP production, except the Helper vector, pC-HelpΔVif, should be used in establishing the vector-producing cell line of D3 min and production of the vector D3 min.

The methods described above can be used to produce the recombinant vectors, including D3 min, D3 and D3GFP, that are used to treat HIV infection and AIDS. The term, "production", is also referred as manufacture of the vector. Various embodiments of manufacture of the recombinant vector are disclosed in the following paragraphs.

First, vector-producing cell lines are established. The parent cell lines for establishing the vector-producing cell lines can be 293, 293 T or other mammalian cell lines. The A3G protein in the vector-producing cells is degraded by expressing a lentiviral protein such as Vif protein, natural protein or artificial protein in the vector-producing cells. The Vif proteins can be HIV-1 Vif, HIV-2 Vif, SIVagm Vif, SIVmacVif, and modified SIVmacVif. In this step, a gene of the Vif protein, a natural protein, or an artificial protein is inserted into the genome of the vector-producing cells. As the result, A3G protein in the vector-producing cells is eliminated by expressing the Vif, the natural protein or the artificial protein, therefore, the vectors produced from these vector-producing cell line are infectious, and can be used infect the target cells of HIV to inhibit replication of HIV. An exemplary Vif nucleotide and protein sequences of a modified SIVmacVif is disclosed in SEQ ID NO: 8. The Vif genes can be modified using codons preferred by human cells to make Vif proteins work more effectively in the process of degrading A3G protein in human cell lines. Another advantage of the codon-optimized Vif is biosafty. The optimized vif sequence reduced the probability of emerging recombinant viruses that can endanger the patients. For example, the modified SIVmacVif is codon-optimized for better performance by using codons that are preferred by human cells.

Small interference RNA (siRNA) can also be used in vector-producing cells to eliminate the A3G protein in the vector-producing cells. The siRNA is expressed in the vector-producing cells to disrupt the production of A3G proteins within the vector-producing cells, therefore, the vector produced from these cells are infectious, which is useful in antiretroviral treatment.

The recombinant vectors are harvested from the culture supernatant of the vector-producing cells by either filtering through a 0.45 μm filter or centrifugation in the sterile condition, or other methods known in the art. The recombinant vectors may be concentrated using centrifugation or other methods known in the art. Now, the vectors are ready to be mixed with excipients to form final therapeutic reagents or used directly in variety methods to treat HIV infection and AIDS.

The detailed processes of producing the recombinant viral vectors are illustrated in examples in FIGS. 14-18. In general, the recombinant viral vectors can be generated by co-transfecting cells with the plasmids pD3, or pD3GFP, or pD3 min, and pSIVmacVif, pCMV-VSVg and pCCR5env as producers. Examples of host cells are 293 (human embryonic kidney cell line) or 293T (293 cells that carry T antigen of adenovirus). In the case of HIV-1-based vectors, the backbones of the vectors and some viral genes used in the vector are from HIV-1.

Again, in the following processes represented by FIG. 14 through FIG. 18, many of the plasmids used in the processes are representative and for illustration only, and can be replaced by similar plasmids. For example, plasmids pSIVmac Vif can be replaced by pcDNA3-macVif (macaque Vif-expression plasmid) or other plasmid expressing HIV-1 Vif, HIV-2 Vif, SIVagm Vif, SIVmacVif, modified SIVmacVif, natural protein, artificial protein; pD3 can be replaced by pD3D128K or other pD3 plasmids that carry wild type or mutant A3G, such as pD3D128A, pD3D128G, pD3D128R, pD3P129D, pD3P129A, pD3P129G, pD3P129F; pCCR5env express CCR5 receptor (a β-chemokine receptor) can be replaced by other plasmids that express other envelope proteins, such as pCMV-VSVg (VSV-g envelope expression vector). Many possible replacements of the plasmids can be employed by the person skilled in the art and are included in the scope of the invention.

Figure 14:
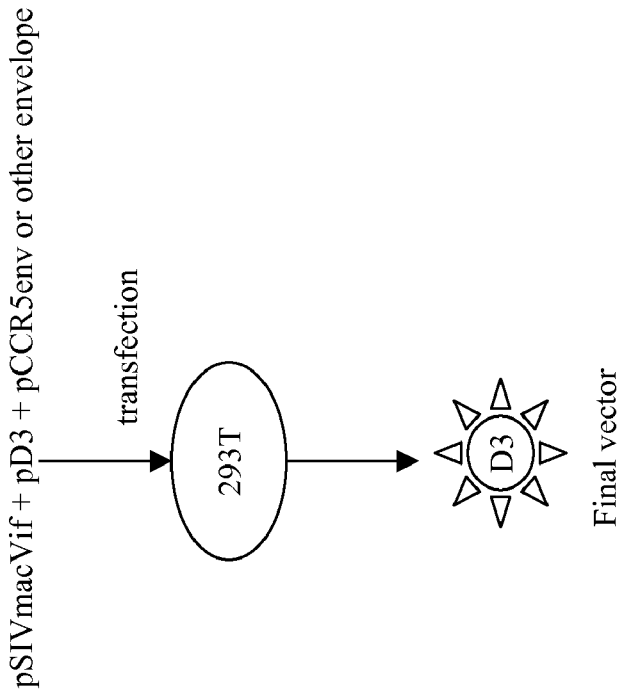
Figure 15:
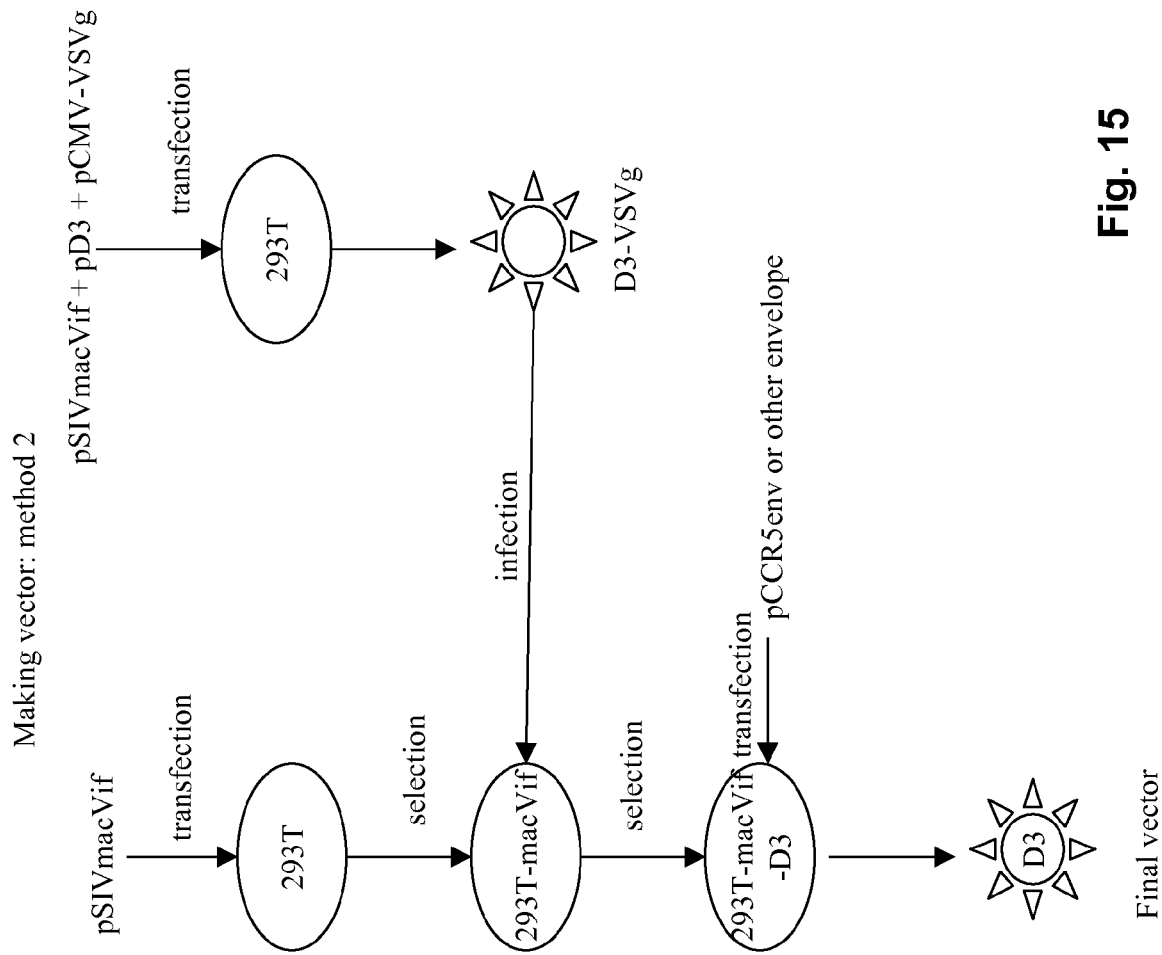
Figure 16:
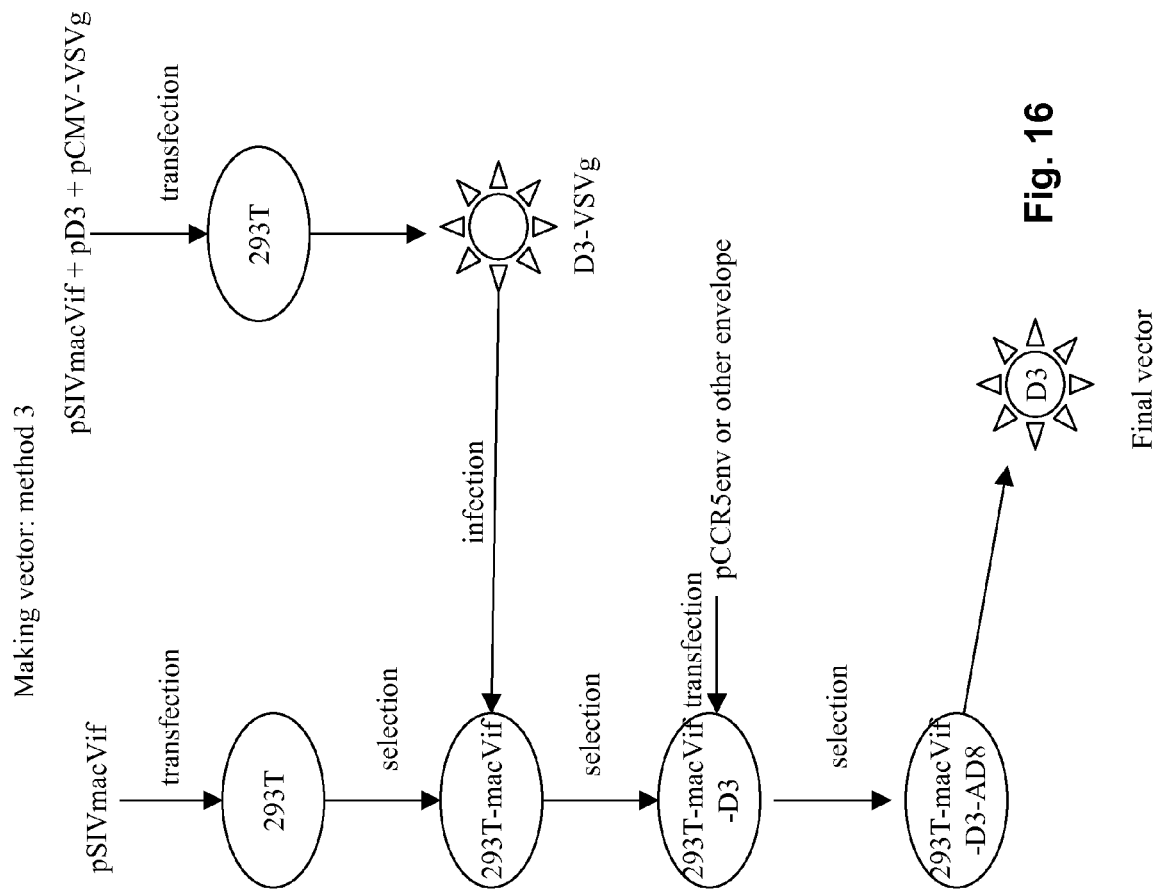
Figure 17:
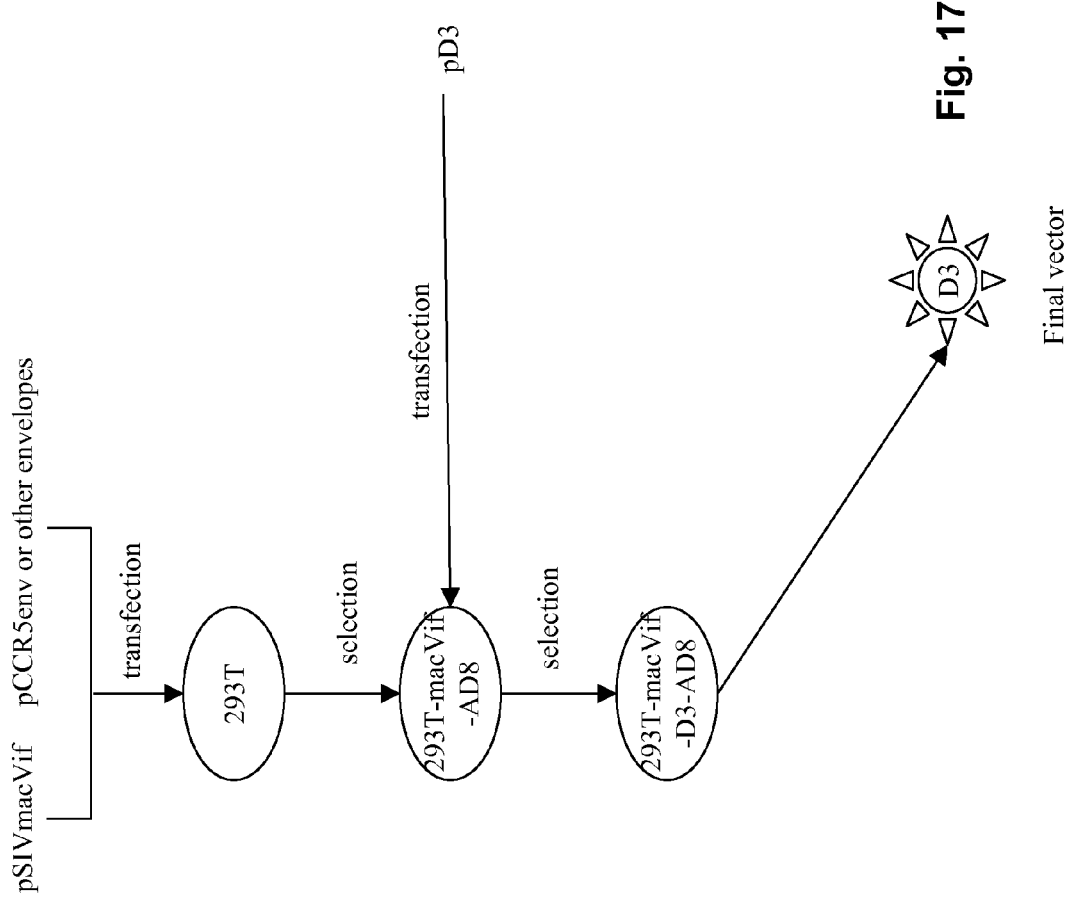

Referring to FIG. 14, in one embodiment transient transfection is used. Plasmids of pSIVmacVif (Simian Immunodeficiency Virus Vif expressing vector), pD3, and pCCR5env (a β-chemokine receptor) or other envelope plasmids such as pCMV-VSVg (VSV-g envelope expression vector) are used to transfect 293 T cells using the CalPhos Mammalian Transfection Kit (BD Biosciences). FIG. 14 shows a method of making a recombinant viral vector with a wild type or mutant A3G gene inserted. Briefly, the recombinant vector D3 is harvested from 293T cells that are transiently transfected with the vector-producing plasmid (pD3), macaque simian immunodeficiency virus' Vif (SIVmacVif) expression vector (pSIVmacVif), and CCR5-tropic envelope expression vector (pCCR5env).

The transfected 293T cells are incubated at 37° C. and 5% $CO_2$. The infectious D3 vectors are filtered and harvested 48 hours after transfection. The p24 capsid of the vector is determined by P24 ELISA kit (PerkinElmer).

Optionally, the CCR5 or other envelope genes can be inserted in pD3 plasmid, and transfect 293 T cell with the pD3 plasmid as two-plasmid transfection system. An advantage of three-plasmid transfecting system, is the relative freedom to select different kind of envelope proteins used to pseudotype the vectors. The CCR5 plasmid can be replaced with various kinds of plasmid encoding different envelope proteins selected from CXCR4 (encoding envelope protein for macrophage), VSVg, SRV or MLV. In one embodiment, CCR5 plasmid is selected to produce envelope protein for the vector so that the envelope protein matches HIV virus' envelope protein. Therefore the vectors can efficiently bind to the same receptors to which HIV virus bind and produce mutant A3G protein on site, interrupting HIV replication more effectively. In another embodiment, CCR5 plasmid subtype is selected to further matches the patient's cellular receptor subtype.

FIG. 15 illustrates another embodiment to produce the recombinant viral vector, which takes several steps of transient transfection to transfect and/or infect 293 T cells to produce the vector. FIG. 15 shows a method of making a recombinant viral vector with a wild type or mutant A3G gene inserted. Briefly, 293T cells are transfected with pSIVmacVif. After selecting for expressing SIVmac Vif, the 293T-macVif cell line that stably express SIVmac Vif is established. The 293T-macVif cell line is infected by D3-VSVg vector produced from 293T that is transiently co-transfected with pSIVmacVif, pD3 and vesicular stomatitis virus protein g (VSVg) expression plasmid, pCMV-VSVg. After infection, the cell lines that stably carry and produce D3 vector (293T-macVif-D3) is selected. The final D3 vector is produced by transiently transfecting 293T-macVif-D3 cell line with CCR5-tropic envelope protein expression vector, pCCR5env. The cells are incubated at 37° C. and 5% $CO_2$ for a period of 48 hours after transfection. The final D3 vectors are harvested from the culture supernatant of this transiently transfected cell line by filtering through a 0.45 μm filter. The p24 capsid of the vector is determined by P24 ELISA kit (PerkinElmer). Unlike HIV Vif, which only degrades wild type A3G protein, SIVmac Vif protein can degrade both wild type and mutant A3G proteins. The purpose of having SIVmac Vif protein expressed in the cytoplasm of the vector-producing cells is to degrade the mutant A3G protein during the vector production, so that the vectors produced from these cells are infectious and can be used in antiretroviral therapies of HIV-1 and HIV-2.

In this method, the recombinant vectors can also have VSVg surface protein through transient transfection, which can bind to many type receptors on various kinds of cells. Therefore, the recombinant vectors can infect other cell types very effectively. The ubiquitous binding character of the vector D3 with VSVg surface protein is useful for gene transfer to many somatic cells such as T cells as well as stem cells, and it can be used for ex vivo gene therapy for transforming hematopoietic cells from bone marrow.

There is an advantage of the method illustrated in FIG. 15. The envelope protein-expression plasmid can be easily switched; therefore, the vectors can be tailor-made to fit the type of the receptors present on the surface of target cells.

FIG. 16 illustrates another embodiment of producing the recombinant viral vector by transient transfection. Briefly, 293T cells are transfected with pSIVmacVif. After selection, the 293T-macVif cell line that stably express SIVmac Vif is established. The 293T-macVif cell line is infected by D3-VSVg vector produced from 293T that is transiently co-transfected with pSIVmacVif, pD3 and vesicular stomatitis virus protein g expression plasmid, pCMV-VSVg. After infection, the cell lines that stably carry D3 vector (293T-macVif-D3) is selected. The final D3 vector is produced by transiently transfecting 293T-macVif-D3 cell line with CCR5-tropic envelope protein expression plasmid, pCCR5env. After transfection, the cell line that stably carries CCR5-tropic envelope protein, 293T-macVif-D3-AD8 is selected and established. The final D3 vectors are harvested from the culture supernatant of this cell line by filtering through a 0.45 μm filter. Unlike the previous method (FIG. 15), this method includes an additional selection step before harvesting the final vector to ensure better stability of the vector product.

FIG. 17 illustrates yet another embodiment of transient transfection of the invention. Briefly, 293T cell line is co-transfected with pSIVmacVif and pCCR5env. After a selection, the 293T-macVif-AD8 cell line is established. This cell line is transfected with pD3 and go through another selection. After the selection, the 293T-macVif-D3-AD8 is established. The final D3 vectors are harvested from the culture supernatant of this cell line by filtering through a 0.45 μm filter.

In this alternative method, the 293T cells are transfected with pSIVmac Vif and CCR5 or other envelope gene expression plasmid. After first selection, the 293T cells with SIVmac Vif gene and CCR5 genes are transfected with pD3 plasmid, which encodes mutant A3G protein. After selection, 293T cell line that stably carry SIVmac Vif, CCR5 genes and D3 provirus (293T-macVif-AD8-D3) is established.

FIG. 18 illustrate yet another alternative method of transient transfection for producing the vector. Briefly, 293T cell line is co-transfected with pSIVmacVif and pCCR5env. After selection, the 293T-macVif-AD8 cell line is established. The 293T-macVif cell line is infected by D3-VSVg vector produced from 293T that is transiently co-transfected with pSIVmacVif, pD3 and pCMV-VSVg and goes through another selection. After the selection, the 293T-macVif-D3-AD8 is established. The final D3 vectors are harvested from the culture supernatant of this cell line by filtering through a 0.45 μm filter.

A series of experiments are conducted to test and verify the recombinant vectors produced. The following paragraphs disclose the procedures employed to do the testing.

In the following testing procedures, many of the genes and plasmids are representative and for illustration only, and can be replaced by similar genes and plasmids. For example, A3G gene can be replaced by wild type A3G gene or other A3G mutant genes such as D128K, D128A, D128G, D128R, P129D, P129A, P129G, P129F; plasmids pSIVmacVif can be replaced by pcDNA3-macVif (mac vif expression plasmid) or other plasmid containing HIV-1 Vif, HIV-2 Vif, SIVagm Vif, SIVmacVif, modified SIVmacVif, natural protein and artificial protein that degrade A3G protein. The vector-producing plasmid pD3 or pD3D128K can be replaced by vector-producing plasmids expressing wild type or mutant A3G such as pD3D128A, pD3D128G, pD3D128R, pD3P129D, pD3P129A, pD3P129G, pD3P129F; pCCR5env (a β-chemokine receptorexpressing plasmid) can be replaced by other envelope plasmids such as pCMV-VSVg (VSV-g envelope expression vector) or pCXCR4env. Many possible replacements of the plasmids can be employed by the person skilled in the art and are included in the scope of the invention.

1) Determining the expression of A3G or A3GD128K. 293 T cells are transfected with either pD3 or pD3D128K. Forty eight hours after transfection, 293T cells from either transfection are harvested. The cmyc-tagged A3G or A3GD128K proteins in the cells are detected by using the monoclonal anti-c-Myc antibody (Sigma-Aldrich) in the immunoblotting analysis and the tubulin protein is detected by using the anti-tubulin antibody (Sigma-Aldrich) to serve as the loading control.

2) Determining antiretroviral effects of pD3 and pD3D128K plasmids on HIV-1 replication in the presence or absence of HIV-1 Vif. 293 T cells are cotransfected with pD3 (or pD3D 128K) and pHDV-EGFP, pcHelp (Vif+) or pcHelp-DVif (Vif−) and pCMV-VSVg. The HIV-GFP viruses are harvested 48 hours after transfection. The p24 capsid of the vector is determined by P24 ELISA kit (PerkinElmer). The viruses containing 30 ng of p24 capsid are used to infect 293T cells. Forty eight hours after infection, the 293T cells are harvested, and are analyzed by flow cytometry (FACScan; Becton-Dickinson) for green fluorescence and the results are analyzed using CellQuest software (Becton-Dickinson). The result shows that both pD3 and pD3D128K plasmids inhibited HIV-1 replication more than 90% when they were cotransfected into the 293T cells (viral producing cells) in the absence of HIV-1 (cotransfected with pcHelpDVif). In the presence of HIV-1 Vif (cotransfected with pcHelp), pD3D128K plasmid inhibited replication of HIV-GFP about 90% while pD3 lost its ability of viral inhibition.

3) Determining production of infectious vectors from pD3 and pD3D128K. 293 T cells are transfected with pcDNA3macVif, pCMV-VSVg and either pD3 or pD3D128K. The infectious D3 or D3D128K vectors are harvested 48 hours after transfection, and p24 capsid of the vectors is determined by P24 ELISA kit (PerkinElmer). The infectious vectors that contained 30 ng of p24 capsid are used to infect 293T cells. The infected cells are harvested 48 hours after infection, and are analyzed by flow cytometry (FACScan; Becton-Dickinson) for green fluorescence. The result shows that 24% and 26% of the infected cells are green fluorescent in the samples that are infected by D3 and D3D128K, respectively.

4) Testing expression of A3G or A3GD128K in D3 or D3D128K transformed 293T cells. To produce infectious D3 or D3D128K vectors, 293T cells are co-transfected with pD3, pcDNA3-macVif (mac vif expression vector), pCMV-VSVg (VSV-g envelope expression vector) using the CalPhos Mammalian Transfection Kit (BD Biosciences) and the transfected 293T cells are incubated. The infectious D3 vectors were harvested 48 hours after transfection. The p24 capsid of the vector is determined by P24 ELISA kit (PerkinElmer). 293T cells are infected by either one of the vectors (D3 or D3D128K) containing 30 ng of p24 capsid. Forty eight hours after infection, cells are harvested. The A3G and A3GD128K expressed in the D3 and D3D128K-transformed cells are detected by immunoblotting analysis using monoclonal anti-c-Myc antibody (Sigma-Aldrich).

The final vectors are now ready for clinical use.

Method of Gene Therapy Application

The recombinant vector with expression of a wild type A3G gene or a mutant A3G gene can be used to treat HIV infected individuals, delay the onset of AIDS and treat AIDS patients, both in vivo and ex vivo. Further more, the recombinant vector with the wild type A3G gene or the mutant A3G gene can be used to prevent HIV infection by administrating to a healthy individual.

In one embodiment, in vivo method is provided for treating or preventing HIV infection. A subject is administered a recombinant viral vector such as a D3GFP vector, or a D3 vector, or a D3 min vector, in which the vector has a mutant A3G gene or with excessive expression of a wild type A3G gene. The vector can be packaged with pharmaceutically suitable salts and solvates, administered to an individual infected with HIV virus or an AIDS patient.

Administering the recombinant vector with the A3G gene or the mutant A3G gene of the invention may be conveniently administered in unit dosage form, and may be prepared by any of the methods well known in the pharmaceutical art. The gene therapy agent further comprises at least one other agent of common excipients for treating HIV infection, such as sterile water or saline, polyalkylene glycols, oils of vegetable origin, hydrogenated naphtalenes, and the like.

The recombinant vector with A3G gene or mutant A3G gene and at least a packaging material may be formulated into pharmaceutical compositions by admixture with pharmaceutically acceptable non-toxic excipients or carriers, such as salt and solvates. Such compounds and compositions may be prepared in the intravenous form, subcutaneous form, or intramuscular form for parenteral administration, particularly in the form of liquid solutions or suspensions in aqueous physiological buffer solutions; for oral administration, particularly in the form of tablets or capsules; or in inhalation form for intranasal administration, particularly in the form of powders, nasal drops, or aerosols; or on the mucosa forms of liquid solutions or suspensions for applications.

Sustained release compositions are also encompassed by the present invention. Compositions for other routes of administration may be prepared as desired using standard methods.

The invention also relates to an article of manufacturing containing at least one packaging material and the recombinant viral vector with A3G gene or mutant A3G gene thereof contained within the packaging material. The packaging material may contain a label or package insert indicating that the recombinant viral vector with A3G gene or mutant A3G gene thereof may be used for treating HIV infection and AIDS.

The packaging material is capable of forming pharmaceutically acceptable salts, including acid addition salts and base salts, as well as solvates, such as hydrates and alcoholates. All of these pharmaceutical forms are contemplated by this invention and are included herein.

The ex vivo method will be specially designed for treating HIV infected individuals, delaying the onset of AIDS and treating AIDS patients, since the ex vivo transformation of bone marrow stem cells will be more efficient than transfecting somatic cells and stem cells in vivo. However, more complicated clinical procedure to draw bone marrow from the patient, which may not be suitable to serve for a prevention purpose, will be used. The advantage of ex vivo procedure is that it targets mainly the hematopoietic stem cells that will replicate and differentiate to all types of blood cell including T cells and macrophages, the method is a more effective way to treat the patients.

The ex vivo procedure requires withdrawing bone marrow from the HIV-infected individual. The hematopoietic stem cells from the bone marrow are isolated and cultivated using methods known to the art, and transformed with a therapeutically effective amount of recombinant viral vector encoding excessive wild type A3G protein or mutant A3G protein with pharmaceutically acceptable salts or solvates, and packaging materials. The transformed hematopoietic stem cells are then verified with immunoblotting analysis to check the wild type A3G gene or mutant A3G gene expression in the cells. After screening and selecting, the transfected hematopoietic stem cells are transplanted back into the HIV-infected individual.

Another embodiment of ex vivo procedure is that the T cells and macrophages are isolated from the HIV infected individual or the AIDS patient, and then the isolated cells are transformed. This procedure is relatively easy to perform than the bone marrow procedure clinically. The ex vivo procedure requires withdrawing blood from the HIV-infected individual, then the T cells and macrophages are isolated from the blood, cultivated and transformed with a therapeutically effective amount of recombinant viral vector encoding excessive wild type A3G protein or mutant A3G protein, with pharmaceutically acceptable salts or solvates, and packaging materials. The transformed T cells and macrophages are then verified with immunoblotting analysis to check the wild type A3G gene or mutant A3G gene expression in the cells. After screening and selecting, the transformed T cells and macrophages are transfused back into the HIV-infected individual.

EXAMPLES

The invention will be further described in the following examples, which do not limit the scope of the invention described in the claims.

Experiment 1

Preparation of D3GFP Vector

To produce infectious D3GFP or D3GFPD128K vectors, 293T cells were co-transfected with pD3GFP or pD3GFPD128K, pcDNA3-macVif (mac vif expression plasmid), pCMV-VSVg (VSV-g envelope expression vector) using the CalPhos Mammalian Transfection Kit (BD Biosciences) and the transfected 293T cells were incubated at 37° C. and 5% $CO_2$. The infectious D3GFP vectors were harvested 48 hours after transfection by filtering through 0.45 µm syringe filter (Corning). The p24 capsid of the vector was determined by P24 ELISA kit (PerkinElmer).

Experiment 2

Test of pD3GFP Plasmid and D3GFP Vector

1). To determine the expression of A3G or A3GD128K from pD3GFP or pD3GFPD128K, 293T cells were transfected with either pD3GFP or pD3GFPD128K. Forty eight hours after transfection, $2 \times 10^6$ cells from either transfection were harvested, washed with ice-cold PBS, lysed in 1× SDS-PAGE loading buffer, and heated to 90° C. for 5 minutes. The cmyc-tagged A3G or A3GD128K proteins in the cells were detected by using the monoclonal anti-c-Myc antibody (Sigma-Aldrich) in the immunoblotting analysis and the tubulin protein was detected by using the anti-tubulin antibody (Sigma-Aldrich) to serve as the loading control. The result showed that both pD3GFP and pD3GFPD128K expressed detectable levels of A3G and A3GD128K in transfected 293T cells.

Figure 19:
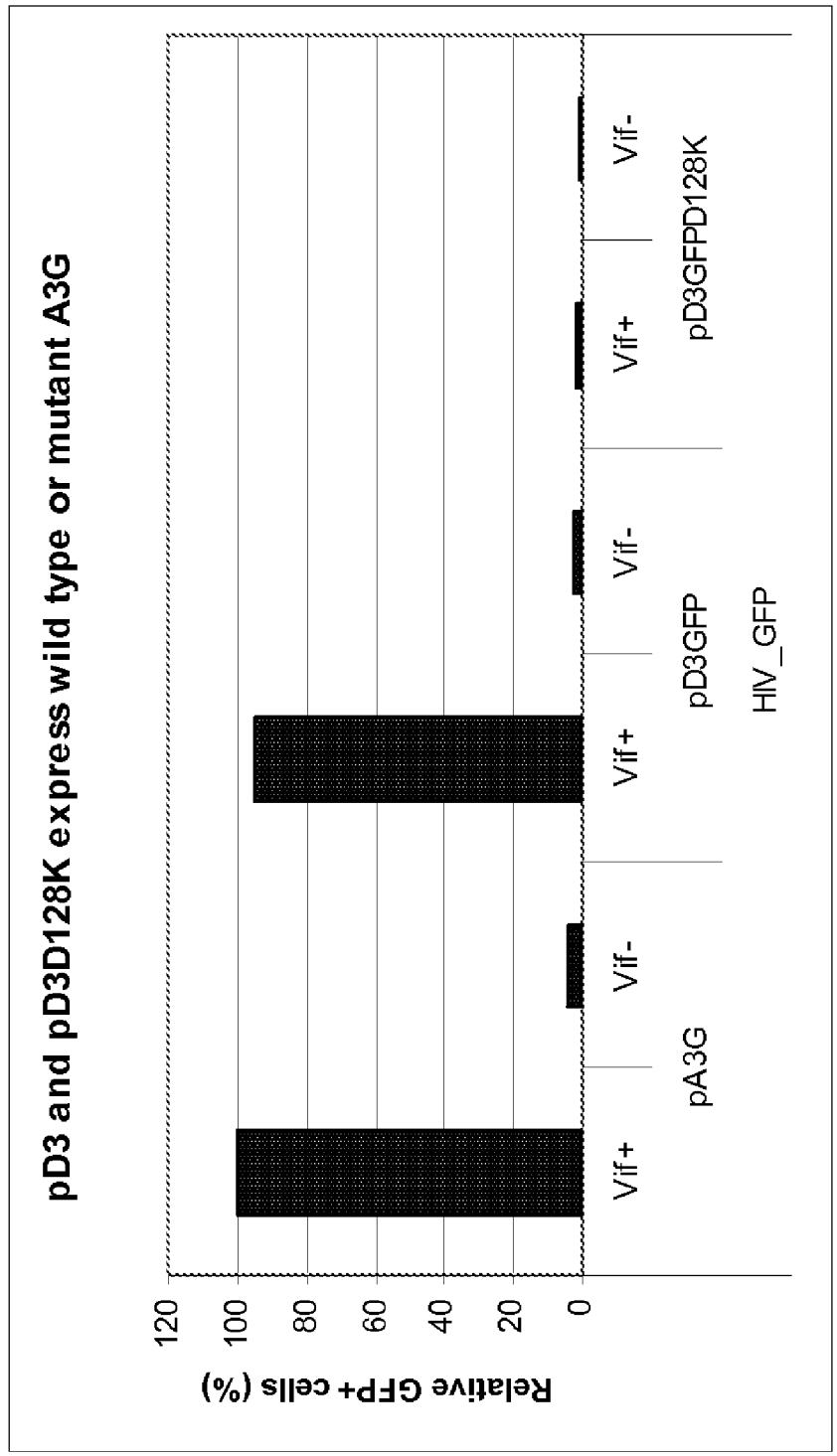
FIG. 19 shows the vector-producing plasmids, pD3GFP and pD3GFPD128K express wild type or mutant A3G and inhibit replication of HIV-GFP, a Vif-deficient HIV-1 that express GFP as reporter.

2). To determine the antiretroviral effects of pD3GFP and pD3GFPD128K plasmids on HIV-1 replication in the presence or absence of HIV-1 Vif, 293T cells were cotransfected with either 8 µg of pD3GFP or pD3GFPD128K and 20 µg of pHDV-EGFP, 10 µg of pcHelp (Vif+) or pcHelpΔVif (Vif−) and 4 µg of pCMV-VSVg. The HIV-GFP viruses were harvested 48 hours after transfection by filtering through 0.45 µm syringe filter (Corning). The p24 capsid of the vector was determined by P24 ELISA kit (PerkinElmer). The viruses containing 30 ng p24 capsid were used to infect 293T cells. Forty eight hours after infection, the 293T cells were harvested, washed with ice-cold PBS, fixed with 1% formaldehyde and were analyzed by flow cytometry (FACScan; Becton-Dickinson) for green fluorescence and the results were analyzed using CellQuest software (Becton-Dickinson). The result showed that both pD3GFP and pD3GFPD128K plasmids inhibited HIV-1 replication more than 90% when they were cotransfected into the 293T cells (viral producing cells) in the absence of HIV-1 (cotransfected with pcHelpDVif). In the presence of HIV-1 Vif (cotransfected with pcHelp), pD3GFPD128K plasmid inhibited replication of HIV-GFP about 90% while pD3GFP lost its ability of viral inhibition (FIG. 19).

Figure 20:
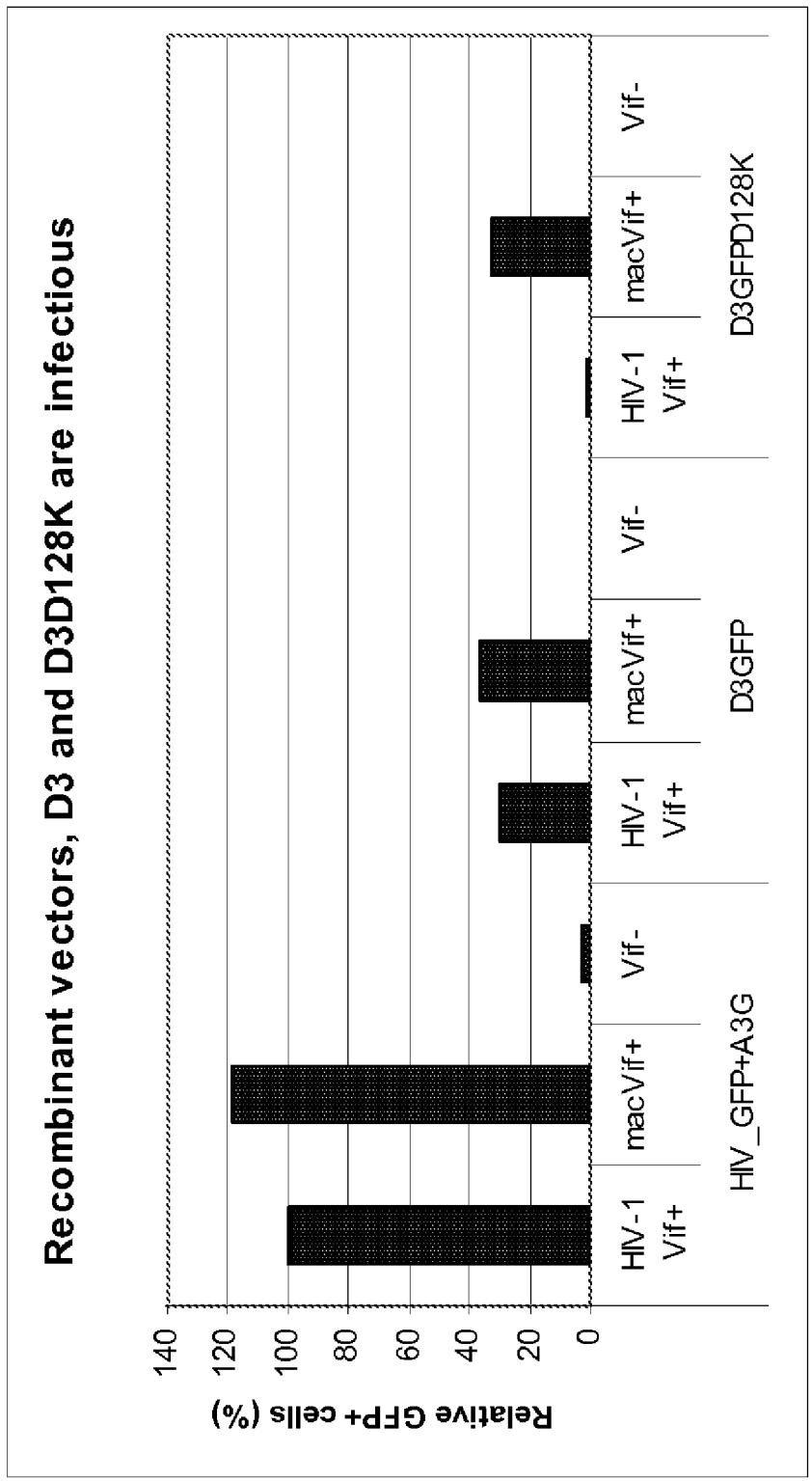
FIG. 20 shows the recombinant vectors, D3GFP and D3GFPD128K produced by method illustrated in FIG. 14 are infectious.

3). To determine the infectious vector production from pD3GFP and pD3GFPD128K, 293T cells were transfected with 10 µg of pcDNA3macVif, 4 µg of pCMV-VSVg and either 20 µg of pD3GFP or 20 µg of pD3GFPD128K, and the samples that co-transfected with pC-Help (HIV-1 Vif+) served as controls. The infectious D3GFP or D3GFPD128K vectors were harvested 48 hours after transfection by filter through 0.45 µm syringe filter (Corning) and p24 capsid of the vectors was determined by P24 ELISA kit (PerkinElmer). The infectious vectors that contained 30 ng of p24 capsid were used to infect 293T cells. The infected cells were harvested 48 hours after infection, washed in ice-cold PBS, fixed in 1% formaldehyde and analyzed by flow cytometry (FACScan; Becton-Dickinson) for green fluorescence. The result showed that 24% and 26% of the infected cells were green fluorescent in the samples that were infected by D3GFP and D3GFPD128K, respectively. The result indicated that the both D3GFP and D3GFPD128K vectors that produced from the pD3GFP and pD3GFPD128K were infectious (FIG. 20).

4). Expression of A3G or A3GD128K in D3GFP or D3GFPD128K transformed 293T cells. To produce infectious D3GFP or D3GFPD128K vectors, 293T cells were co-transfected with pD3GFP, pcDNA3-macVif (mac vif expression vector), pCMV-VSVg (VSV-g envelope expression vector) using the CalPhos Mammalian Transfection Kit (BD Biosciences) and the transfected 293T cells were incubated at 37° C. and 5% $CO_2$. The infectious D3GFP vectors were harvested 48 hours after transfection by filtering through 0.45 μm syringe filter (Corning). The p24 capsid of the vector was determined by P24 ELISA kit (PerkinElmer). 293T cells were infected by either one of the vectors containing 30 ng of p24 capsid. Forty eight hours after infection, $2\times10^6$ cells were harvested, washed by ice-cold PBS and lysed in 1× SDS loading buffer. The A3G and A3GD128K expressed in the D3GFP and D3GFPD128K-transformed cells were detected by immunoblotting analysis using monoclonal anti-c-Myc antibody (Sigma-Aldrich). The result showed that both transformed cells expressed detectable levels of A3G and A3GD128K.

5). Determining infectivities of HIV-1 produced from D3GFP or D3GFPD128K vectors transformed 293T cells.

To produce infectious vectors, 293T cells were co-transfected with 4 μg pCMV-VSVg, 10 μg pSIVmacVif and 20 μg of pD3GFP or pD3GFPD128K. The infectious D3GFP and D3GFPD128K vectors were harvested 48 hours after the transfection by filtering through 0.45 μm syringe filters (Corning). The p24 capsid associated with the vectors were determined by P24 ELISA kit (PerkinElmer).

To produce D3GFP or D3GFPD128K vector-carrying 293T cells, either of the vectors containing 100 ng of p24 capsid were used to infect 293T cells. The infected cells that expressed GFP were sorted out 48 hours after infection using fluorescent activated cell sorter (Becton-Dickinson). The GFP+293T cells (carrying D3GFP or D3GFPD128K) were grown in fresh DMEM medium in 5% $CO_2$ and 37° C. for another 48 hours.

To produce HIV-GFP from vector-carrying 293T cells in the presence HIV-1 Vif (Vif+) or absence HIV-1 Vif (Vif−), $1\times10^6$ 293T and D3GFP or D3GFPD128K-carrying 293T cells were re-plated and transfected with 20 μg pHIV-GFP, 4 μg pCMV-VSVg and 10 μg of pcHelp or pcHelpΔVif. The HIV-GFP viruses were harvested 48 hours after transfection by filtering through 0.45 μm syringe filters (Corning). The p24 capsid associated with the vectors were determined by P24 ELISA kit (PerkinElmer).

To determine the infectivities of the HIV-1 (HIV-GFP) produced from vector-carrying 293T cells, the viruses containing 30 ng of p24 were used to infect 293T cells. The infected 293T cells were harvested 48 hours after infection, washed by ice-cold PBS, fixed in 1% formaldehyde and analyzed by flow cytometry. The 293T cells infected by HIV-GFP of 30 ng p24 produced from transfected 293T (carrying no vector) were served as control. The percentage of GFP+ cells in control was set as 100%.

Figure 21:
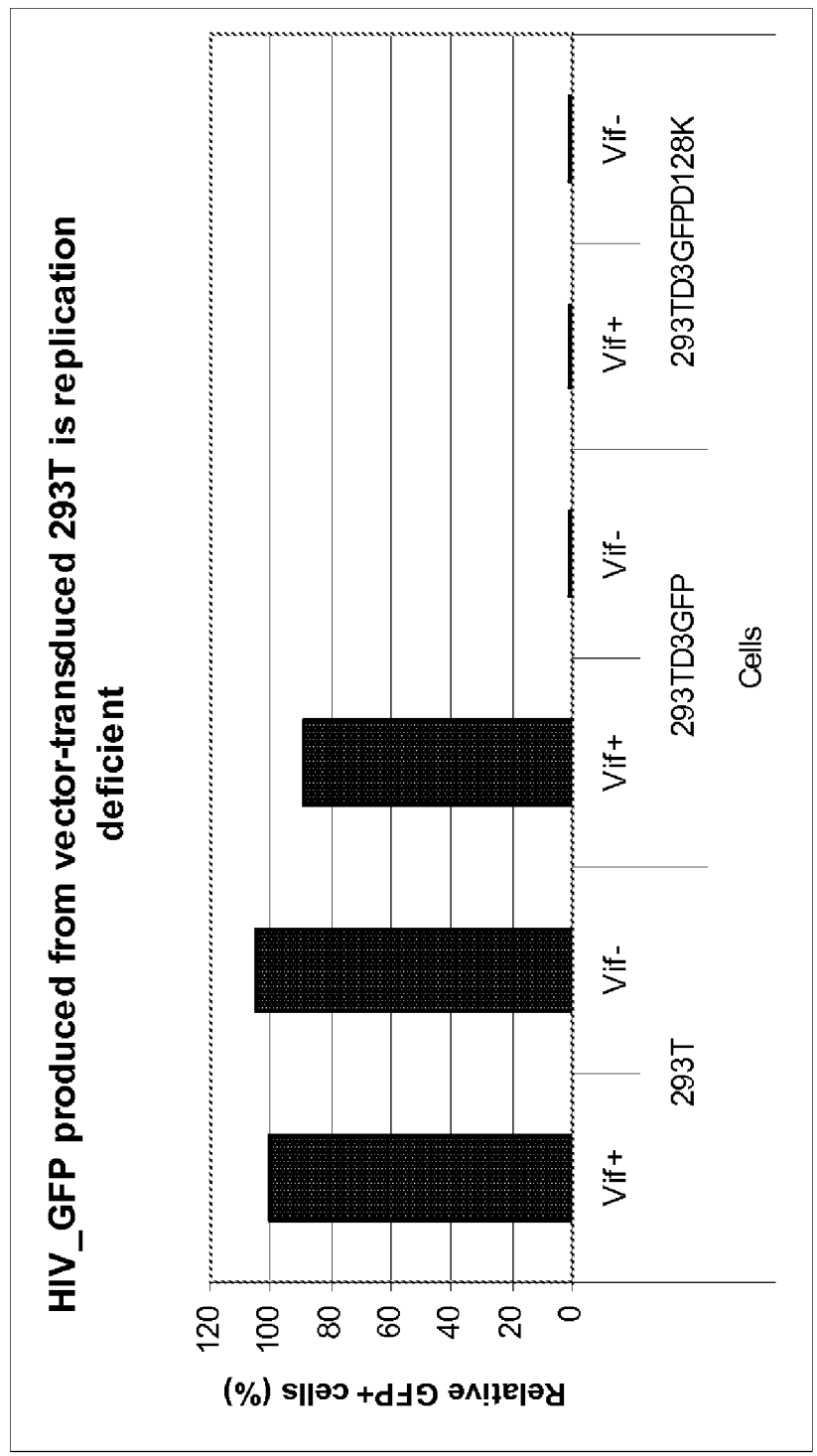
FIG. 21 shows HIV-GFP produced from 293T cells transformed by D3GFP or D3GFPD128K is replication deficient.

The result showed that in the absence of HIV-1 Vif (Vif−), the infectivities of HIV-GFP viruses produced from 293T cells carrying either D3GFP or D3GFPD 128K were 1% and 1.2% of that of the control, respectively. In the presence of HIV-1 Vif, the infectivity of HIV-GFP virus produced from D3GFP-carrying 293T was on average 89% of the control, while the infectivity of HIV-GFP virus produced from D3GFPD128K-carrying 293T cells was only 1% of that of control. The result indicated that D3GFP and D3GFPD128K efficiently transformed viral producing cells and resulted significant reduction on infectivities of the HIV-1 viruses produced from these transformed cells (FIG. 21).

6). Cell transformation by D3GFPD128K inhibits replication of wild type HIV-1 (strain of NL43).

The Hut78 is a human T cell line that has CCR5 receptor on its surface. Like human CD4+ T cells, Hut78 can be infected by wild type HIV-1. To determine the inhibition of NL43 in D3GFPD128K transformed cells, the D3GFPD 128K-carrying 293T cells were produced as described above (in last section). To produce NL43, D3GFPD 128K-carrying 293T was transfected with 20 μg pNL43 and 4 μg of pCCR5env. The virus was harvest 48 hours after transfection by filtering through 0.45 mm syringe filter (Corning). The NL43 produced from non-transformed 293T cells was served as control. The p24 capsid associated with the vectors was determined by P24 ELISA kit (PerkinElmer). To determine the viability of the NL43 virus, Hut78 cells were infected with the NL43 viruses containing 100 ng of p24 produced from 293T or D3GFPD128K-carrying 293T cells. The infected cells were washed 3 times 24 hours after infection and incubated for additional 48 hours. The culture supernatant of the infected Hut78 cells were harvested by filtering through 0.45 μm syringe filters (Corning). The p24 capsid of the supernatant were determined by P24 ELISA kit (PerkinElmer).

Figure 22:
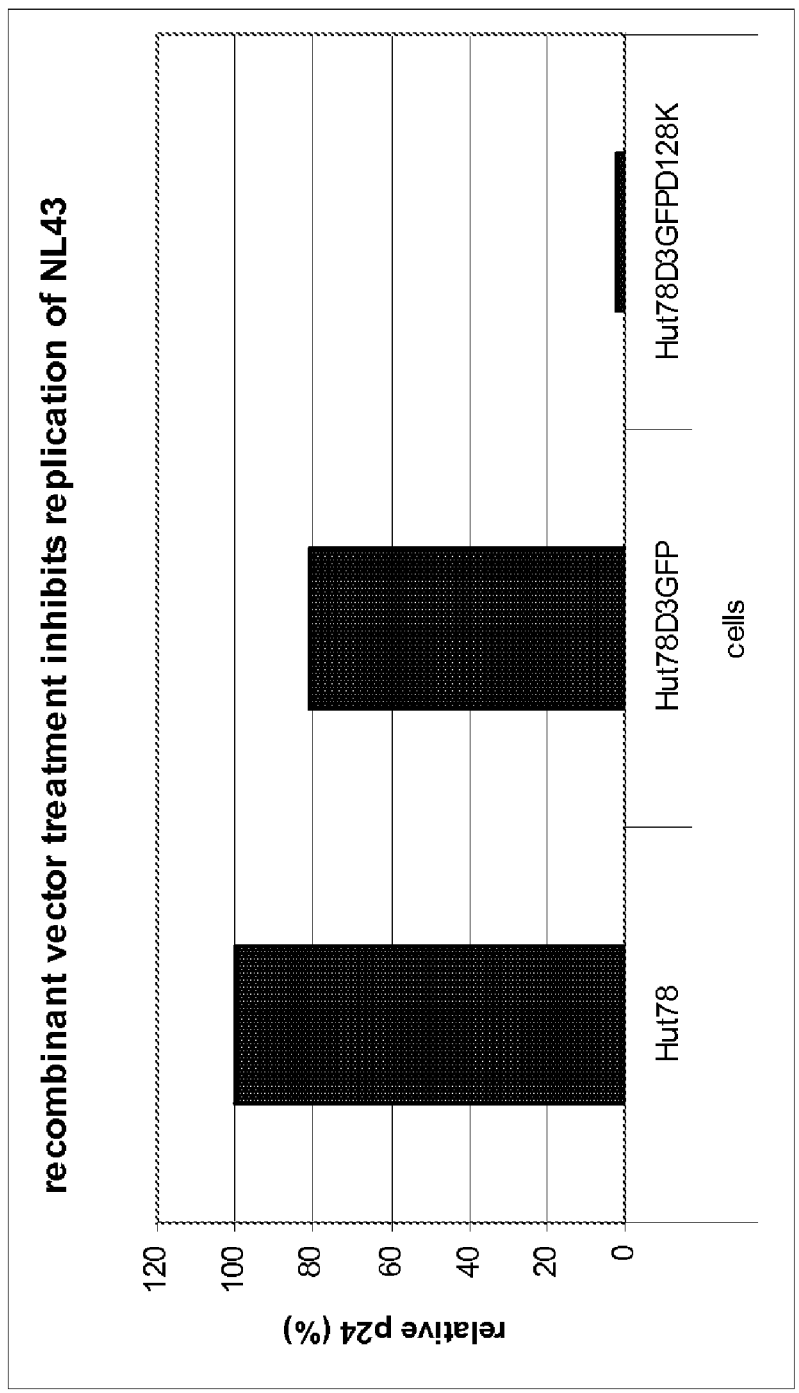
FIG. 22 shows replication of wild type HIV-1 (strain of NL43) is inhibited in D3GFP or D3GFPD128K-transformed Hut78 cells (a human T cell line).

The result showed that the p24 in supernatant of Hut78 infected with the NL43 that was produced from D3GFPD128K-carrying 293T was only 2% of that in supernatant of the control. The result indicated that wild type HIV-1 produced from D3GFPD 128K transformed cells was defective in its replication, and D3GFP and D3GFPD128K are vectors that can effectively deliver antiviral genes to inhibit HIV-1 replication (FIG. 22).

Experiment 3

Flow Cytometry and Cell Sorting

For flow cytometry analysis, 293T cells were washed with ice-cold PBS, trypsinized and fixed in 1% formaldehyde for 30 minutes. The fixed cells were analyzed by Facs and percentage of GFP positive (+) cells was analyzed. For cell sorting for GFP positive (+) 293T cells, 293T cells were washed with ice-cold PBS, trypsinized and re-suspended in dye-free DMEM with 10% calf serum and 1% penicillin and streptomycin. The GFP positive (+) 293T cells were sorted out at rate of 1000 cells per second using cell sortor and into a sterile 15 ml conical tube (Corning).

Experiment 4

Cell Culture

The original 293T were grown in DMEM with 10% calf serum and 1% penicillin and streptomycin. Cells were incubated in 37° C. with 5% $CO_2$. Hut78 cells were grown in RPMI1640 with 10% calf serum and 1% penicillin and streptomycin. Cells were incubated in 37° C. with 5% $CO_2$.

In the foregoing description and examples, limited and narrow interpretation of descriptive language intended to better illustrate the invention is not to be construed as limiting in any way nor to limit the scope of the invention contemplated by the inventor. It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. A method for producing a recombinant vector from a vector-producing cell line, wherein the vector comprising mutant Apolipoprotein B mRNA-editing enzyme-catalytic polypeptide-like 3G (A3G) genes for delivering said mutant A3G genes into human target cells comprising the steps of:
   a) establishing a cell line by culturing a cell line in a culture medium,
   b) transfecting the cell line with supporting plasmids containing a Vif gene, wherein said Vif gene expresses a Vif protein in the cell line,
   c) selecting the cell line stably expressing the Vif protein,
   d) infecting the cell line of step c) with a recombinant vector comprising (i) a gene expression block including a mutant A3G gene and (ii) a group of elements from a modified lentiviral vector including lentiviral regions of packaging signal (ψ, psi), long-term repeats (LTRs), Rev responsive element (RRE), and primer binding site (PBS); wherein said mutant A3G gene is operably linked to the packaging signal (ψ, psi), LTRs, RRE, and PBS,
   e) selecting the cell lines stably producing the recombinant vector, and
   f) expressing envelope proteins in the selected cell line of step e) and harvesting the recombinant vector from the culture medium.

2. The method for producing the recombination vector according to claim 1, wherein the step b) is transiently transfecting the cell line with supporting plasmids containing a Vif gene.

3. The method for producing the recombination vector according to claim 1, wherein the step of transfecting the cell line further comprising expressing small interference RNA (siRNA) in the cell line to disrupt the production of A3G proteins within the cells of the cell line.

4. The method for producing the recombination vector according to claim 1, wherein the step of transfecting the cell line further comprising expressing small interference RNA (siRNA) within the cells of the cell line.

5. The method for producing the recombination vector according to claim 1, wherein the Vif protein is selected from the group of proteins consisting of HIV-2 Vif, SIVagm Vif, SIVmacVif, and modified SIVmacVif proteins.

6. The method for producing the recombination vector according to claim 1, wherein the Vif gene is modified SIVmacVif gene.

7. The method for producing the recombination vector according to claim 6, wherein the modified SIVmacVif gene comprises nucleotide sequence SEQ ID NO: 8.

8. The method for producing the recombination vector according to claim 6, wherein the modified SIVmacVif is modified from a SIVmacVif by using codons preferred by human cells.

* * * * *